United States Patent
Lin et al.

(10) Patent No.: US 9,647,217 B2
(45) Date of Patent: May 9, 2017

(54) ORGANIC ELECTROLUMINESCENT MATERIALS AND DEVICES

(71) Applicant: Universal Display Corporation, Ewing, NJ (US)

(72) Inventors: Chun Lin, Yardley, PA (US); Lichang Zeng, Lawrenceville, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 507 days.

(21) Appl. No.: 14/188,297

(22) Filed: Feb. 24, 2014

(65) Prior Publication Data

US 2015/0243904 A1     Aug. 27, 2015

(51) Int. Cl.
*H01L 51/00* (2006.01)
*C07D 409/14* (2006.01)
*H01L 51/50* (2006.01)

(52) U.S. Cl.
CPC ........ *H01L 51/0072* (2013.01); *C07D 409/14* (2013.01); *H01L 51/0071* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Nathan T Leong
(74) *Attorney, Agent, or Firm* — Duane Morris LLP

(57) ABSTRACT

The present invention relates to novel organic compounds comprising at least two different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene. The compounds are useful for organic light-emitting diodes. The compounds are also useful for charge-transport and charge-blocking layers, and as hosts in the light-emissive layer for organic light emitting devices (OLEDs).

21 Claims, 3 Drawing Sheets

(56) References Cited

U.S. PATENT DOCUMENTS

| | | |
|---|---|---|
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0212626 A1* | 9/2007 | Toshine ............... G03G 5/0542 430/58.7 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1* | 1/2009 | Iwakuma ............... C09K 11/06 428/690 |
| 2009/0030202 A1* | 1/2009 | Iwakuma ............... C07D 333/76 544/251 |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0284138 A1* | 11/2009 | Yasukawa ............ C09K 11/06 313/504 |
| 2012/0235136 A1* | 9/2012 | Ogawa ................ C07D 209/86 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2011082238 | 4/2011 |
| JP | 2013206649 | 10/2013 |
| WO | 01/39234 | 5/2001 |
| WO | 02/02714 | 1/2002 |
| WO | 0215654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009085344 | 7/2009 |
| WO | 2009086028 | 7/2009 |
| WO | 2009100991 | 8/2009 |
| WO | 2010004877 | 1/2010 |
| WO | 2013012298 | 1/2013 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)indium(III) Derivatives," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes containing N^C ^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater, 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Lee, C.W. et al., Diphenylmethyl Linked High-Triplet-Energy Material as a Host for Deep-Blue Phosphorescent Organic Light-Emitting Diodes, Thin Solid Films, Feb. 4, 2013, vol. 531, pp. 541-544, Republic of Korea.
EPO Communication pursuant to Article 94(3) EPC issued Feb. 6, 2017 for corresponding EP Application No. 15000452.1.

* cited by examiner

Compound 15

ORGANIC ELECTROLUMINESCENT MATERIALS AND DEVICES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic compounds comprising at least two different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene. The compounds are useful for organic light-emitting diodes. The compounds are also useful for charge-transport and charge-blocking layers, and as hosts in the light-emissive layer for organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

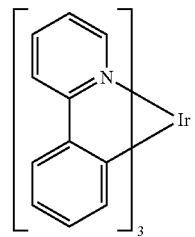

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

BRIEF SUMMARY OF THE INVENTION

A new class of compounds comprising at least two different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene is provided.

The present invention provides compounds having formula I:

A-L-B  (I).

In the compound of formula I, A and B are each different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;
A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;
L is selected from the group consisting of alkyl, cycloalkyl, substituted alkyl, and substituted cycloalkyl; and
L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, A including optional substituents and B including optional substituents are different.

In some embodiments, the compound of formula I further comprises C, wherein C is selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;
C can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

C is connected to A or B by L'; wherein L' is selected from the group consisting of alkyl, cycloalkyl, substituted alkyl, and substituted cycloalkyl; and
L' can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, A and B have no further substitution.

In some embodiments, C is a different selection from the group consisting of N-phenyl carbazole, dibenzofuran, dibenzothiophene, triphenylene, aza-(N-phenyl carbazole), aza-dibenzofuran, aza-dibenzothiophene, and aza-triphenylene than A and B.

In some embodiments, A, B, and C have no further substitution.

In some embodiments, no more than one of A, B, and C is aza-(N-phenyl carbazole), aza-dibenzofuran, aza-dibenzothiophene, or aza-triphenylene.

In some embodiments, A and B are each independently selected from the group consisting of N-phenyl carbazole, aza-(N-phenyl carbazole), dibenzofuran, dibenzothiophene, and triphenylene.

In some embodiments, A is selected from the group consisting of N-phenyl carbazole, dibenzofuran, dibenzothiophene, and triphenylene; and B is selected from the group consisting of aza-(N-phenyl carbazole), aza-dibenzofuran, aza-dibenzothiophene, and aza-triphenylene.

In some embodiments, L has from 1 to 24 carbon atoms.
In some embodiments, L' has from 1 to 24 carbon atoms.
In some embodiments, L is selected from the group consisting of

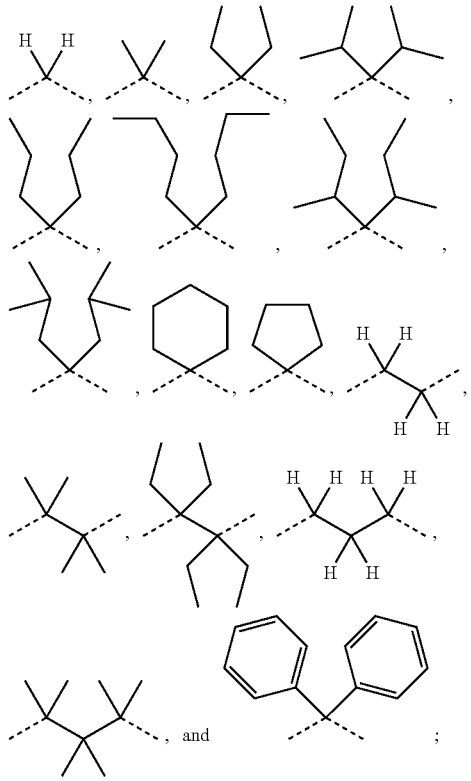

and wherein the dash lines represent a direct bond between L and A, and L and B.

In some embodiments, L' is selected from the group consisting of

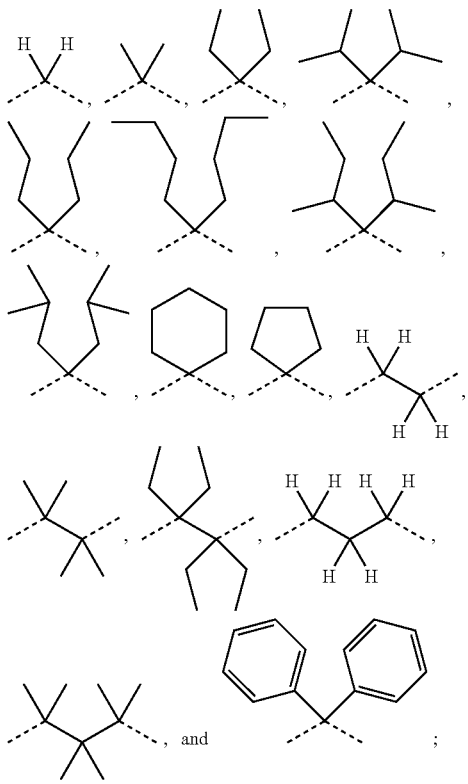

and wherein the dash lines represent a direct bond between L' and C, and L' and A or B.

In some embodiments, A or B is (9-carbazolyl)-(N-phenyl-carbazole).

In some embodiments, the aza-(N-phenyl carbazole) is selected from the group consisting of N-pyridyl carbazole, N-pyrazinyl carbazole, and N-triazinyl carbazole.

In some embodiments, the compound is selected from the group consisting of:

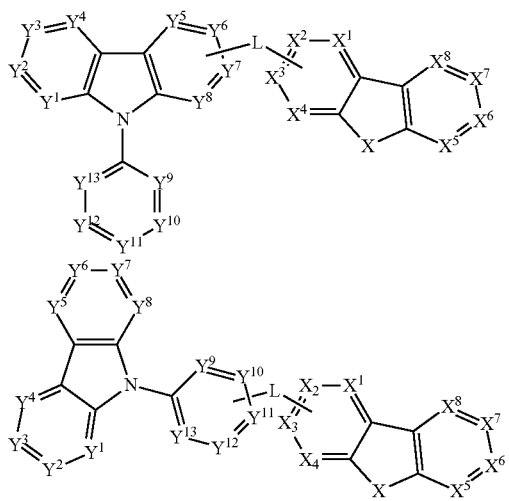

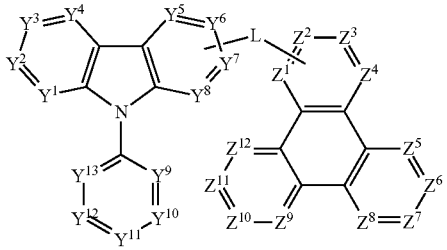

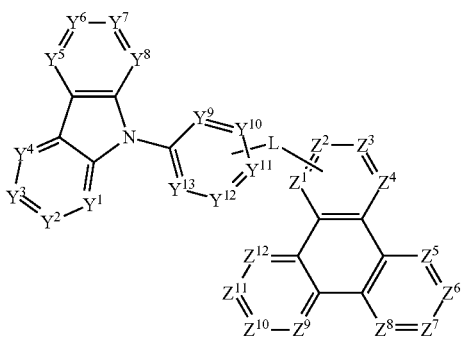

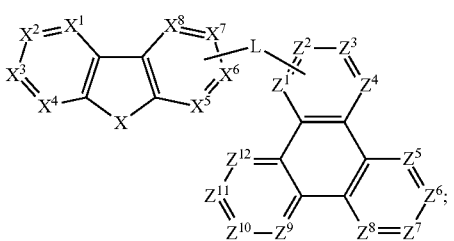

wherein X is O or S;

wherein $X^1$ to $X^8$, $Y^1$ to $Y^{13}$, and $Z^1$ to $Z^{12}$ are each independently selected from the group consisting of CR and N; and wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

In some embodiments, the compound is selected from the group consisting of:
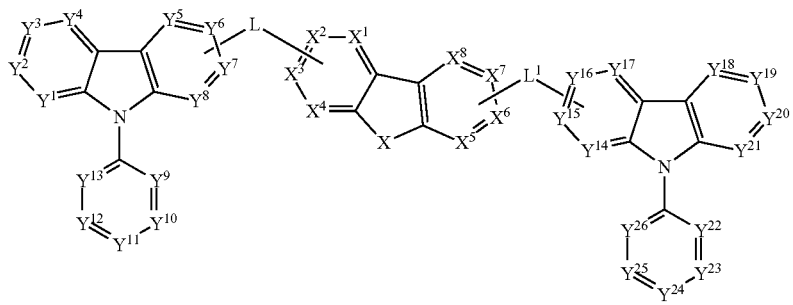
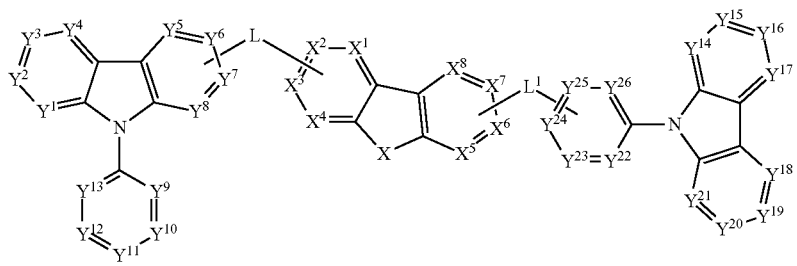
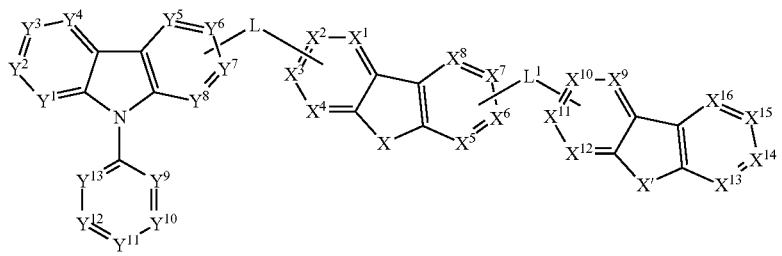
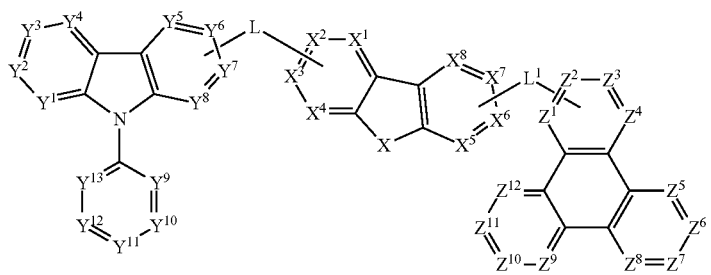
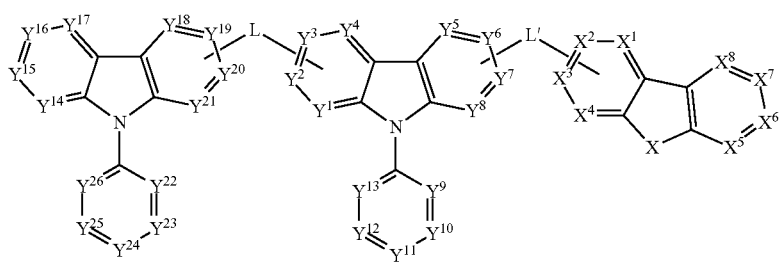

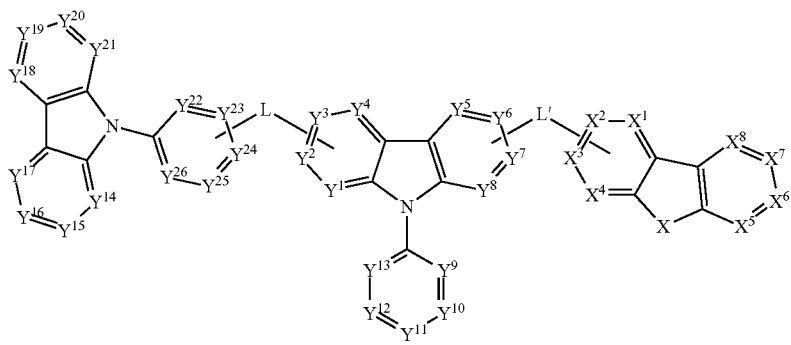
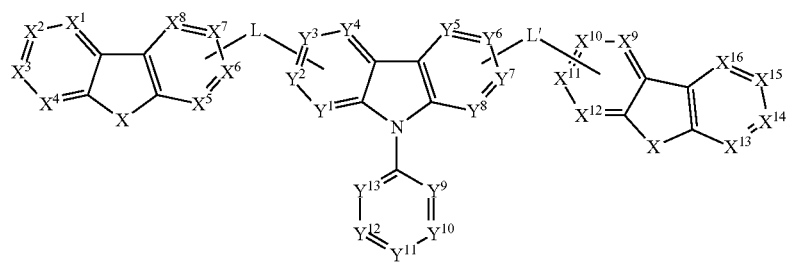
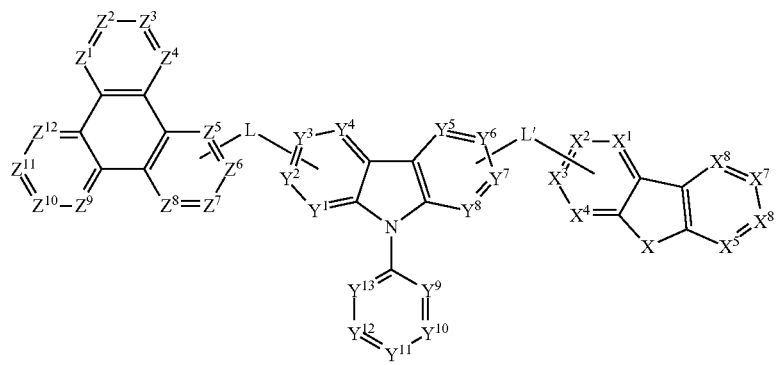
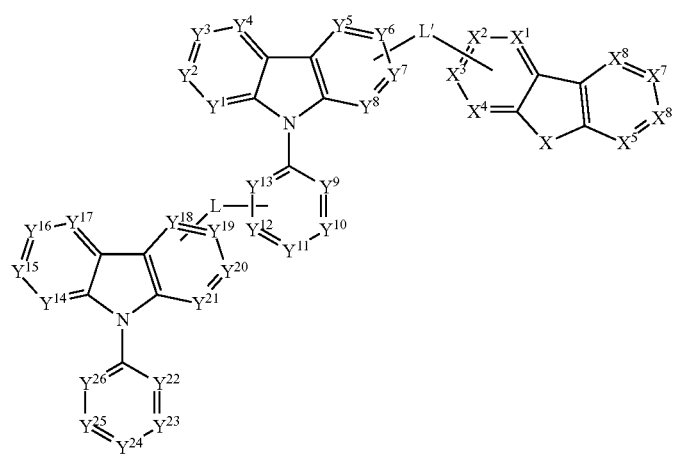

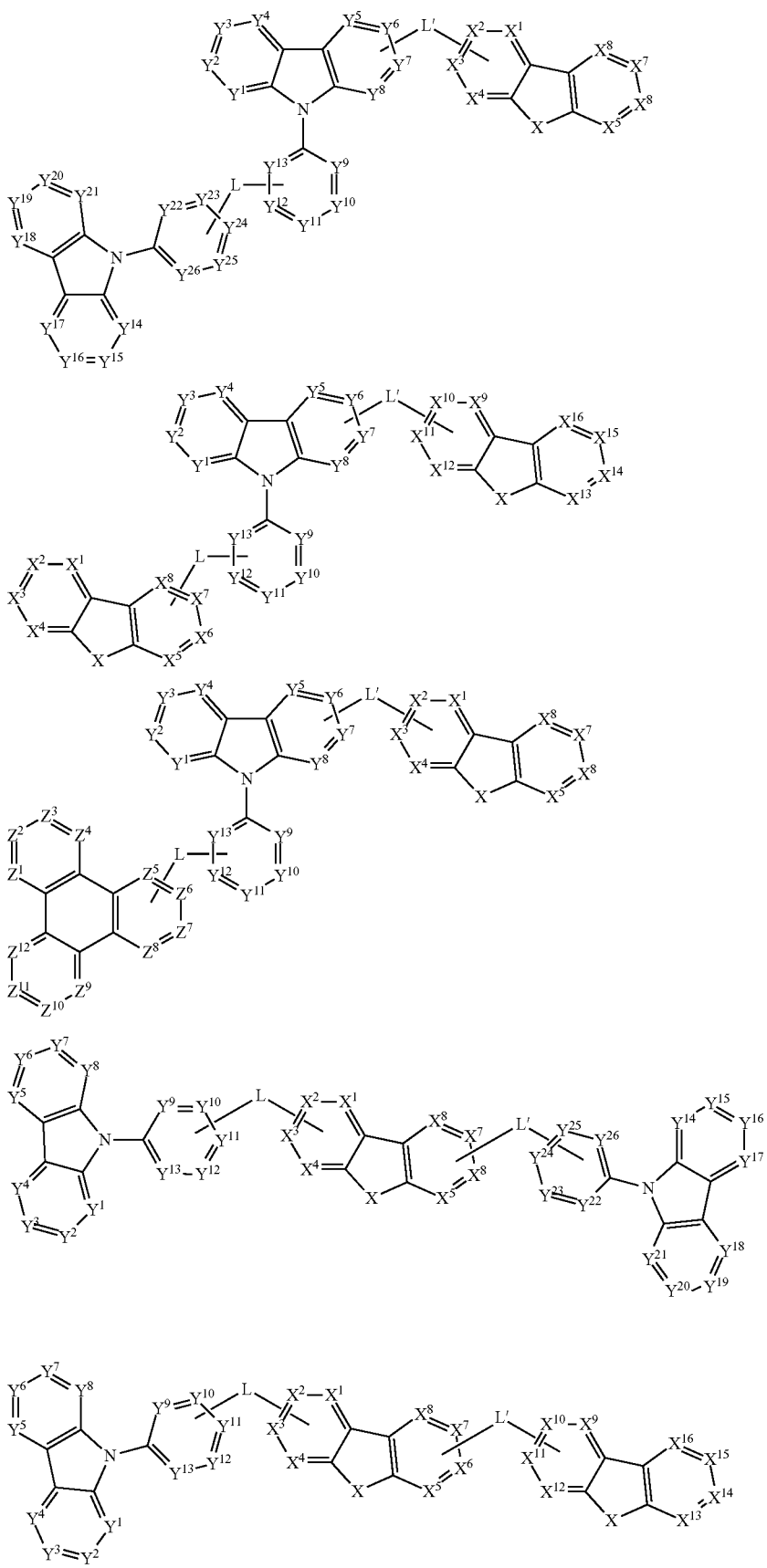

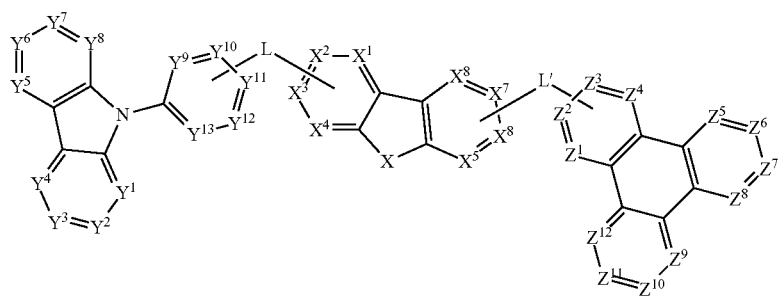
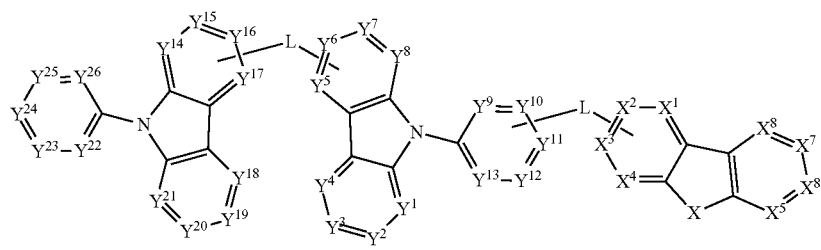
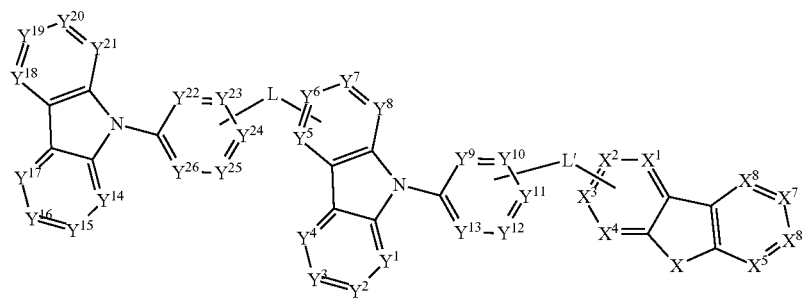
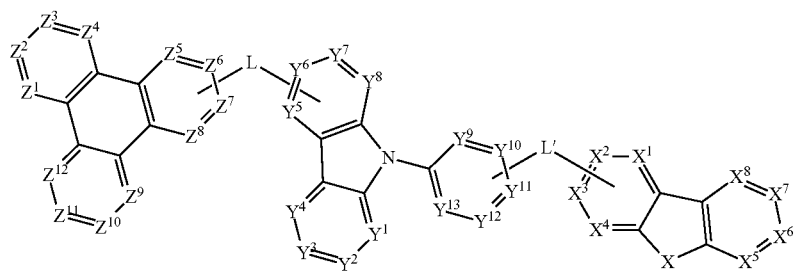
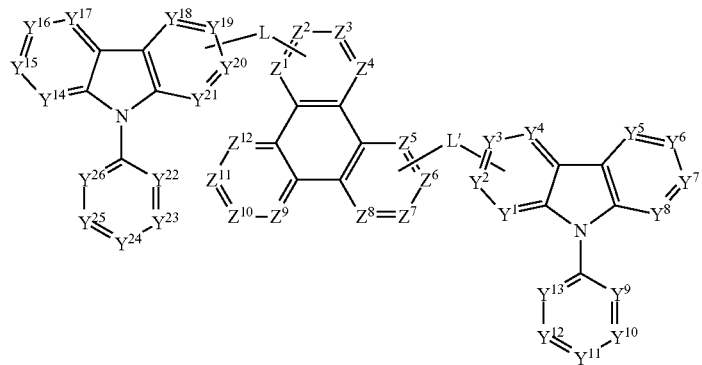

-continued
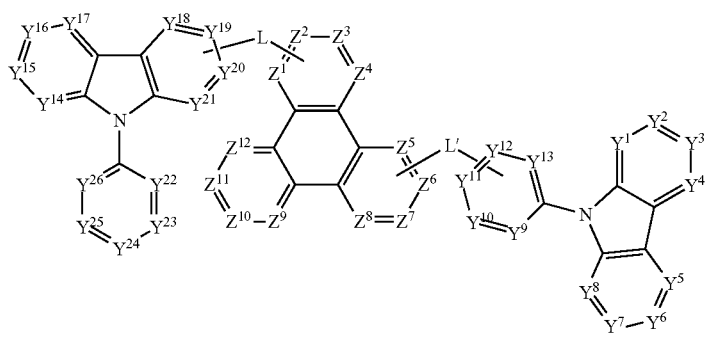
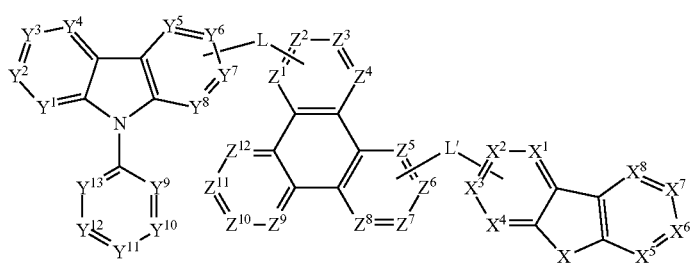
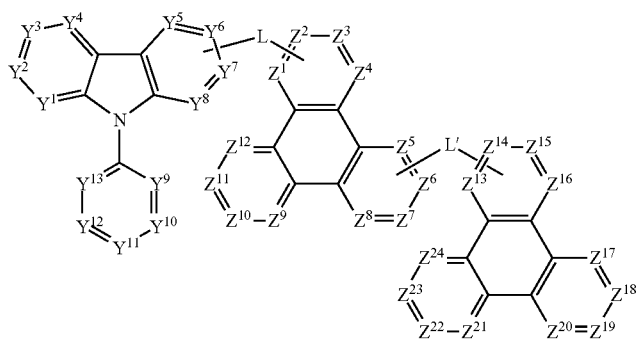
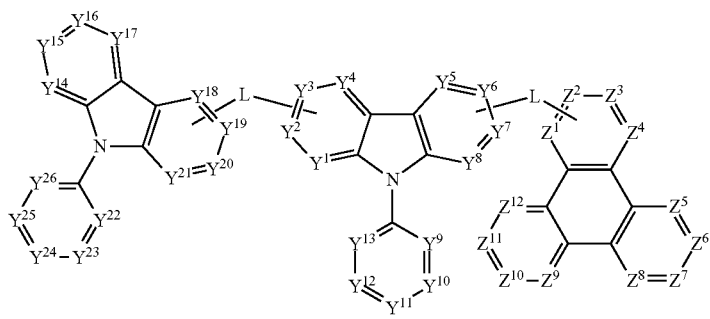
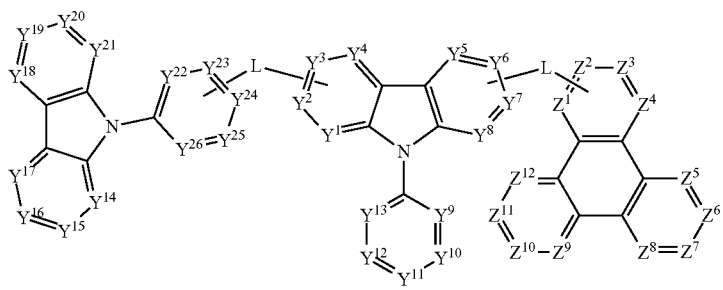

-continued
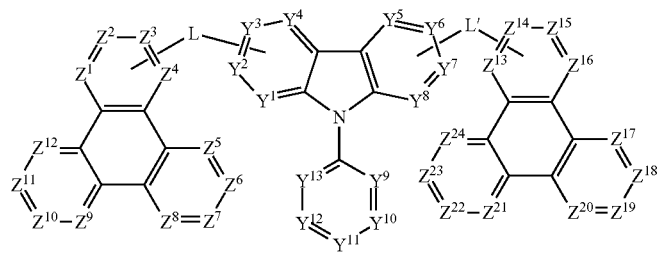
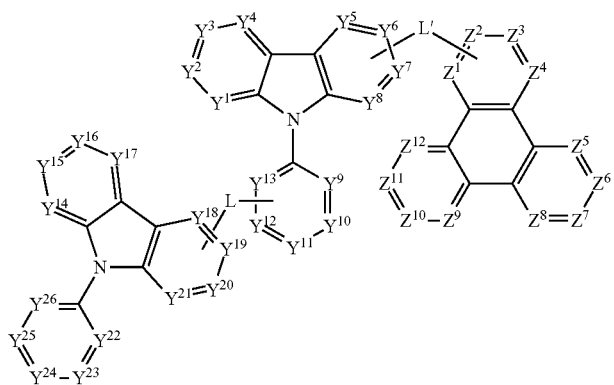
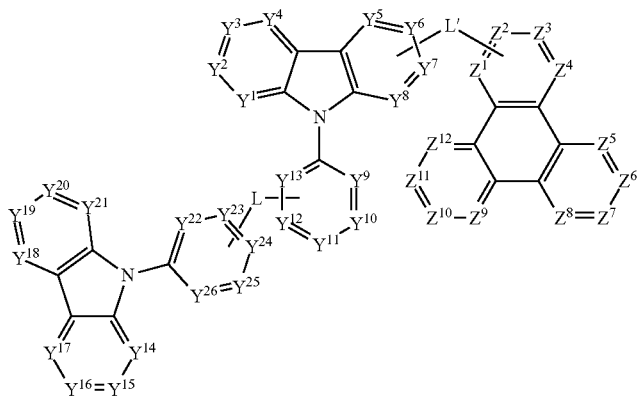
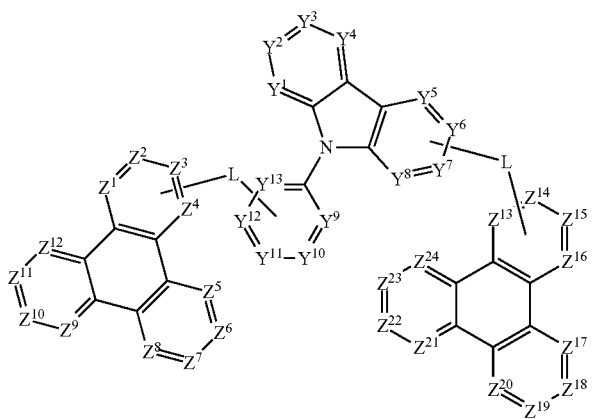

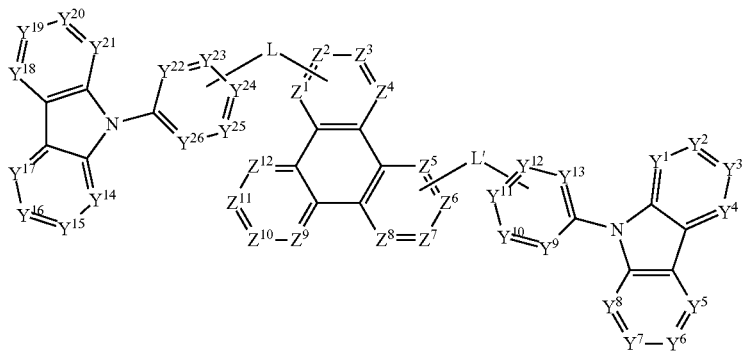
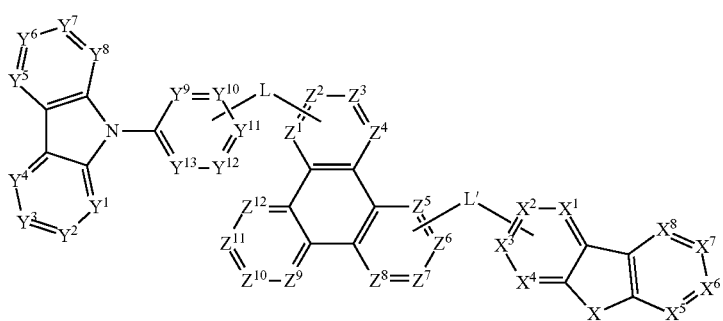
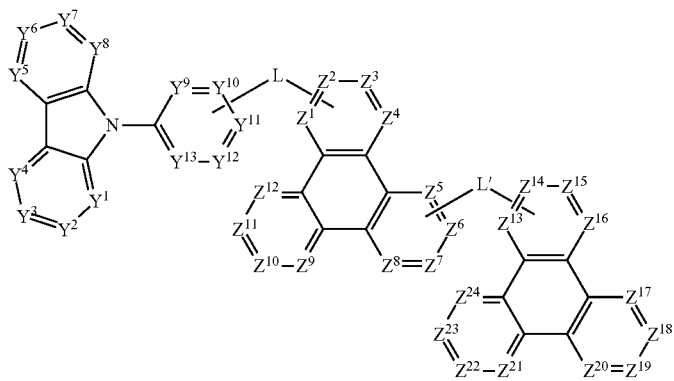
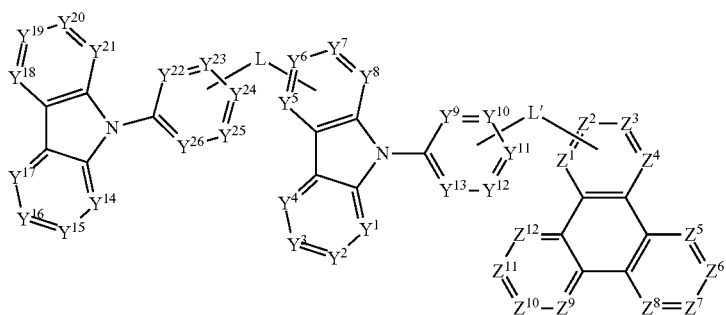
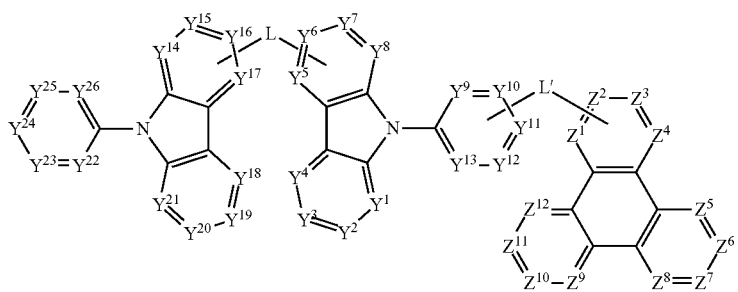

-continued

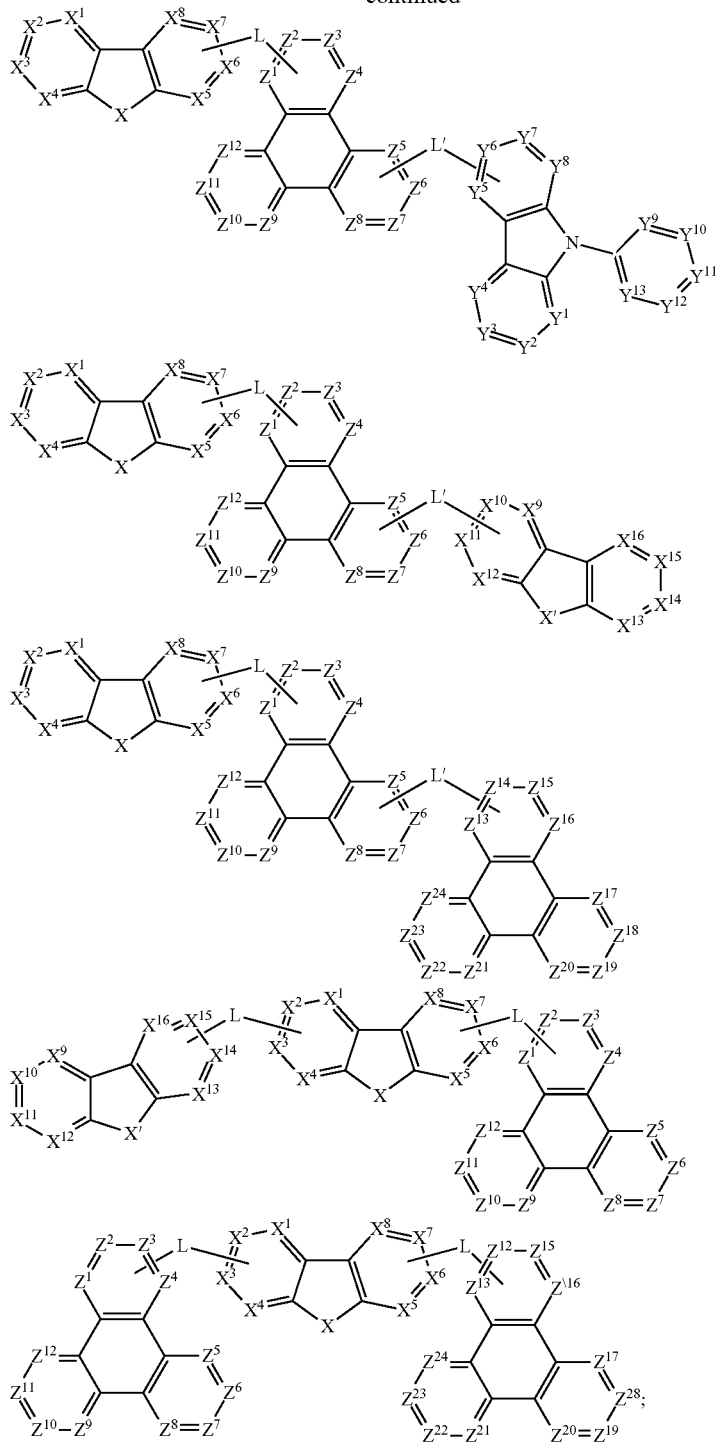

wherein X is O or S;
wherein $X^1$ to $X^{16}$, $Y^1$ to $Y^{26}$, and $Z^1$ to $Z^{24}$ are each independently selected from the group consisting of CR and N; and
wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

In some embodiments, the compound is selected from the group consisting of compound 1 to compound 459.

In some embodiments, A is dibenzothiophene, L is —$CH_2$—, and B is N-phenyl carbazole.

In some embodiments, a first device is provided. In some embodiments, the first device comprises a first organic light emitting device. In some embodiments, the first organic light emitting device comprises an anode, a cathode, and an organic layer, disposed between the anode and the cathode, comprising a compound having formula I:

A-L-B (I).

In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;
A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein the two adjacent substituents can optionally join to form a fused ring;
L is selected from the group consisting of alkyl, cycloalkyl, substituted alkyl, and substituted cycloalkyl; and
L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

The present invention also provides a formulation comprising a compound having formula I:

A-L-B (I).

In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;
A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;
L is selected from the group consisting of alkyl, cycloalkyl, substituted alkyl, and substituted cycloalkyl; and
L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
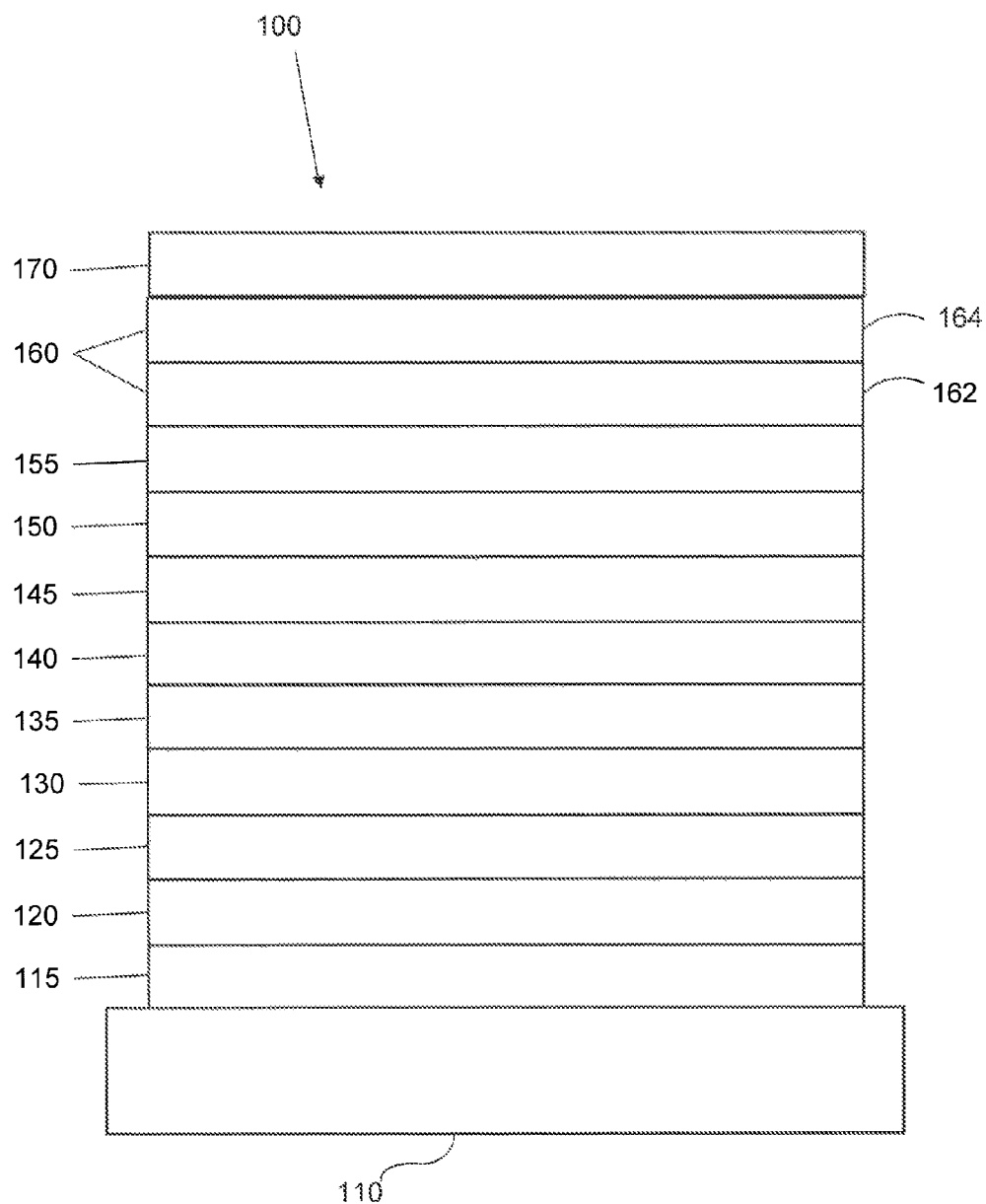
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
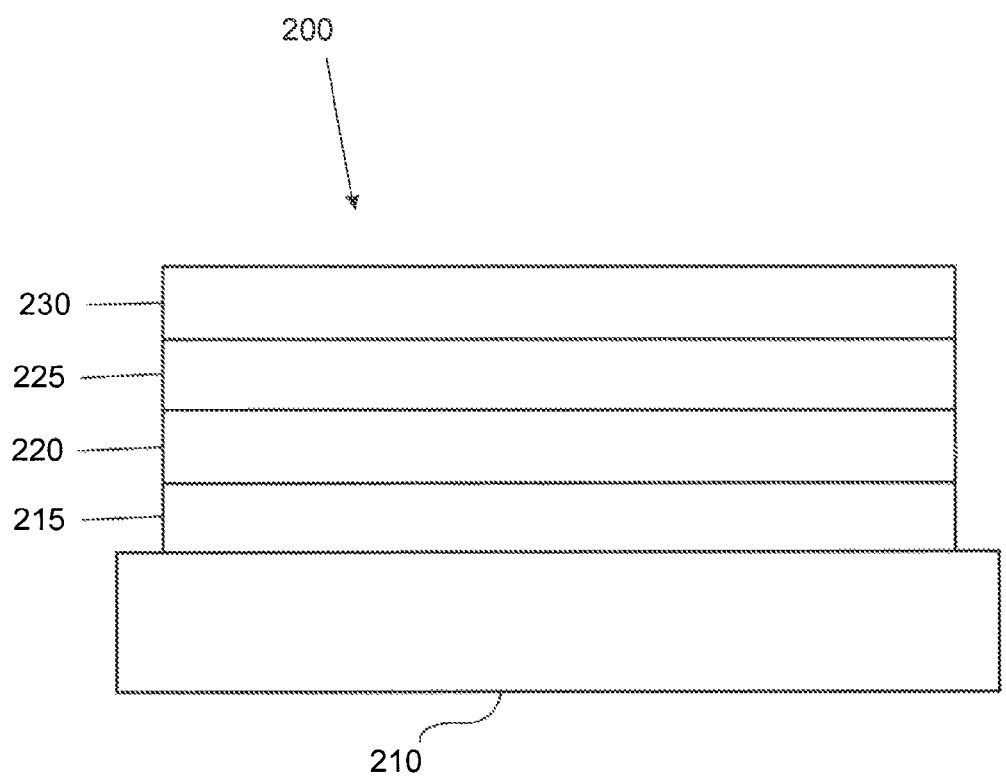
FIG. 2 shows an inverted organic light emitting device that does not have a separate electron transport layer.
Figure 3:
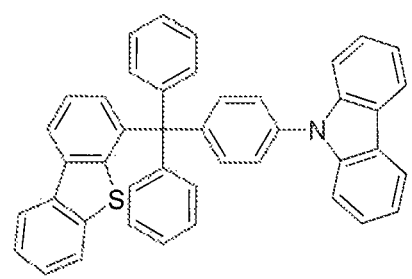
FIG. 3 shows Compound 15.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein (e.g., aza-dibenzofuran, aza-dibenzonethiophene, etc.) means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g., naphthyl, dibenzofuryl) or as if it were the whole molecule (e.g., naphthalene, dibenzofuran). As used herein, these different ways of designating a substituent or attached fragment are considered to be equivalent.

A wide variety of compounds have been developed as organic electroluminescent materials. Depending on the unique ways building blocks are connected, these compounds have different energy levels, molecular packing, and charge-transport properties, all of which heavily influence device performance. This invention discloses a new class of compounds comprising at least two different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene. Unexpectedly, phosphorescent OLED devices using the compounds of the invention as host materials demonstrate superior performance compared to the compounds reported in the literature.

A phosphorescent OLED emissive layer normally comprises both hosts and dopants. To achieve high device efficiency, the emission of the dopants should not be quenched by the hosts. Therefore, the triplet energy of the hosts should be higher than that of the dopants. Carbazole, dibenzothiophene, and triphenylene are high triplet energy host building blocks. However, upon substitution with a phenyl group, the triplet energy decreases dramatically as can be seen in TABLE 1. A red shift of triplet energy of 30 to 35 nm was observed. For deep blue phosphorescent emitters, the triplet energy of the hosts should be much higher than 450 nm, which makes carbazole, dibenzothiophene, and triphenylene hosts with phenyl spacers undesirable.

TABLE 1

Triplet energy of various host building blocks

| Structure | Triplet (nm) |
|---|---|
| N-phenyl carbazole | 415 |
| dibenzothiophene | 415 |
| triphenylene | 435 |
| 3,6-diphenyl-N-phenyl carbazole | 450 |
| 2-phenyl dibenzothiophene | 447 |
| 4-phenyl dibenzothiophene | 450 |
| | 468 |

U.S. Patent Application Publication No. 2009/0167162 discloses dibenzothiophene compounds with methylene linkages as host materials for deep blue phosphorescence. The methylene linkage breaks the conjugation of the compound and maintains the high triplet energy of dibenzothiophene, making its triplet suitable for deep blue phosphorescence. However, charge balance in the emissive layer of these hosts can be a problem. The electronic properties, especially the transport properties can be tuned by introducing other building blocks such as carbazole, triphenylene, aza-carbazole, aza-dibenzothiophene, and aza-triphenylene.

In some embodiments, a compound having formula I:

$$A-L-B \qquad (I).$$

is provided. In the compound of formula I, A and B are each different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;

A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

L is selected from the group consisting of alkyl, cycloalkyl, substituted alkyl, and substituted cycloalkyl; and L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, a compound having formula I:

$$A-L-B \qquad (I).$$

is provided. In the compound of formula I, A and B are each different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;

A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

L is selected from the group consisting of alkyl, cycloalkyl, substituted alkyl, and substituted cycloalkyl; and L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein A including optional substituents and B including optional substituents are different.

In some embodiments, if A is a benzothiophene, then B is not a benzothiophene.

In some embodiments, the compound of formula I further comprises C, wherein C is selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;

C can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

C is connected to A or B by L'; wherein L' is selected from the group consisting of alkyl, cycloalkyl, substituted alkyl, and substituted cycloalkyl; and L' can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, A and B have no further substitution.

In some embodiments, the triplet energies of A, B, and C are equal to or less than 450 nm. In further embodiments, the triplet energies of A, B, and C are equal to or less than 445 nm. In another embodiments, the triplet energies of A, B, and C are equal to or less than 440 nm. Triplet energy is determined by phosphorescence in an organic solvent glass at 77° K.

In some embodiments, C is a different selection from the group consisting of N-phenyl carbazole, dibenzofuran, dibenzothiophene, triphenylene, aza-(N-phenyl carbazole), aza-dibenzofuran, aza-dibenzothiophene, and aza-triphenylene than A and B.

In some embodiments, A, B, and C have no further substitution.

In some embodiments, no more than one of A, B, and C is aza-(N-phenyl carbazole), aza-dibenzofuran, aza-dibenzothiophene, or aza-triphenylene.

In some embodiments, A and B are each independently selected from the group consisting of N-phenyl carbazole, aza-(N-phenyl carbazole), dibenzofuran, dibenzothiophene, and triphenylene.

In some embodiments, A is selected from the group consisting of N-phenyl carbazole, dibenzofuran, dibenzothiophene, and triphenylene; and B is selected from the group consisting of aza-(N-phenyl carbazole), aza-dibenzofuran, aza-dibenzothiophene, and aza-triphenylene.

In some embodiments, L has from 1 to 24 carbon atoms.
In some embodiments, L' has from 1 to 24 carbon atoms.
In some embodiments, L is selected from the group consisting of

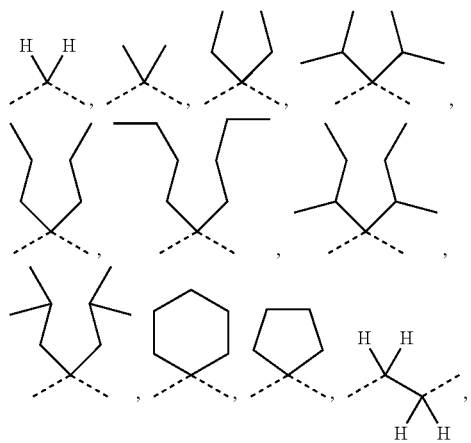

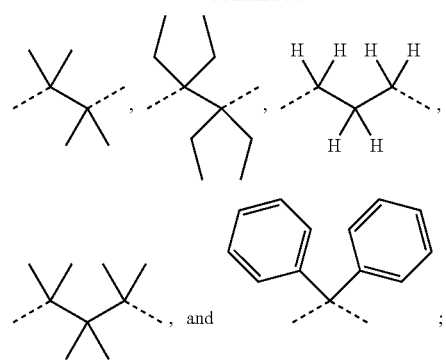

and wherein the dash lines represent a direct bond between L and A, and L and B.

In some embodiments, L' is selected from the group consisting of

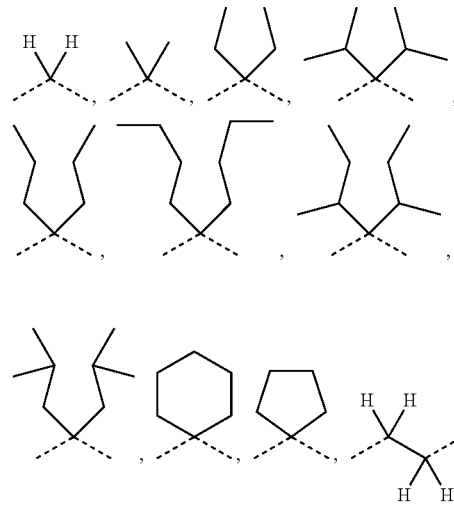

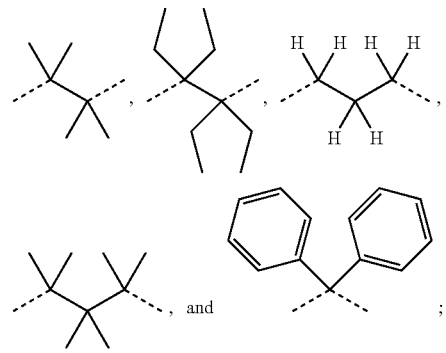

and wherein the dash lines represent a direct bond between L' and C, and L' and A or B.

In some embodiments, A or B is (9-carbazolyl)-(N-phenyl-carbazole).

In some embodiments, the aza-(N-phenyl carbazole) is selected from the group consisting of N-pyridyl carbazole, N-pyrazinyl carbazole, and N-triazinyl carbazole.

In some embodiments, the compound is selected from the group consisting of:

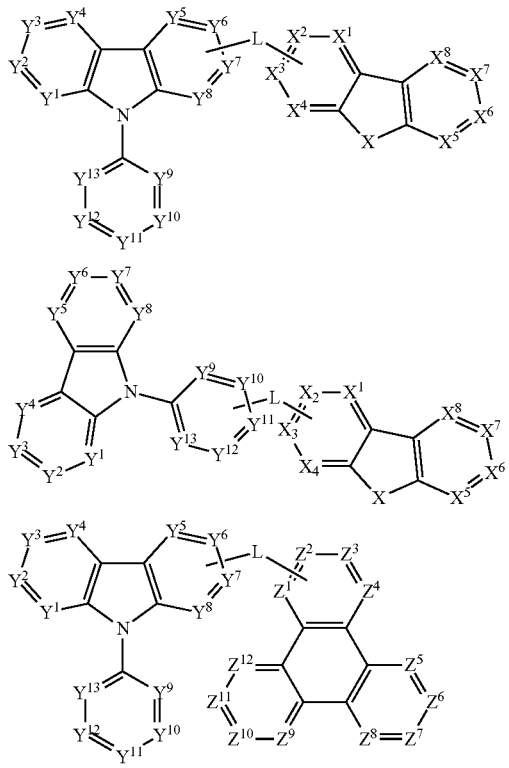

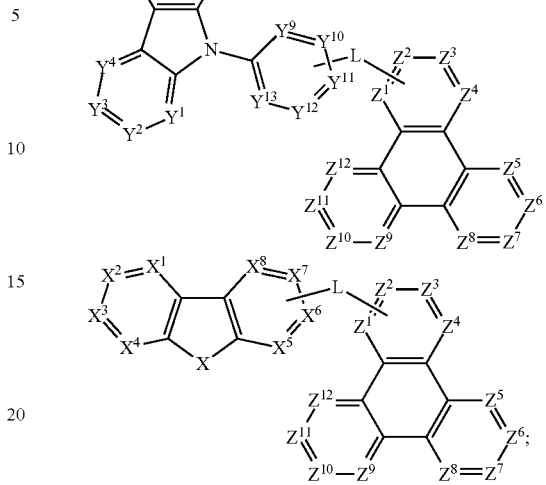

wherein X is O or S;
wherein $X^1$ to $X^8$, $Y^1$ to $Y^{13}$, and $Z^1$ to $Z^{12}$ are each independently selected from the group consisting of CR and N; and
wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

In some embodiments, the compound is selected from the group consisting of:

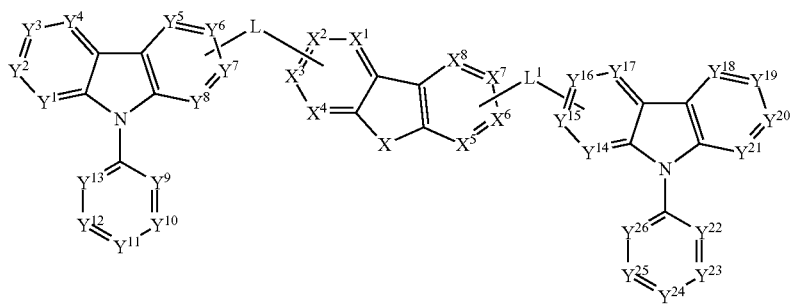

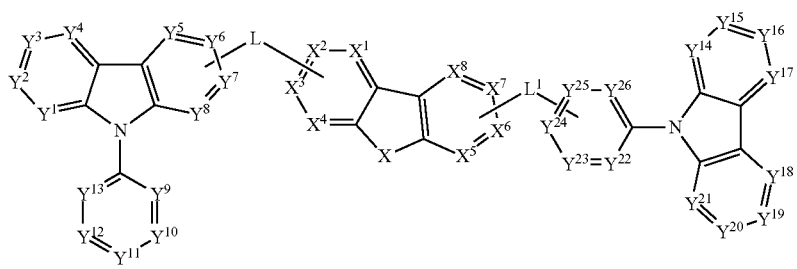

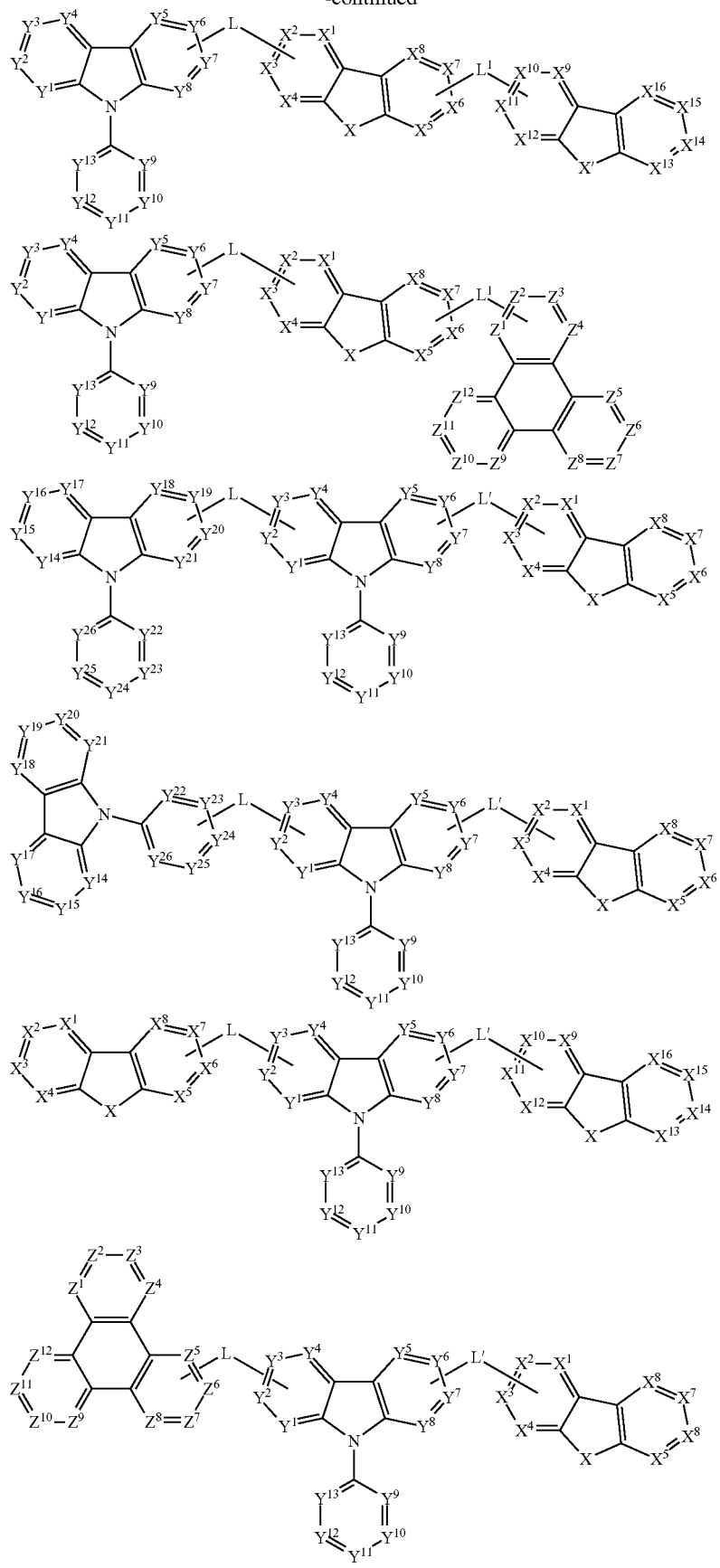

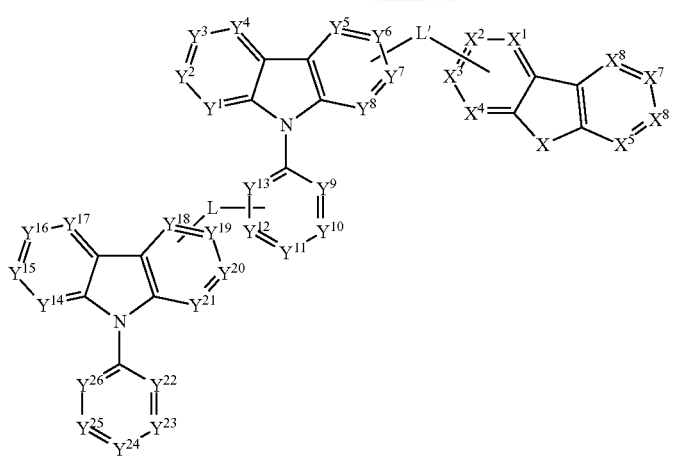
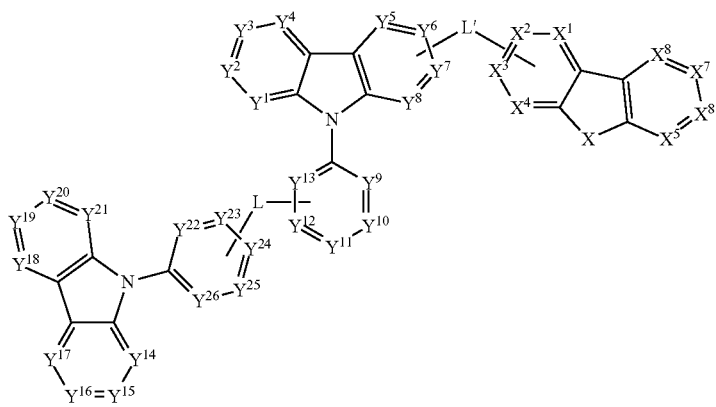
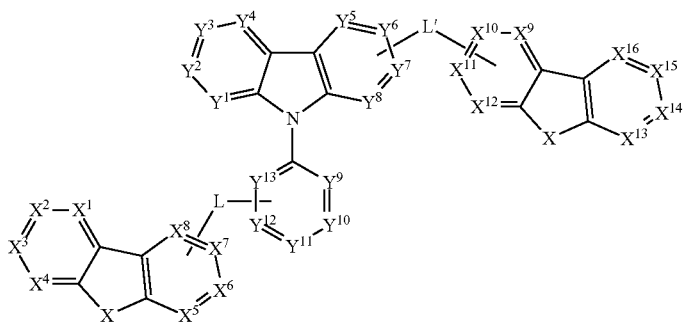
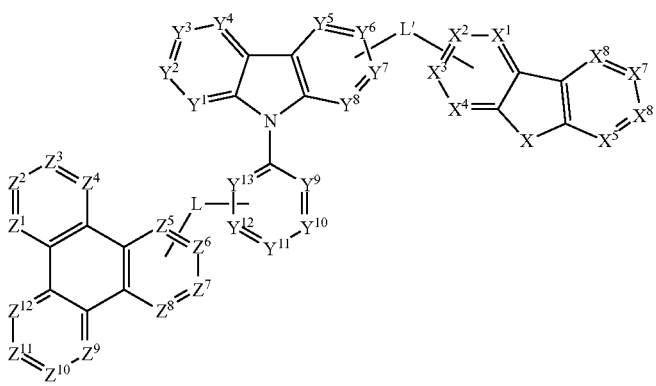

-continued
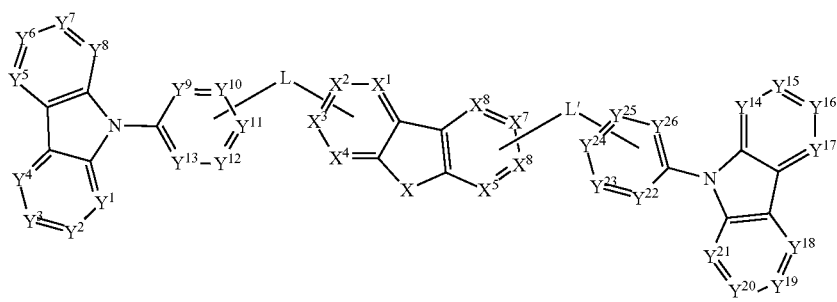
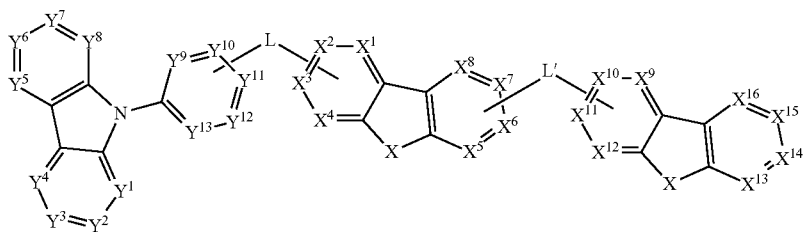
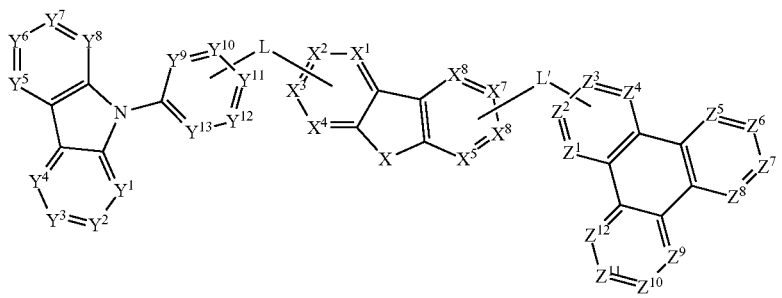
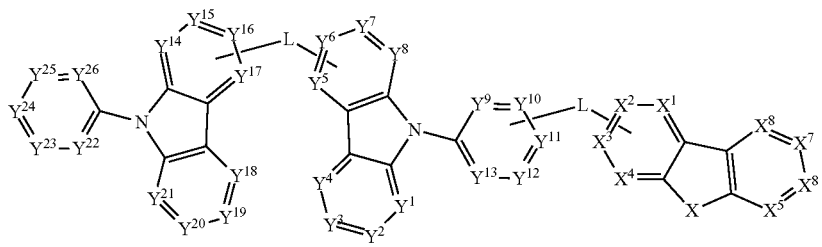
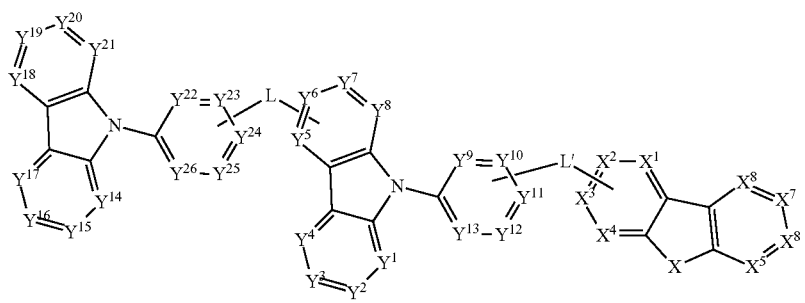
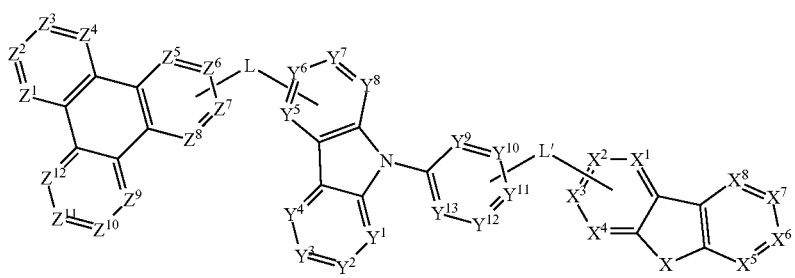

-continued
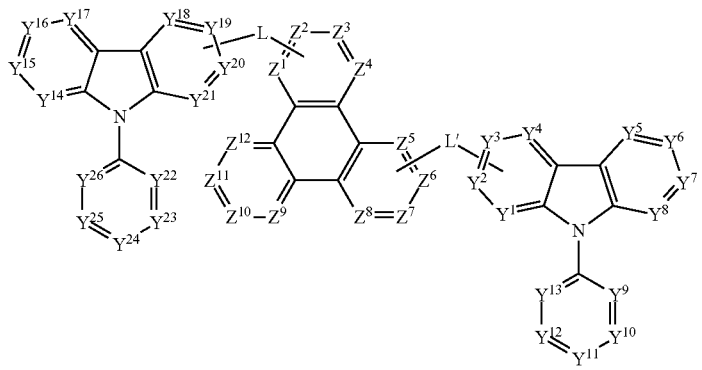
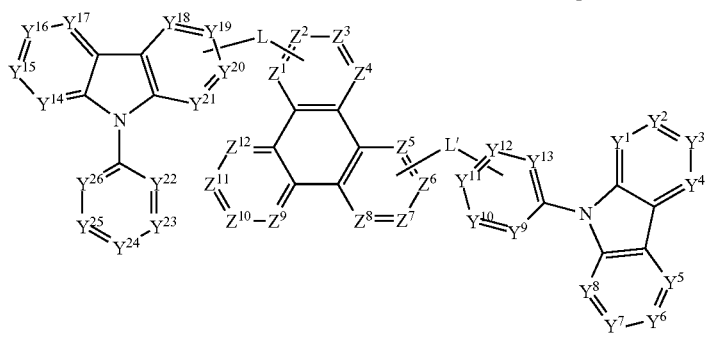
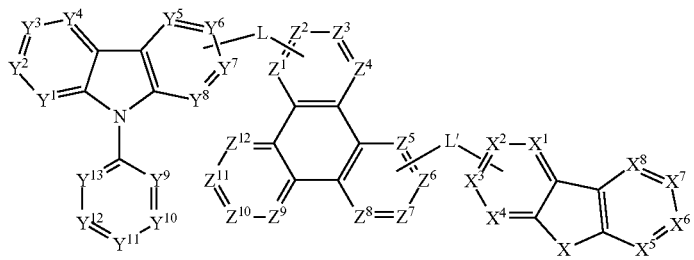
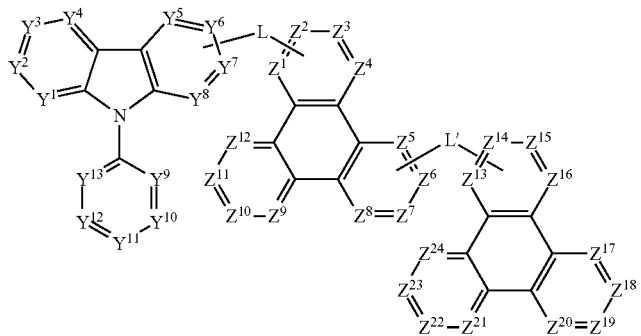
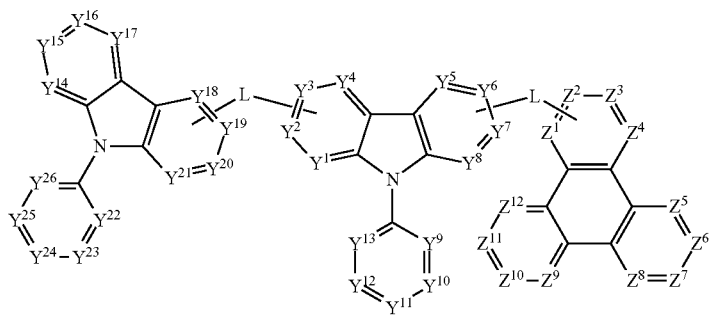

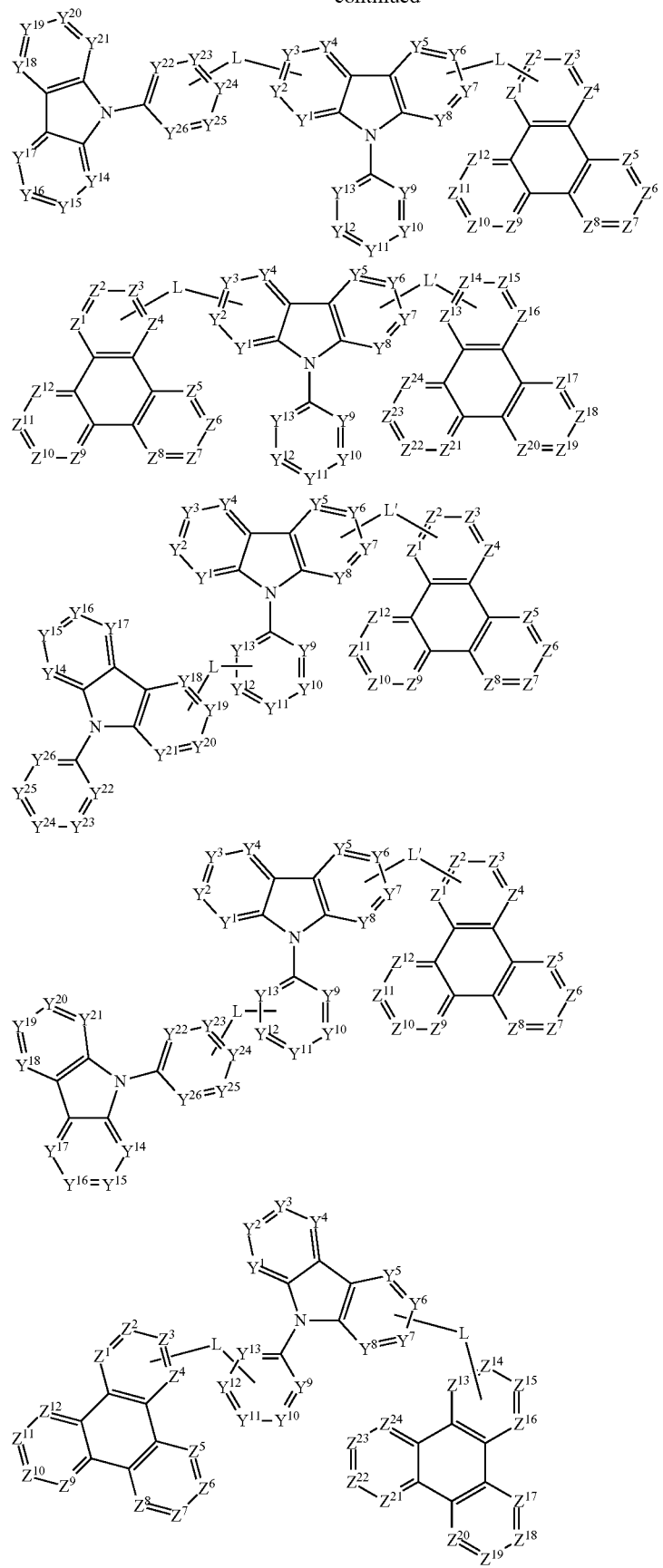

-continued
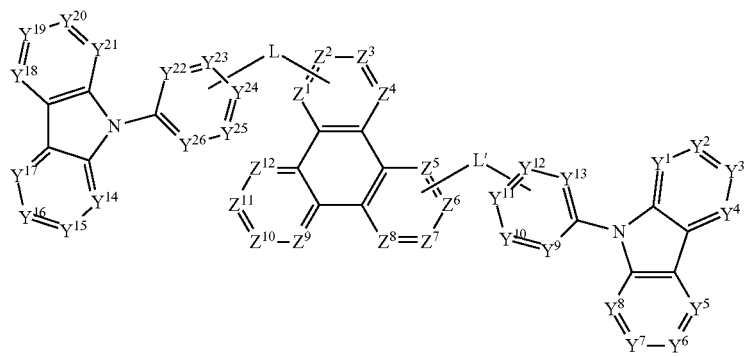
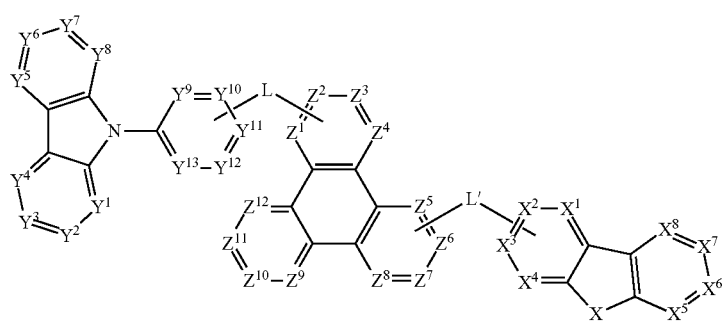
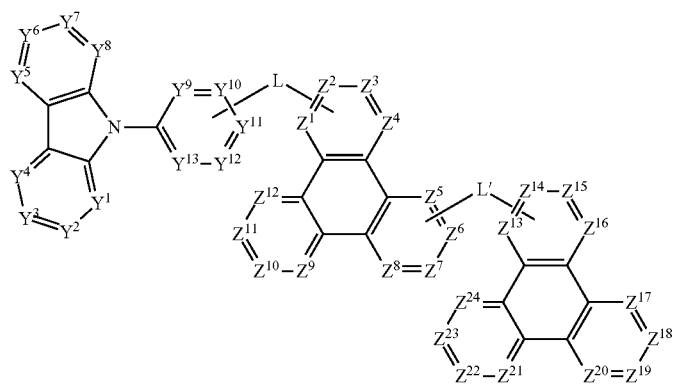
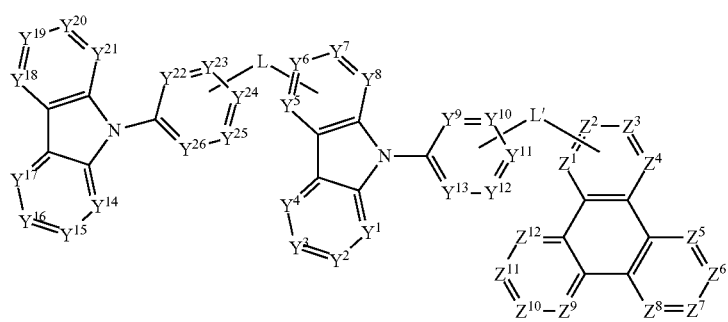
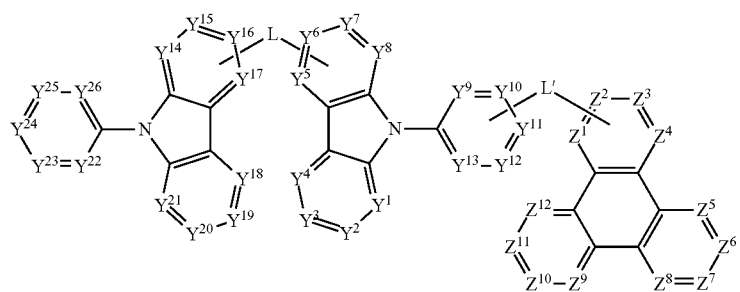

-continued

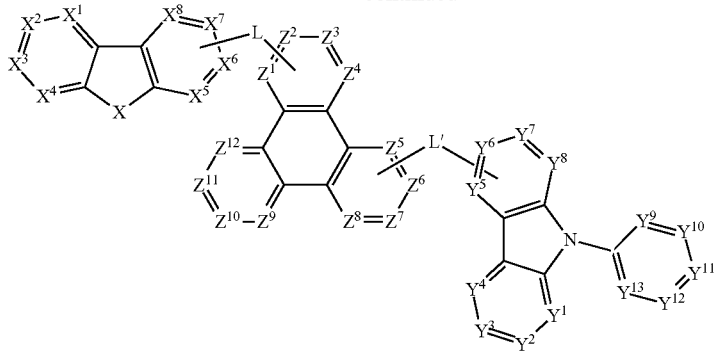

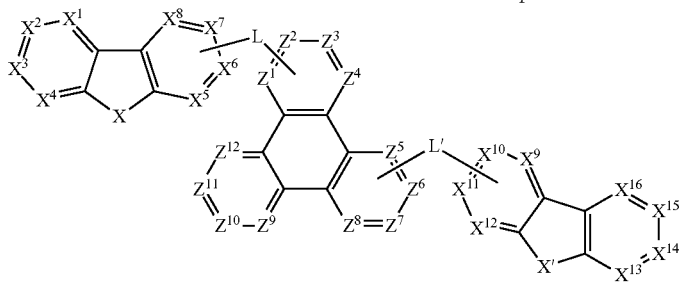

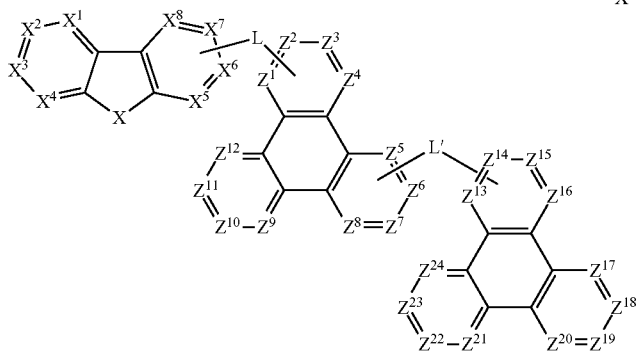

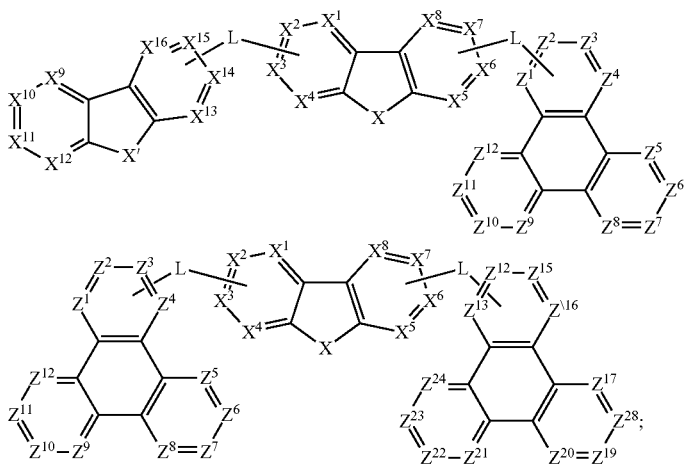

wherein X is O or S;

wherein $X^1$ to $X^{16}$, $Y^1$ to $Y^{26}$, and $Z^1$ to $Z^{24}$ are each independently selected from the group consisting of CR and N; and wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

In some embodiments, the compound is selected from the group consisting of compound 1 to compound 459 listed below:

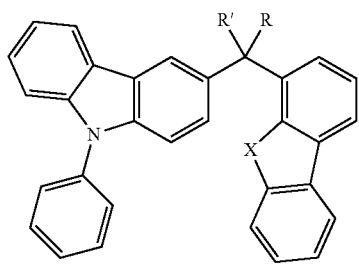
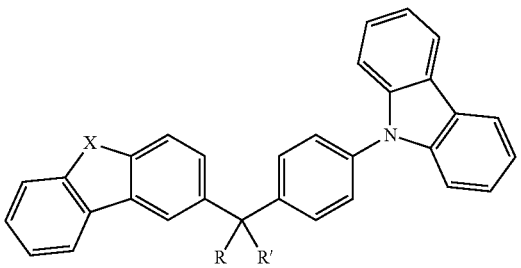

Compound 1 R = R' = H, X = S
Compound 2 R = R' = CH₃, X = S
Compound 3 R = R' = Ph, X = S
Compound 4 R = R' = H, X = O
Compound 5 R = R' = CH₃, X = O
Compound 6 R = R' = Ph, X = O Compound 7 R = R' = H, X = S
Compound 8 R = R' = CH₃, X = S
Compound 9 R = R' = Ph, X = S
Compound 10 R = R' = H, X = O
Compound 11 R = R' = CH₃, X = O
Compound 12 R = R' = Ph, X = O

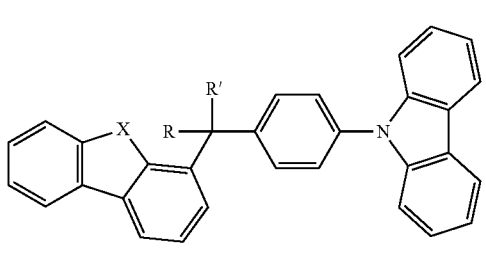
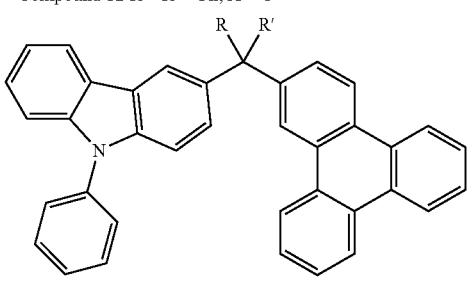

Compound 13 R = R' = H, X = S
Compound 14 R = R' = CH₃, X = S
Compound 15 R = R' = Ph, X = S
Compound 16 R = R' = H, X = O
Compound 17 R = R' = CH₃, X = O
Compound 18 R = R' = Ph, X = O Compound 19 R = R' = H
Compound 20 R = R' = CH₃
Compound 21 R = R' = Ph

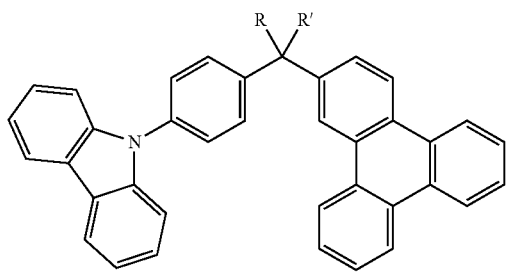
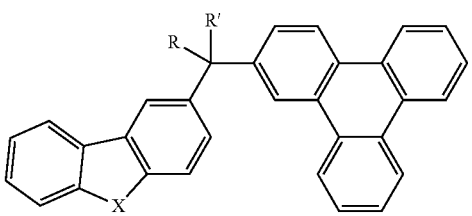

Compound 22 R = R' = H
Compound 23 R = R' = CH₃
Compound 24 R = R' = Ph

Compound 25 R = R' = H, X = S
Compound 26 R = R' = CH₃, X = S
Compound 27 R = R' = Ph, X = S
Compound 28 R = R' = H, X = O
Compound 29 R = R' = CH₃, X = O
Compound 30 R = R' = Ph, X = O

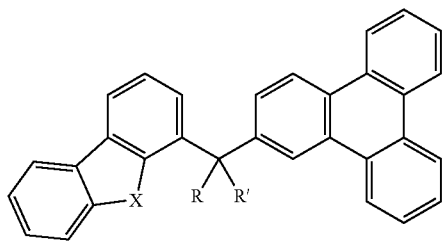

Compound 31 R = R' = H, X = S
Compound 32 R = R' = CH₃, X = S
Compound 33 R = R' = Ph, X = S
Compound 34 R = R' = H, X = O
Compound 35 R = R' = CH₃, X = O
Compound 36 R = R' = Ph, X = O -continued

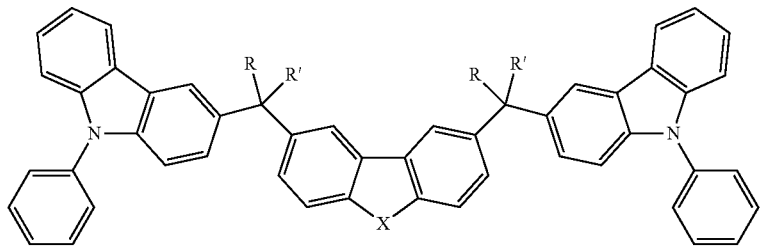

Compound 37 R = R' = H, X = S
Compound 38 R = R' = CH₃, X = S
Compound 39 R = R' = Ph, X = S
Compound 40 R = R' = H, X = O
Compound 41 R = R' = CH₃, X = O
Compound 42 R = R' = Ph, X = O

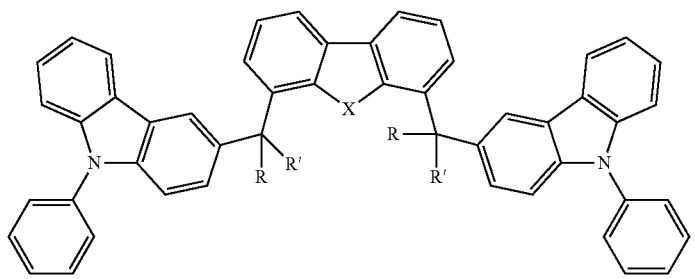

Compound 43 R = R' = H, X = S
Compound 44 R = R' = CH₃, X = S
Compound 45 R = R' = Ph, X = S
Compound 46 R = R' = H, X = O
Compound 47 R = R' = CH₃, X = O
Compound 48 R = R' = Ph, X = O

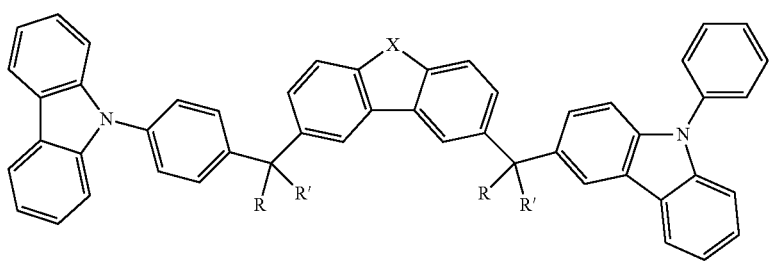

Compound 49 R = R' = H, X = S
Compound 50 R = R' = CH₃, X = S
Compound 51 R = R' = Ph, X = S
Compound 52 R = R' = H, X = O
Compound 53 R = R' = CH₃, X = O
Compound 54 R = R' = Ph, X = O

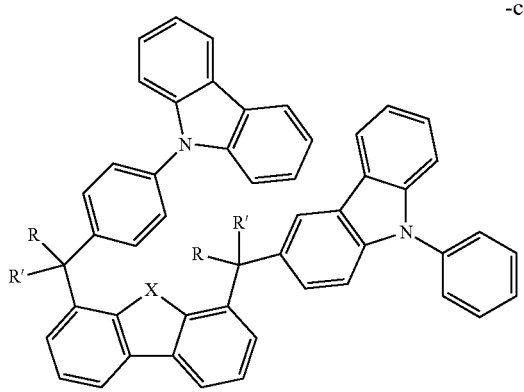

Compound 55 R = R' = H, X = S
Compound 56 R = R' = CH$_3$, X = S
Compound 57 R = R' = Ph, X = S
Compound 58 R = R' = H, X = O
Compound 59 R = R' = CH$_3$, X = O
Compound 60 R = R' = Ph, X = O

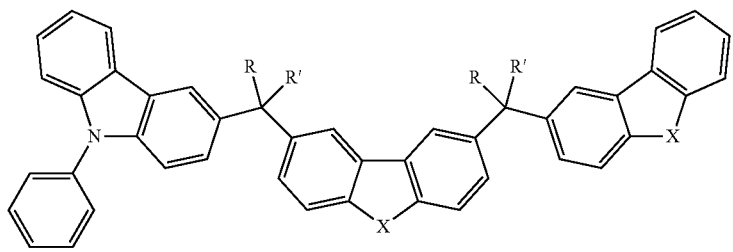

Compound 61 R = R' = H, X = S
Compound 62 R = R' = CH$_3$, X = S
Compound 63 R = R' = Ph, X = S
Compound 64 R = R' = H, X = O
Compound 65 R = R' = CH$_3$, X = O
Compound 66 R = R' = Ph, X = O

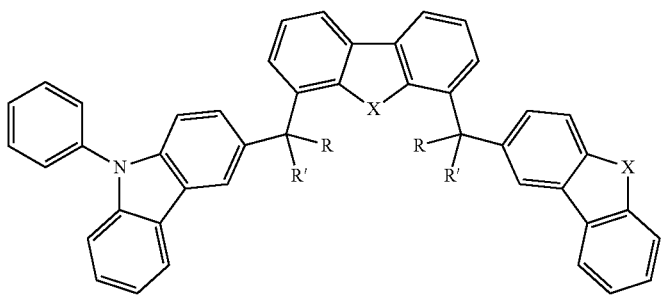

Compound 67 R = R' = H, X = S
Compound 68 R = R' = CH$_3$, X = S
Compound 69 R = R' = Ph, X = S
Compound 70 R = R' = H, X = O
Compound 71 R = R' = CH$_3$, X = O
Compound 72 R = R' = Ph, X = O -continued

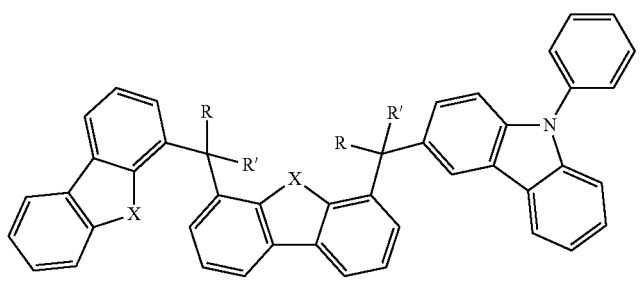

Compound 73 R = R' = H, X = S
Compound 74 R = R' = CH₃, X = S
Compound 75 R = R' = Ph, X = S
Compound 76 R = R' = H, X = O
Compound 77 R = R' = CH₃, X = O
Compound 78 R = R' = Ph, X = O

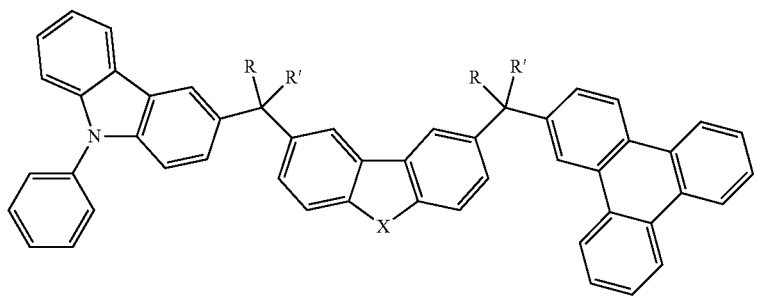

Compound 79 R = R' = H, X = S
Compound 80 R = R' = CH₃, X = S
Compound 81 R = R' = Ph, X = S
Compound 82 R = R' = H, X = O
Compound 83 R = R' = CH₃, X = O
Compound 84 R = R' = Ph, X = O

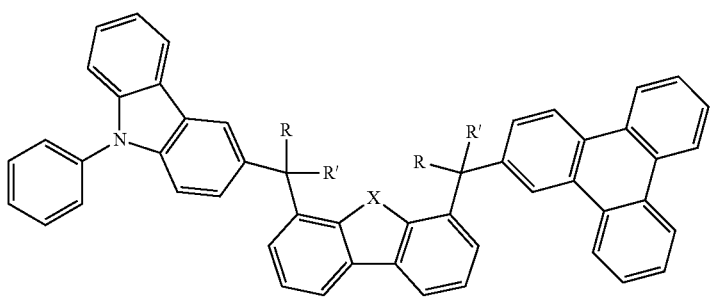

Compound 85 R = R' = H, X = S
Compound 86 R = R' = CH₃, X = S
Compound 87 R = R' = Ph, X = S
Compound 88 R = R' = H, X = O
Compound 89 R = R' = CH₃, X = O
Compound 90 R = R' = Ph, X = O -continued

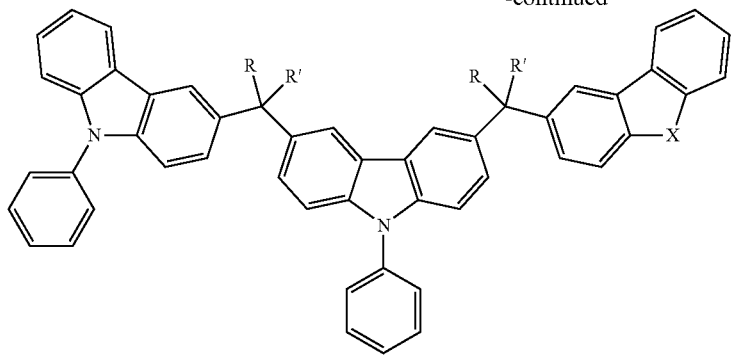

Compound 91 R = R' = H, X = S
Compound 92 R = R' = CH₃, X = S
Compound 93 R = R' = Ph, X = S
Compound 94 R = R' = H, X = O
Compound 95 R = R' = CH₃, X = O
Compound 96 R = R' = Ph, X = O

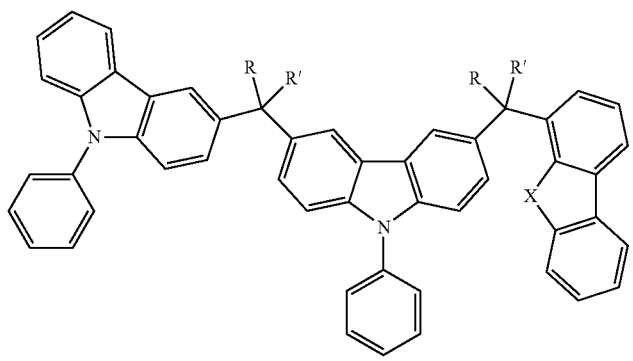

Compound 97 R = R' = H, X = S
Compound 98 R = R' = CH₃, X = S
Compound 99 R = R' = Ph, X = S
Compound 100 R = R' = H, X = O
Compound 101 R = R' = CH₃, X = O
Compound 102 R = R' = Ph, X = O

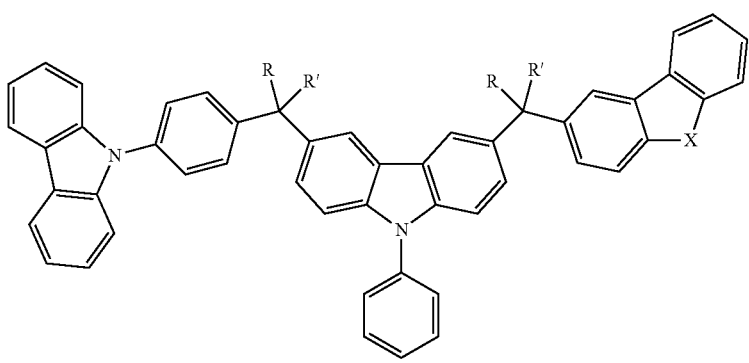

Compound 103 R = R' = H, X = S
Compound 104 R = R' = CH₃, X = S
Compound 105 R = R' = Ph, X = S
Compound 106 R = R' = H, X = O
Compound 107 R = R' = CH₃, X = O
Compound 108 R = R' = Ph, X = O

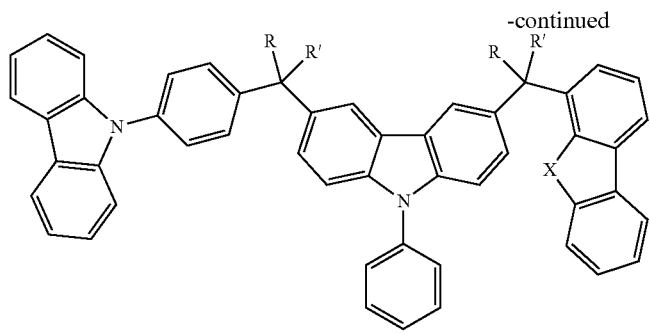

Compound 109 R = R' = H, X = S
Compound 110 R = R' = CH₃, X = S
Compound 111 R = R' = Ph, X = S
Compound 112 R = R' = H, X = O
Compound 113 R = R' = CH₃, X = O
Compound 114 R = R' = Ph, X = O

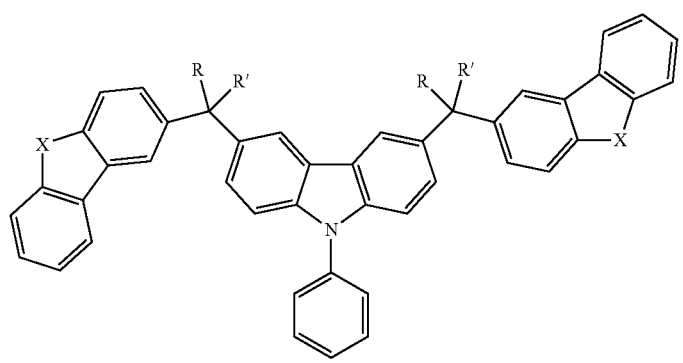

Compound 115 R = R' = H, X = S
Compound 116 R = R' = CH₃, X = S
Compound 117 R = R' = Ph, X = S
Compound 118 R = R' = H, X = O
Compound 119 R = R' = CH₃, X = O
Compound 120 R = R' = Ph, X = O

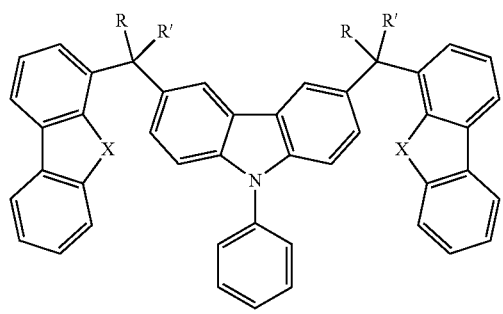

Compound 121 R = R' = H, X = S
Compound 122 R = R' = CH₃, X = S
Compound 123 R = R' = Ph, X = S
Compound 124 R = R' = H, X = O
Compound 125 R = R' = CH₃, X = O
Compound 126 R = R' = Ph, X = O -continued

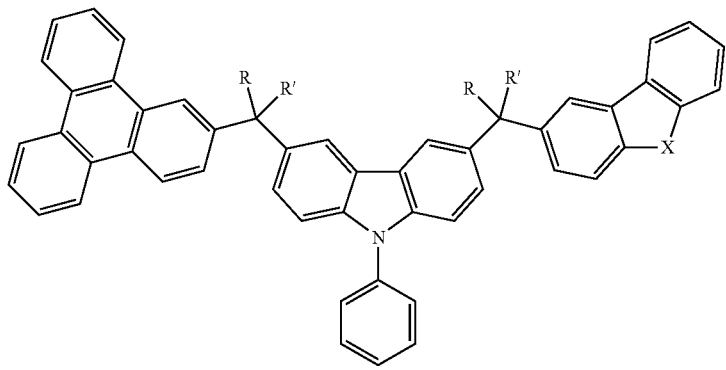

Compound 127 R = R' = H, X = S
Compound 128 R = R' = CH₃, X = S
Compound 129 R = R' = Ph, X = S
Compound 130 R = R' = H, X = O
Compound 131 R = R' = CH₃, X = O
Compound 132 R = R' = Ph, X = O

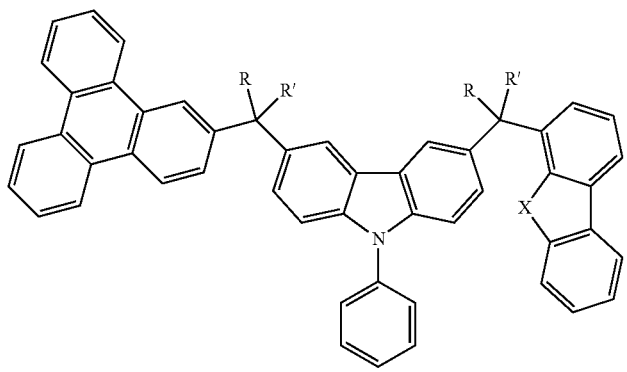

Compound 133 R = R' = H, X = S
Compound 134 R = R' = CH₃, X = S
Compound 135 R = R' = Ph, X = S
Compound 136 R = R' = H, X = O
Compound 137 R = R' = CH₃, X = O
Compound 138 R = R' = Ph, X = O

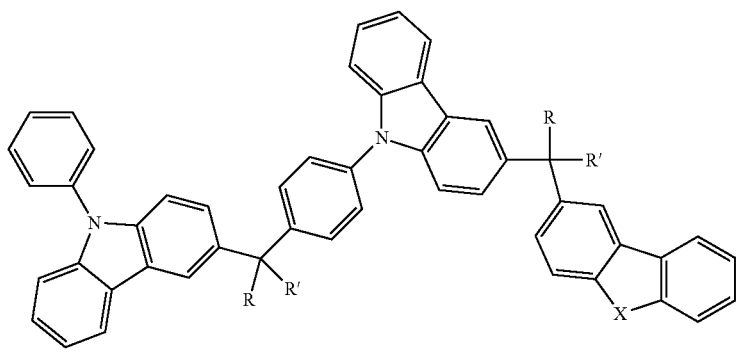

Compound 139 R = R' = H, X = S
Compound 140 R = R' = CH₃, X = S
Compound 141 R = R' = Ph, X = S
Compound 142 R = R' = H, X = O
Compound 143 R = R' = CH₃, X = O
Compound 144 R = R' = Ph, X = O

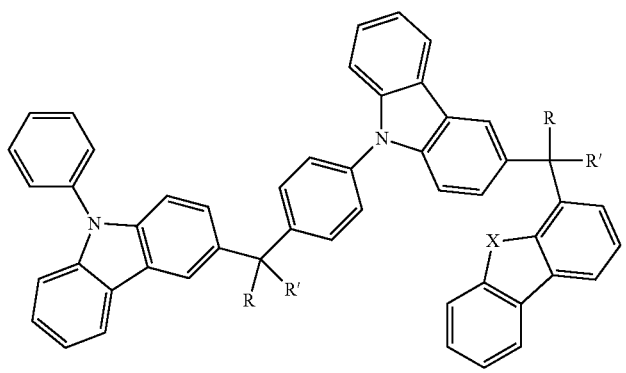

Compound 145 R = R' = H, X = S
Compound 146 R = R' = CH₃, X = S
Compound 147 R = R' = Ph, X = S
Compound 148 R = R' = H, X = O
Compound 149 R = R' = CH₃, X = O
Compound 150 R = R' = Ph, X = O

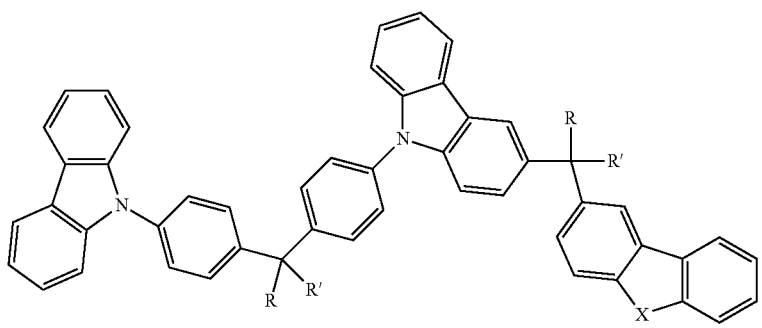

Compound 151 R = R' = H, X = S
Compound 152 R = R' = CH₃, X = S
Compound 153 R = R' = Ph, X = S
Compound 154 R = R' = H, X = O
Compound 155 R = R' = CH₃, X = O
Compound 156 R = R' = Ph, X = O

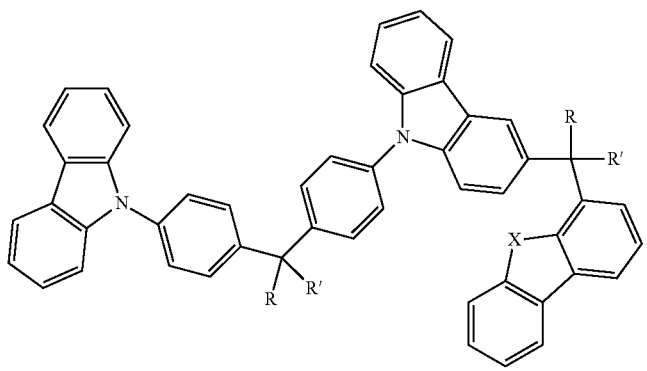

Compound 157 R = R' = H, X = S
Compound 158 R = R' = CH₃, X = S
Compound 159 R = R' = Ph, X = S
Compound 160 R = R' = H, X = O
Compound 161 R = R' = CH₃, X = O
Compound 162 R = R' = Ph, X = O -continued

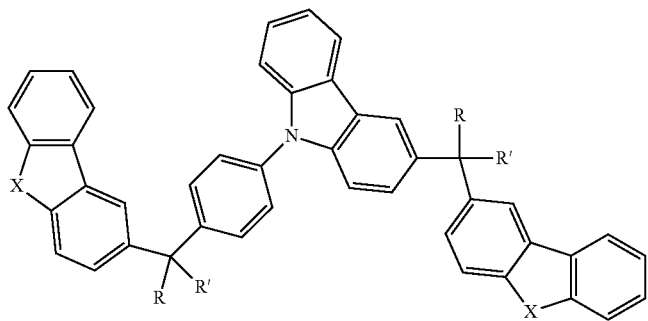

Compound 163 R = R' = H, X = S
Compound 164 R = R' = CH₃, X = S
Compound 165 R = R' = Ph, X = S
Compound 166 R = R' = H, X = O
Compound 167 R = R' = CH₃, X = O
Compound 168 R = R' = Ph, X = O

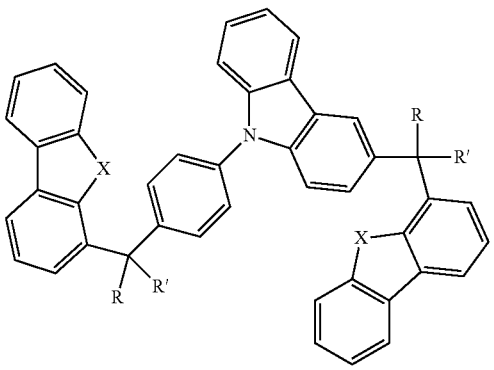

Compound 169 R = R' = H, X = S
Compound 170 R = R' = CH₃, X = S
Compound 171 R = R' = Ph, X = S
Compound 172 R = R' = H, X = O
Compound 173 R = R' = CH₃, X = O
Compound 174 R = R' = Ph, X = O

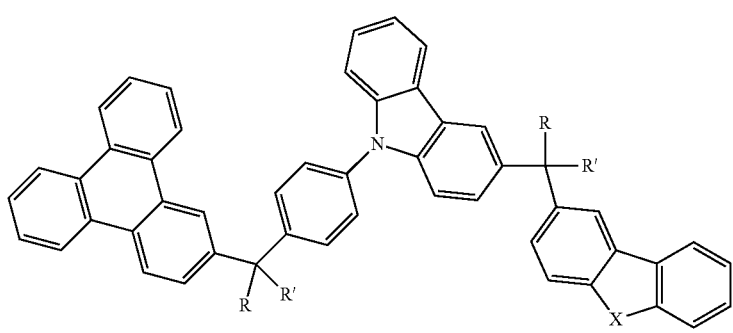

Compound 175 R = R' = H, X = S
Compound 176 R = R' = CH₃, X = S
Compound 177 R = R' = Ph, X = S
Compound 178 R = R' = H, X = O
Compound 179 R = R' = CH₃, X = O
Compound 180 R = R' = Ph, X = O

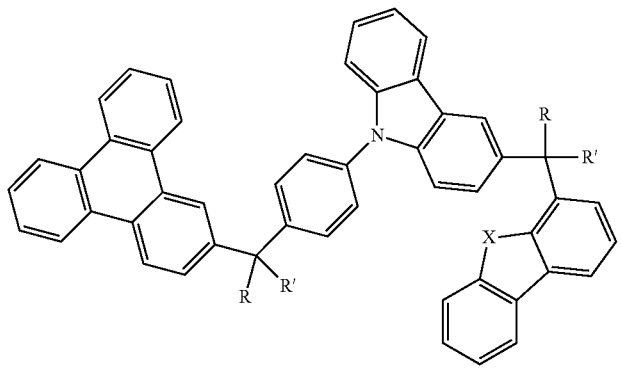

Compound 181 R = R' = H, X = S
Compound 182 R = R' = CH₃, X = S
Compound 183 R = R' = Ph, X = S
Compound 184 R = R' = H, X = O
Compound 185 R = R' = CH₃, X = O
Compound 186 R = R' = Ph, X = O

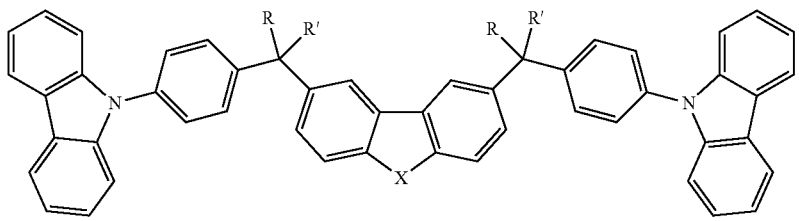

Compound 187 R = R' = H, X = S
Compound 188 R = R' = CH₃, X = S
Compound 189 R = R' = Ph, X = S
Compound 190 R = R' = H, X = O
Compound 191 R = R' = CH₃, X = O
Compound 192 R = R' = Ph, X = O

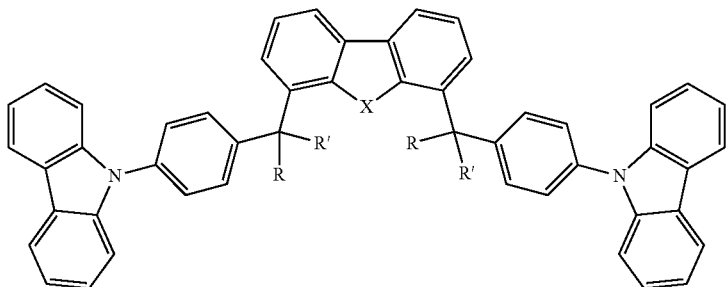

Compound 193 R = R' = H, X = S
Compound 194 R = R' = CH₃, X = S
Compound 195 R = R' = Ph, X = S
Compound 196 R = R' = H, X = O
Compound 197 R = R' = CH₃, X = O
Compound 198 R = R' = Ph, X = O

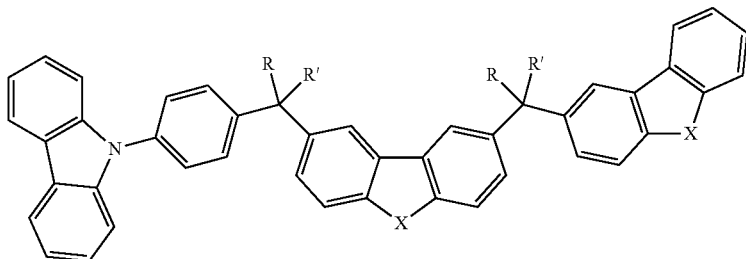

Compound 199 R = R' = H, X = S
Compound 200 R = R' = CH₃, X = S
Compound 201 R = R' = Ph, X = S
Compound 202 R = R' = H, X = O
Compound 203 R = R' = CH₃, X = O
Compound 204 R = R' = Ph, X = O

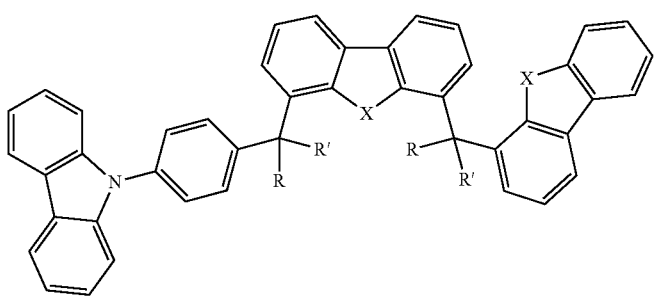

Compound 205 R = R' = H, X = S
Compound 206 R = R' = CH₃, X = S
Compound 207 R = R' = Ph, X = S
Compound 208 R = R' = H, X = O
Compound 209 R = R' = CH₃, X = O
Compound 210 R = R' = Ph, X = O

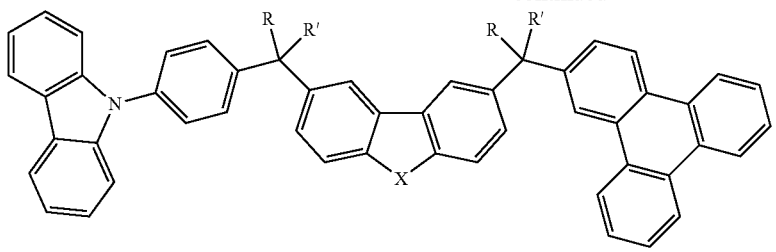

Compound 211 R = R' = H, X = S
Compound 212 R = R' = CH₃, X = S
Compound 213 R = R' = Ph, X = S
Compound 214 R = R' = H, X = O
Compound 215 R = R' = CH₃, X = O
Compound 216 R = R' = Ph, X = O

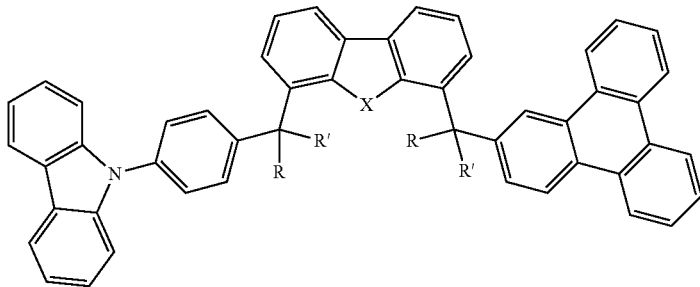

Compound 217 R = R' = H, X = S
Compound 218 R = R' = CH₃, X = S
Compound 219 R = R' = Ph, X = S
Compound 220 R = R' = H, X = O
Compound 221 R = R' = CH₃, X = O
Compound 222 R = R' = Ph, X = O

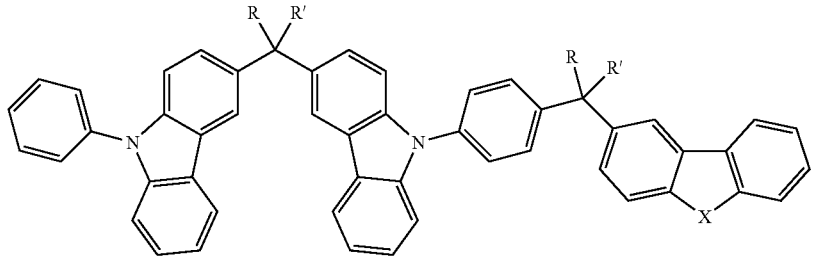

Compound 223 R = R' = H, X = S
Compound 224 R = R' = CH₃, X = S
Compound 225 R = R' = Ph, X = S
Compound 226 R = R' = H, X = O
Compound 227 R = R' = CH₃, X = O
Compound 228 R = R' = Ph, X = O

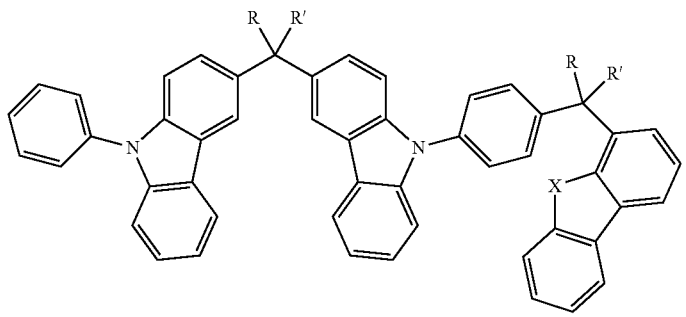

Compound 229 R = R' = H, X = S
Compound 230 R = R' = CH₃, X = S
Compound 231 R = R' = Ph, X = S
Compound 232 R = R' = H, X = O
Compound 233 R = R' = CH₃, X = O
Compound 234 R = R' = Ph, X = O -continued

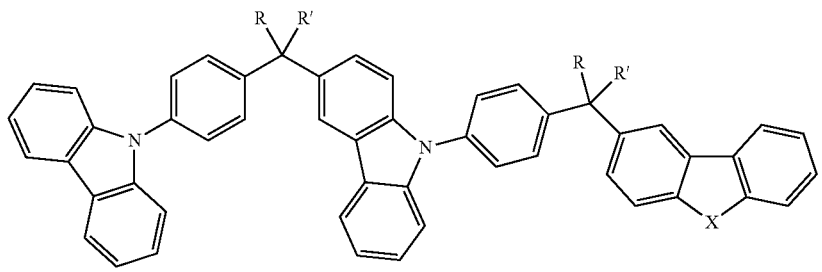

Compound 235 R = R' = H, X = S
Compound 236 R = R' = CH$_3$, X = S
Compound 237 R = R' = Ph, X = S
Compound 238 R = R' = H, X = O
Compound 239 R = R' = CH$_3$, X = O
Compound 240 R = R' = Ph, X = O

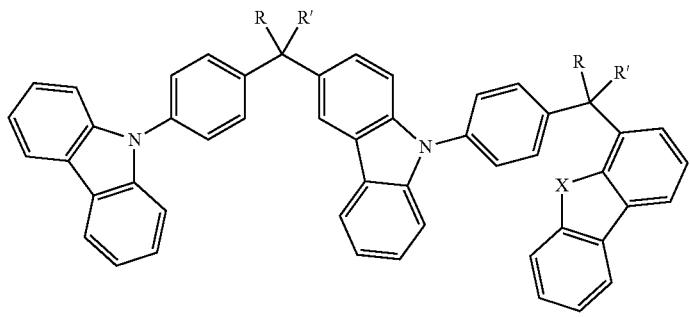

Compound 241 R = R' = H, X = S
Compound 242 R = R' = CH$_3$, X = S
Compound 243 R = R' = Ph, X = S
Compound 244 R = R' = H, X = O
Compound 245 R = R' = CH$_3$, X = O
Compound 246 R = R' = Ph, X = O

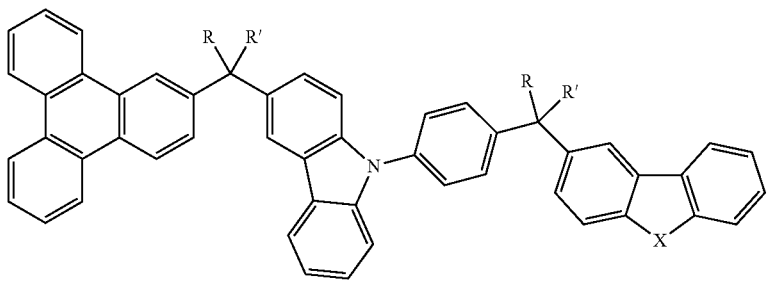

Compound 247 R = R' = H, X = S
Compound 248 R = R' = CH$_3$, X = S
Compound 249 R = R' = Ph, X = S
Compound 250 R = R' = H, X = O
Compound 251 R = R' = CH$_3$, X = O
Compound 252 R = R' = Ph, X = O

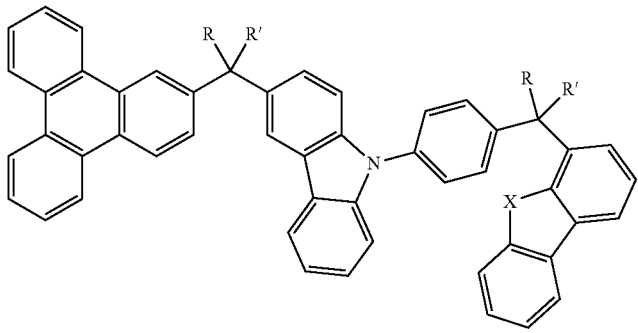

Compound 253 R = R' = H, X = S
Compound 254 R = R' = CH₃, X = S
Compound 255 R = R' = Ph, X = S
Compound 256 R = R' = H, X = O
Compound 257 R = R' = CH₃, X = O
Compound 258 R = R' = Ph, X = O

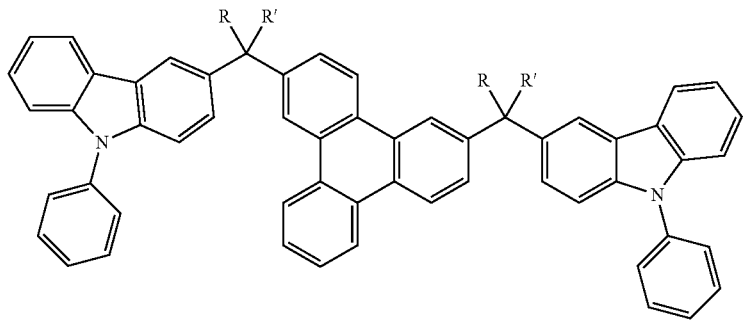

Compound 259 R = R' = H
Compound 260 R = R' = CH₃
Compound 261 R = R' = Ph

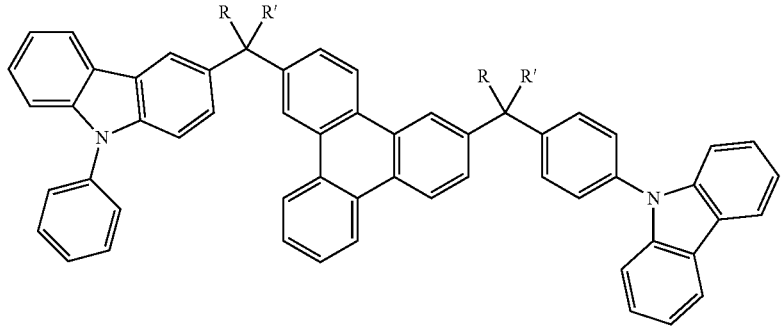

Compound 262 R = R' = H
Compound 263 R = R' = CH₃
Compound 264 R = R' = Ph

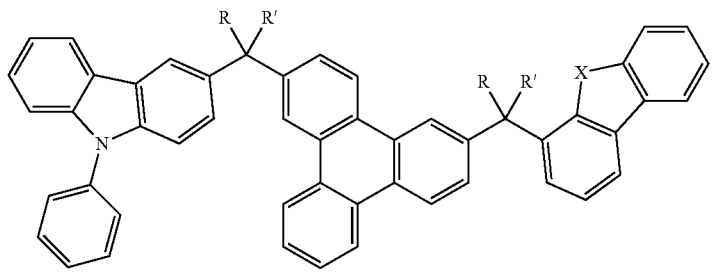

Compound 265 R = R' = H, X = S
Compound 266 R = R' = CH₃, X = S
Compound 267 R = R' = Ph, X = S
Compound 268 R = R' = H, X = O
Compound 269 R = R' = CH₃, X = O
Compound 270 R = R' = Ph, X = O

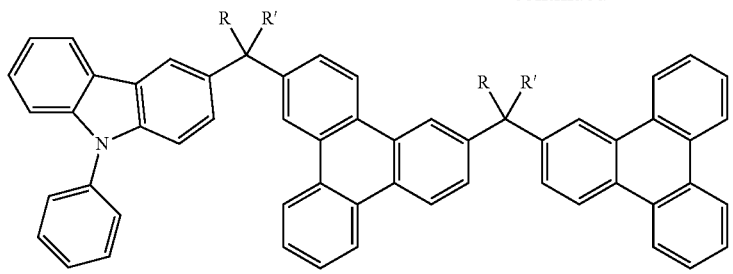
Compound 271 R = R' = H
Compound 272 R = R' = CH₃
Compound 273 R = R' = Ph
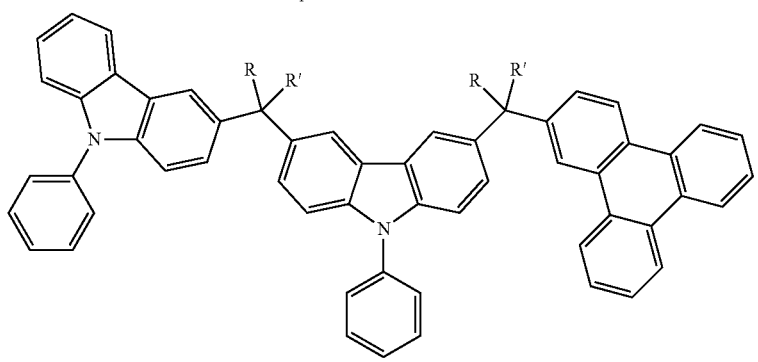
Compound 274 R = R' = H
Compound 275 R = R' = CH₃
Compound 276 R = R' = Ph
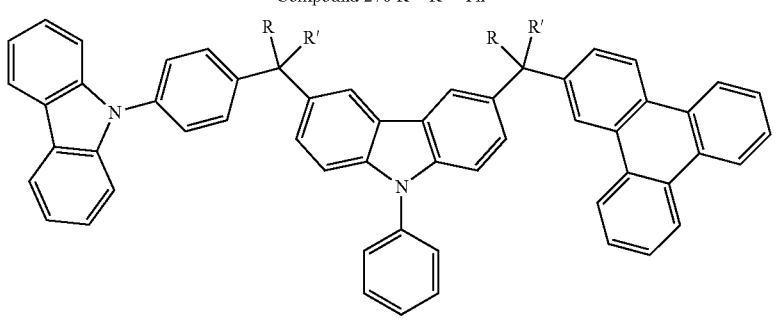
Compound 277 R = R' = H
Compound 278 R = R' = CH₃
Compound 279 R = R' = Ph
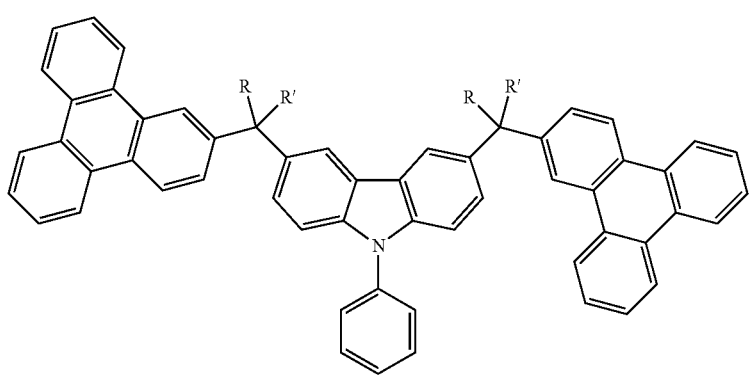
Compound 280 R = R' = H
Compound 281 R = R' = CH₃
Compound 282 R = R' = Ph -continued
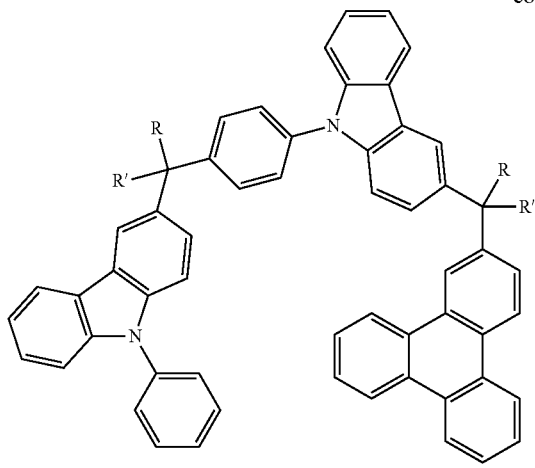
Compound 283 R = R' = H
Compound 284 R = R' = CH₃
Compound 285 R = R' = Ph
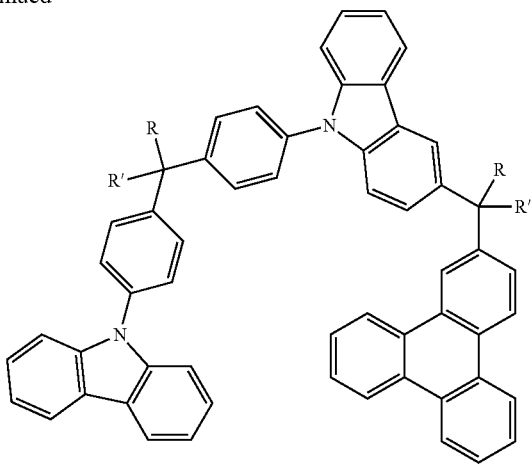
Compound 286 R = R' = H
Compound 287 R = R' = CH₃
Compound 288 R = R' = Ph
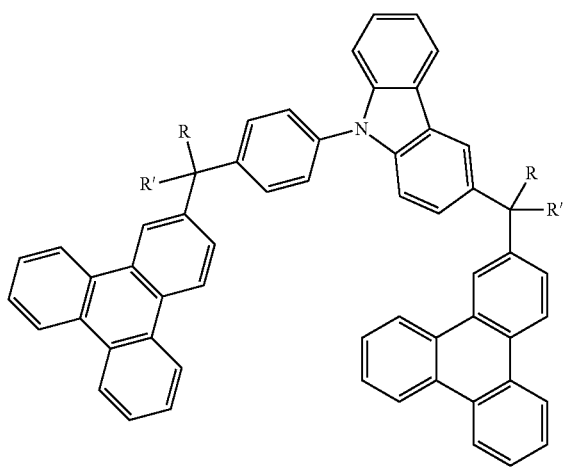
Compound 289 R = R' = H
Compound 290 R = R' = CH₃
Compound 291 R = R' = Ph
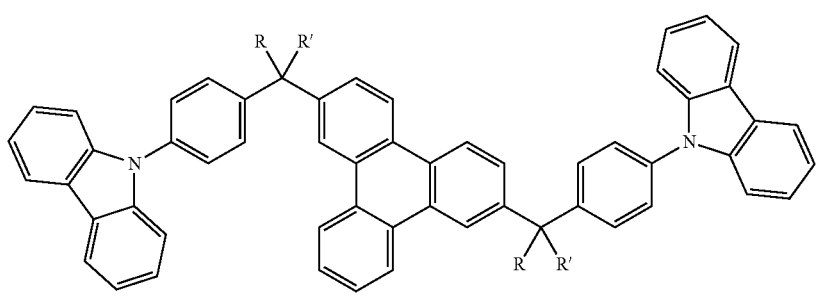
Compound 292 R = R' = H
Compound 293 R = R' = CH₃
Compound 294 R = R' = Ph -continued

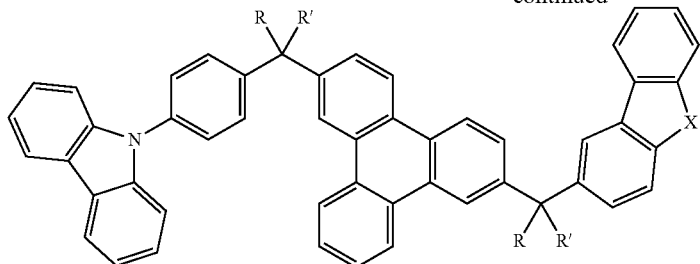

Compound 295 R = R' = H, X = S
Compound 296 R = R' = CH₃, X = S
Compound 297 R = R' = Ph, X = S
Compound 298 R = R' = H, X = O
Compound 299 R = R' = CH₃, X = O
Compound 300 R = R' = Ph, X = O

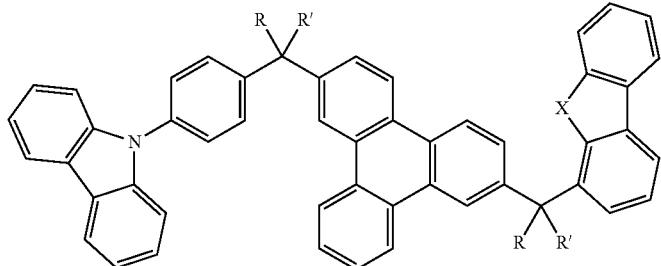

Compound 301 R = R' = H, X = S
Compound 302 R = R' = CH₃, X = S
Compound 303 R = R' = Ph, X = S
Compound 304 R = R' = H, X = O
Compound 305 R = R' = CH₃, X = O
Compound 306 R = R' = Ph, X = O

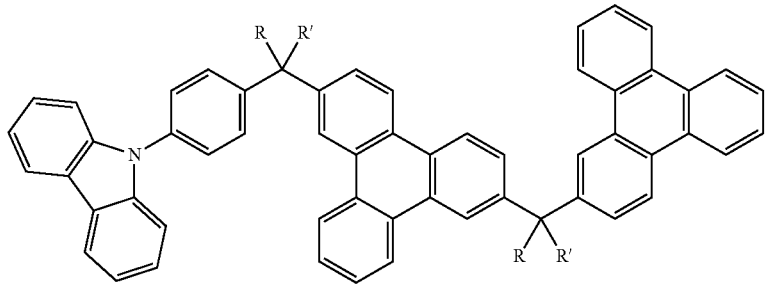

Compound 307 R = R' = H, X = S
Compound 308 R = R' = CH₃, X = S
Compound 309 R = R' = Ph, X = S
Compound 310 R = R' = H, X = O
Compound 311 R = R' = CH₃, X = O
Compound 312 R = R' = Ph, X = O

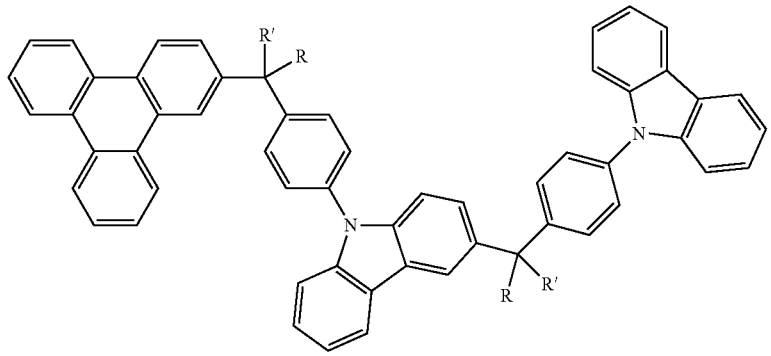

Compound 313 R = R' = H
Compound 314 R = R' = CH₃
Compound 315 R = R' = Ph

-continued
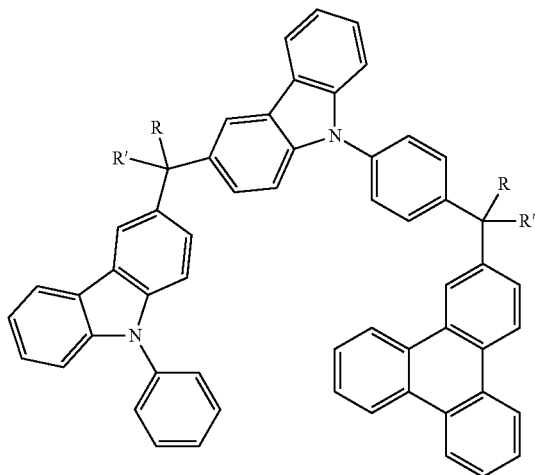
Compound 316 R = R' = H
Compound 317 R = R' = CH₃
Compound 318 R = R' = Ph
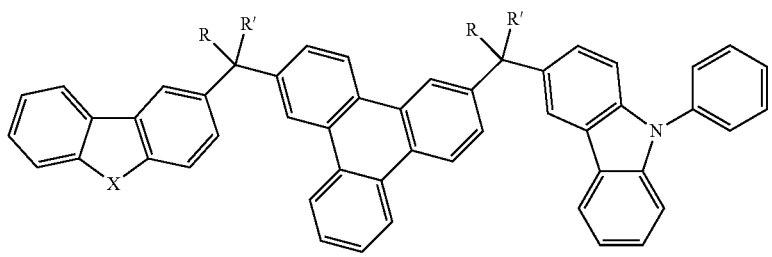
Compound 319 R = R' = H, X = S
Compound 320 R = R' = CH₃, X = S
Compound 321 R = R' = Ph, X = S
Compound 322 R = R' = H, X = O
Compound 323 R = R' = CH₃, X = O
Compound 324 R = R' = Ph, X = O
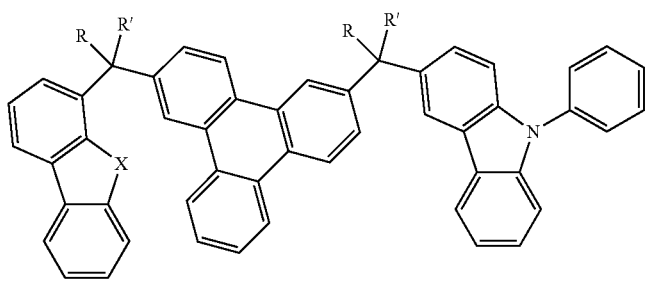
Compound 325 R = R' = H, X = S
Compound 326 R = R' = CH₃, X = S
Compound 327 R = R' = Ph, X = S
Compound 328 R = R' = H, X = O
Compound 329 R = R' = CH₃, X = O
Compound 330 R = R' = Ph, X = O -continued

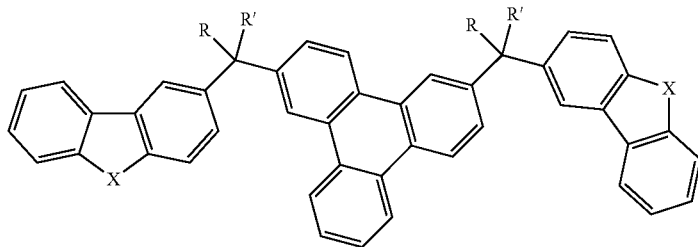

Compound 331 R = R' = H, X = S
Compound 332 R = R' = CH₃, X = S
Compound 333 R = R' = Ph, X = S
Compound 334 R = R' = H, X = O
Compound 335 R = R' = CH₃, X = O
Compound 336 R = R' = Ph, X = O

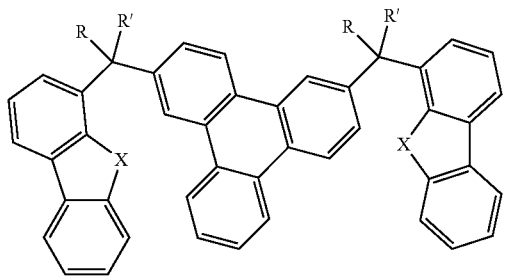

Compound 337 R = R' = H, X = S
Compound 338 R = R' = CH₃, X = S
Compound 339 R = R' = Ph, X = S
Compound 340 R = R' = H, X = O
Compound 341 R = R' = CH₃, X = O
Compound 342 R = R' = Ph, X = O

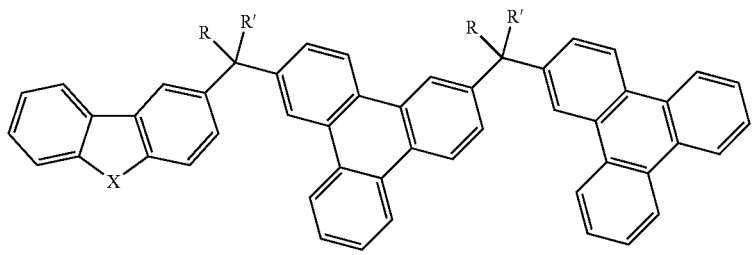

Compound 343 R = R' = H, X = S
Compound 344 R = R' = CH₃, X = S
Compound 345 R = R' = Ph, X = S
Compound 346 R = R' = H, X = O
Compound 347 R = R' = CH₃, X = O
Compound 348 R = R' = Ph, X = O

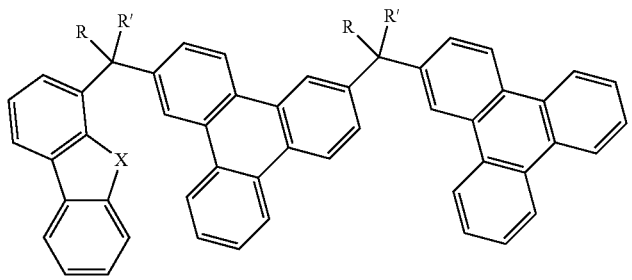

Compound 349 R = R' = H, X = S
Compound 350 R = R' = CH₃, X = S
Compound 351 R = R' = Ph, X = S
Compound 352 R = R' = H, X = O
Compound 353 R = R' = CH₃, X = O
Compound 354 R = R' = Ph, X = O -continued

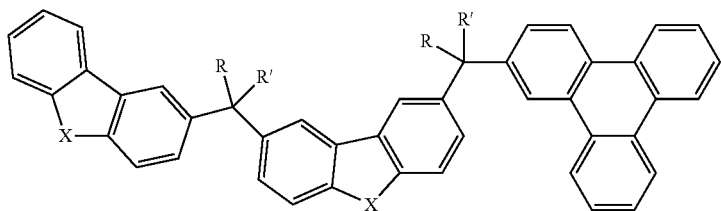

Compound 355 R = R' = H, X = S
Compound 356 R = R' = CH₃, X = S
Compound 357 R = R' = Ph, X = S
Compound 358 R = R' = H, X = O
Compound 359 R = R' = CH₃, X = O
Compound 360 R = R' = Ph, X = O

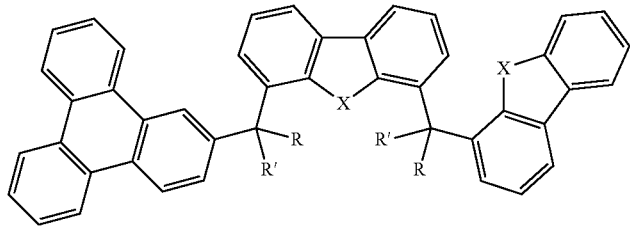

Compound 361 R = R' = H, X = S
Compound 362 R = R' = CH₃, X = S
Compound 363 R = R' = Ph, X = S
Compound 364 R = R' = H, X = O
Compound 365 R = R' = CH₃, X = O
Compound 366 R = R' = Ph, X = O

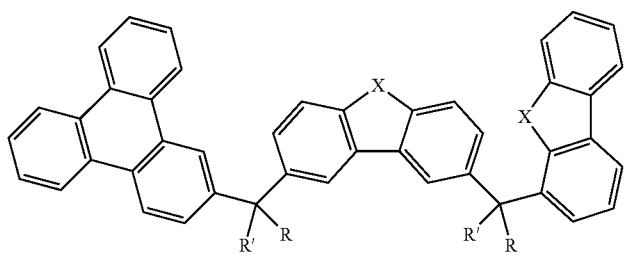

Compound 367 R = R' = H, X = S
Compound 368 R = R' = CH₃, X = S
Compound 369 R = R' = Ph, X = S
Compound 370 R = R' = H, X = O
Compound 371 R = R' = CH₃, X = O
Compound 372 R = R' = Ph, X = O

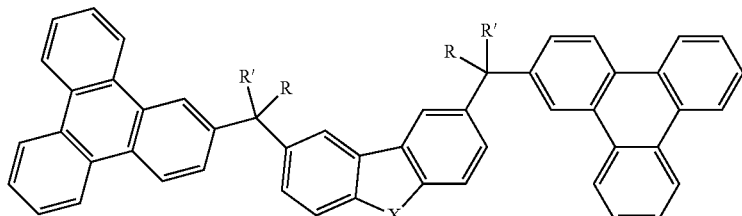

Compound 373 R = R' = H, X = S
Compound 374 R = R' = CH₃, X = S
Compound 375 R = R' = Ph, X = S
Compound 376 R = R' = H, X = O
Compound 377 R = R' = CH₃, X = O
Compound 378 R = R' = Ph, X = O -continued

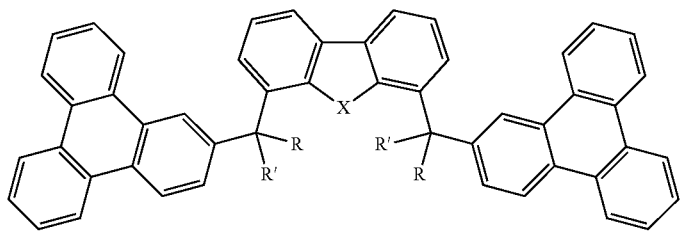

Compound 379 R = R' = H, X = S
Compound 380 R = R' = CH₃, X = S
Compound 381 R = R' = Ph, X = S
Compound 382 R = R' = H, X = O
Compound 383 R = R' = CH₃, X = O
Compound 384 R = R' = Ph, X = O

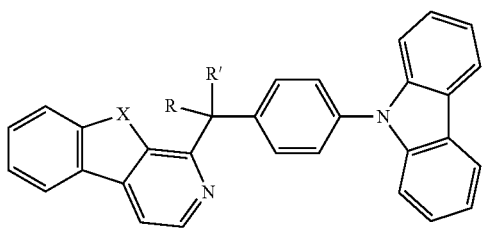

Compound 385 R = R' = H, X = S
Compound 386 R = R' = CH₃, X = S
Compound 387 R = R' = Ph, X = S
Compound 388 R = R' = H, X = O
Compound 389 R = R' = CH₃, X = O
Compound 390 R = R' = Ph, X = O

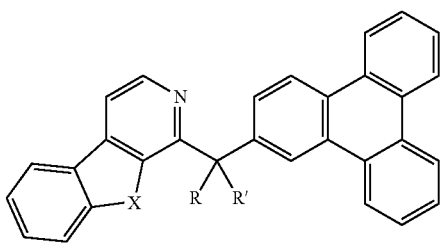

Compound 391 R = R' = H, X = S
Compound 392 R = R' = CH₃, X = S
Compound 393 R = R' = Ph, X = S
Compound 394 R = R' = H, X = O
Compound 395 R = R' = CH₃, X = O
Compound 396 R = R' = Ph, X = O

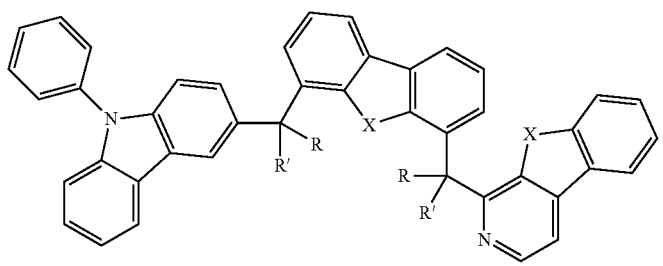

Compound 397 R = R' = H, X = S
Compound 398 R = R' = CH₃, X = S
Compound 399 R = R' = Ph, X = S
Compound 400 R = R' = H, X = O
Compound 401 R = R' = CH₃, X = O
Compound 402 R = R' = Ph, X = O

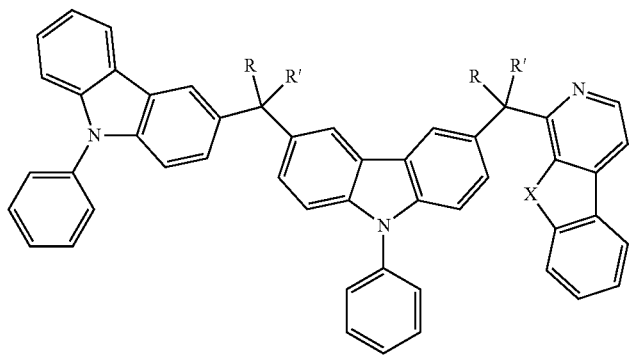

Compound 403 R = R' = H, X = S
Compound 404 R = R' = CH₃, X = S
Compound 405 R = R' = Ph, X = S
Compound 406 R = R' = H, X = O
Compound 407 R = R' = CH₃, X = O
Compound 408 R = R' = Ph, X = O

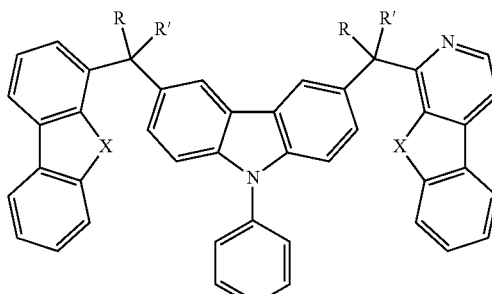

Compound 409 R = R' = H, X = S
Compound 410 R = R' = CH₃, X = S
Compound 411 R = R' = Ph, X = S
Compound 412 R = R' = H, X = O
Compound 413 R = R' = CH₃, X = O
Compound 414 R = R' = Ph, X = O -continued

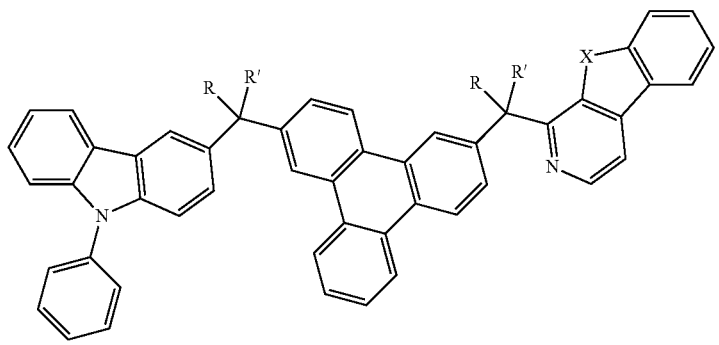

Compound 415 R = R' = H, X = S
Compound 416 R = R' = CH₃, X = S
Compound 417 R = R' = Ph, X = S
Compound 418 R = R' = H, X = O
Compound 419 R = R' = CH₃, X = O
Compound 420 R = R' = Ph, X = O

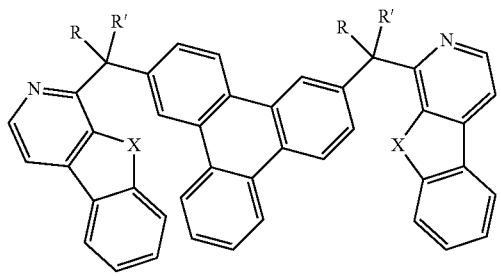

Compound 421 R = R' = H, X = S
Compound 422 R = R' = CH₃, X = S
Compound 423 R = R' = Ph, X = S
Compound 424 R = R' = H, X = O
Compound 425 R = R' = CH₃, X = O
Compound 426 R = R' = Ph, X = O

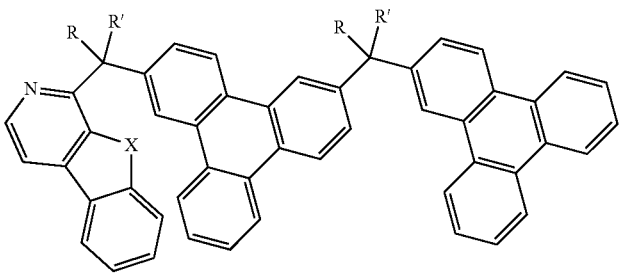

Compound 427 R = R' = H, X = S
Compound 428 R = R' = CH₃, X = S
Compound 429 R = R' = Ph, X = S
Compound 430 R = R' = H, X = O
Compound 431 R = R' = CH₃, X = O
Compound 432 R = R' = Ph, X = O

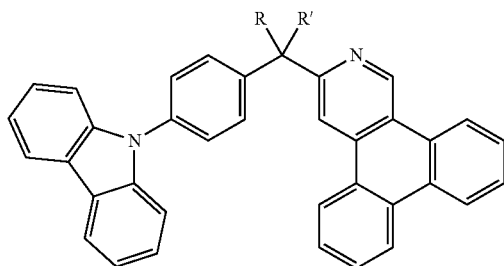

Compound 433 R = R' = H
Compound 434 R = R' = CH₃
Compound 435 R = R' = Ph

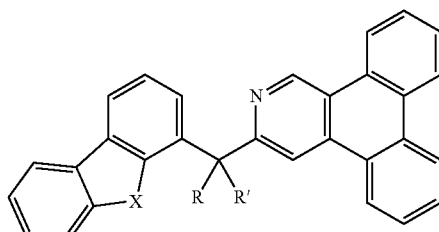

Compound 436 R = R' = H, X = S
Compound 437 R = R' = CH₃, X = S
Compound 438 R = R' = Ph, X = S
Compound 439 R = R' = H, X = O
Compound 440 R = R' = CH₃, X = O
Compound 441 R = R' = Ph, X = O

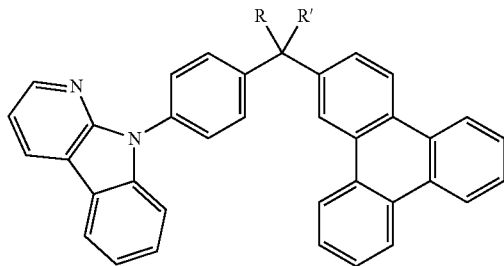

Compound 442 R = R' = H
Compound 443 R = R' = CH₃
Compound 444 R = R' = Ph

-continued

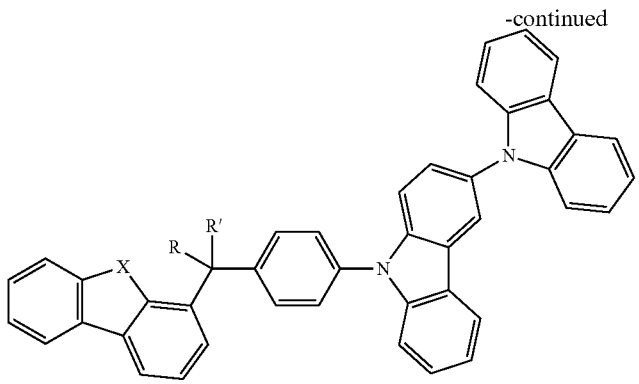

Compound 445 R = R' = H, X = S
Compound 446 R = R' = CH₃, X = S
Compound 447 R = R' = Ph, X = S
Compound 448 R = R' = H, X = O
Compound 449 R = R' = CH₃, X = O
Compound 450 R = R' = Ph, X = O

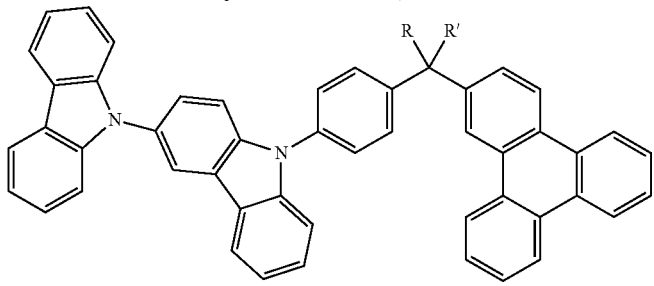

Compound 451 R = R' = H
Compound 452 R = R' = CH₃
Compound 453 R = R' = Ph

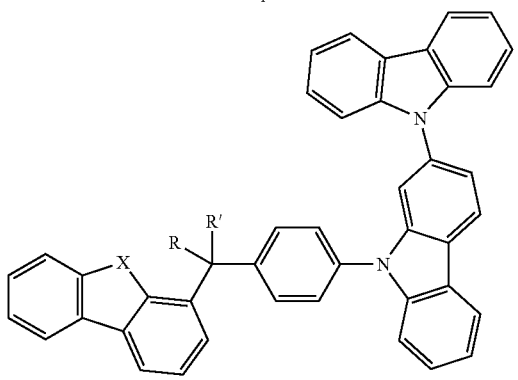

Compound 454 R = R' = H, X = S
Compound 455 R = R' = CH₃, X = S
Compound 456 R = R' = Ph, X = S
Compound 457 R = R' = H, X = O
Compound 458 R = R' = CH₃, X = O
Compound 459 R = R' = Ph, X = O In some embodiments, A is dibenzothiophene, L is —CH₂—, and B is N-phenyl carbazole.

In some embodiments, a first device is provided. In some embodiments, the first device comprises a first organic light emitting device. In some embodiments, the first organic light emitting device comprises an anode, a cathode, and an organic layer, disposed between the anode and the cathode, comprising a compound having formula I:

A-L-B    (I).

In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;

A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

L is selected from the group consisting of alkyl, cycloalkyl, substituted alkyl, and substituted cycloalkyl; and L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, a first device is provided. In some embodiments, the first device comprises a first organic light emitting device. In some embodiments, the first organic light emitting device comprises an anode, a cathode, and an organic layer, disposed between the anode and the cathode, comprising a compound having formula I:

$$A\text{-}L\text{-}B \qquad (I).$$

In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;

A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

L is selected from the group consisting of alkyl, cycloalkyl, substituted alkyl, and substituted cycloalkyl; and L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein A including optional substituents and B including optional substituents are different.

In some embodiments, the organic layer is an emissive layer and the first compound is a host.

In some embodiments, the organic layer further comprises a phosphorescent emissive dopant.

In some embodiments, the phosphorescent emissive dopant is a transition metal complex having at least one ligand or part of the ligand if the ligand is more than bidentate selected from the group consisting of:

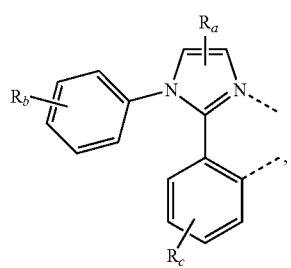

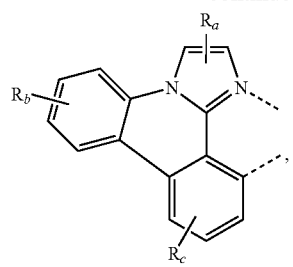

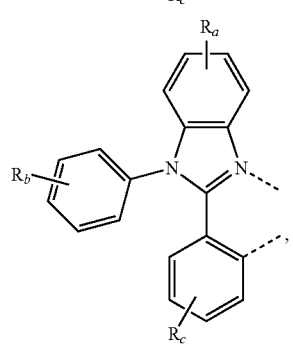

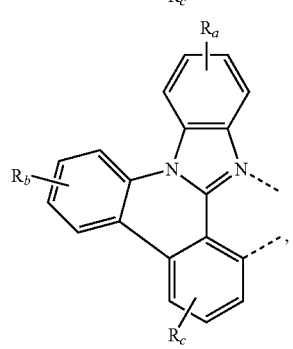 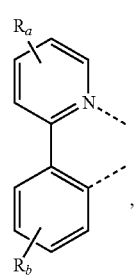

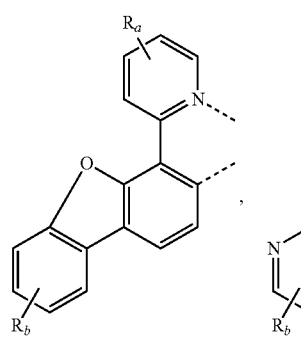 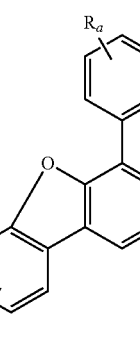

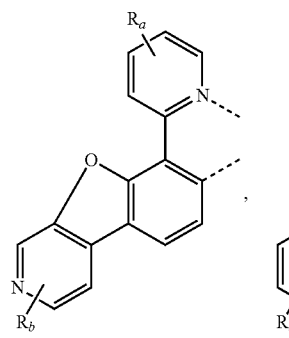 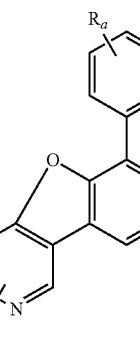

-continued

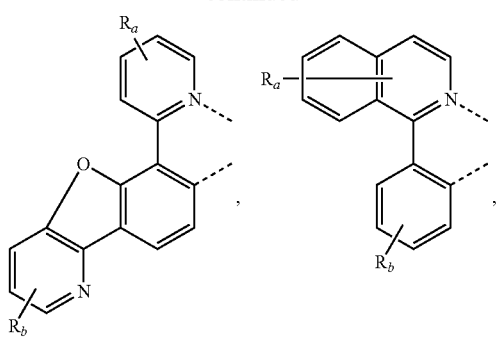
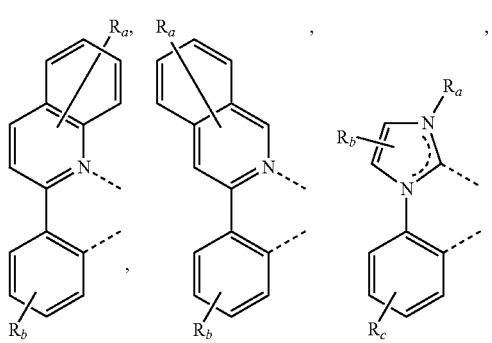
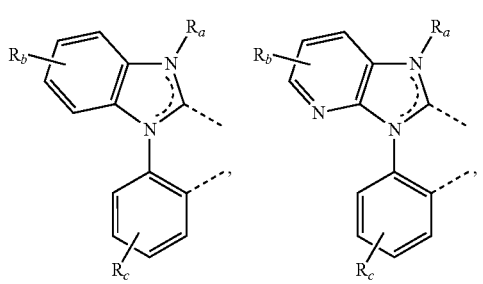
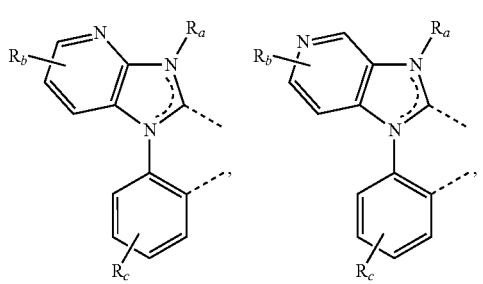
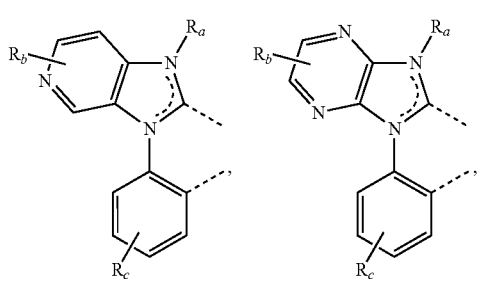

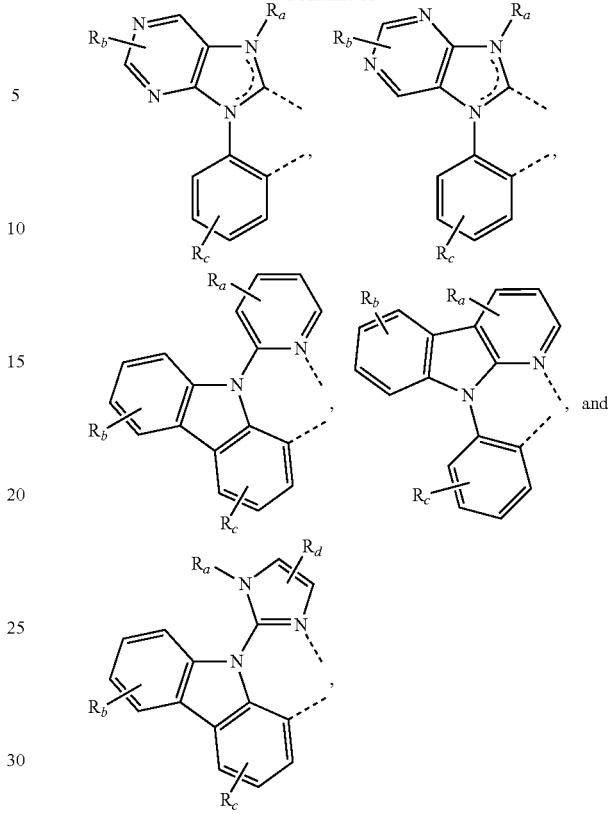

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In some embodiments, the organic layer is a blocking layer and the first compound is a blocking material in the organic layer.

In some embodiments, the first device is a consumer product.

In some embodiments, the first device is an organic light-emitting device.

In some embodiments, the first device comprises a lighting panel.

In some embodiments, the compounds described herein are provided in a formulation with other materials present in the device. For example, the compounds of the invention may be provided in a formulation in conjunction with a wide variety of hosts, transport layers, blocking layers, injection layers, electrodes, or other layers.

In some embodiments, a formulation comprising a compound having formula I:

$$A\text{-}L\text{-}B \qquad (I).$$

is provided. In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;
A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;
L is selected from the group consisting of alkyl, cycloalkyl, substituted alkyl, and substituted cycloalkyl; and
L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, a formulation comprising a compound having formula I:

$$A\text{-}L\text{-}B \quad (I).$$

is provided. In the compound of formula I, A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;
A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;
L is selected from the group consisting of alkyl, cycloalkyl, substituted alkyl, and substituted cycloalkyl; and
L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and
wherein A including optional substituents and B including optional substituents are different.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

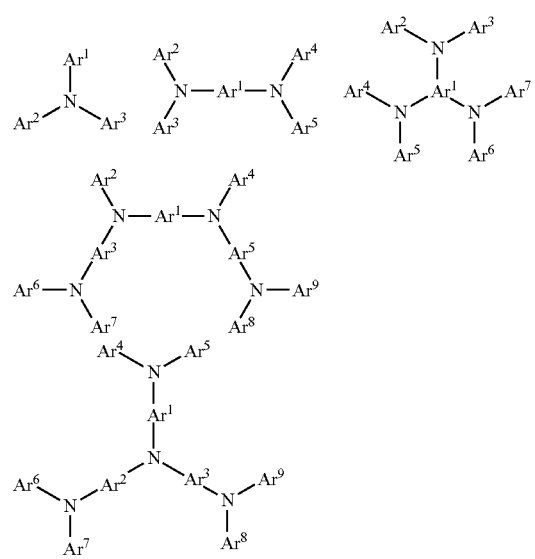

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

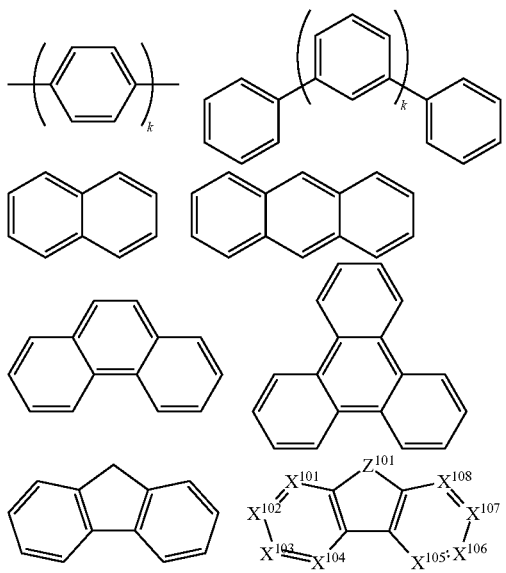

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

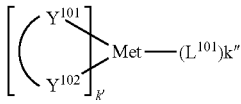

Met is a metal; $(Y^{101}\text{-}Y^{102})$ is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative.

In another aspect, $(Y^{101}\text{-}Y^{102})$ is a carbene ligand.

In another aspect, Met is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

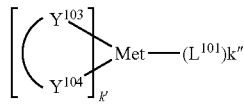

Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

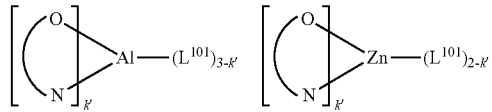

(O—N) is a bidentate ligand, having metal coordinated to atoms O and N.

In another aspect, Met is selected from Ir and Pt.

In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

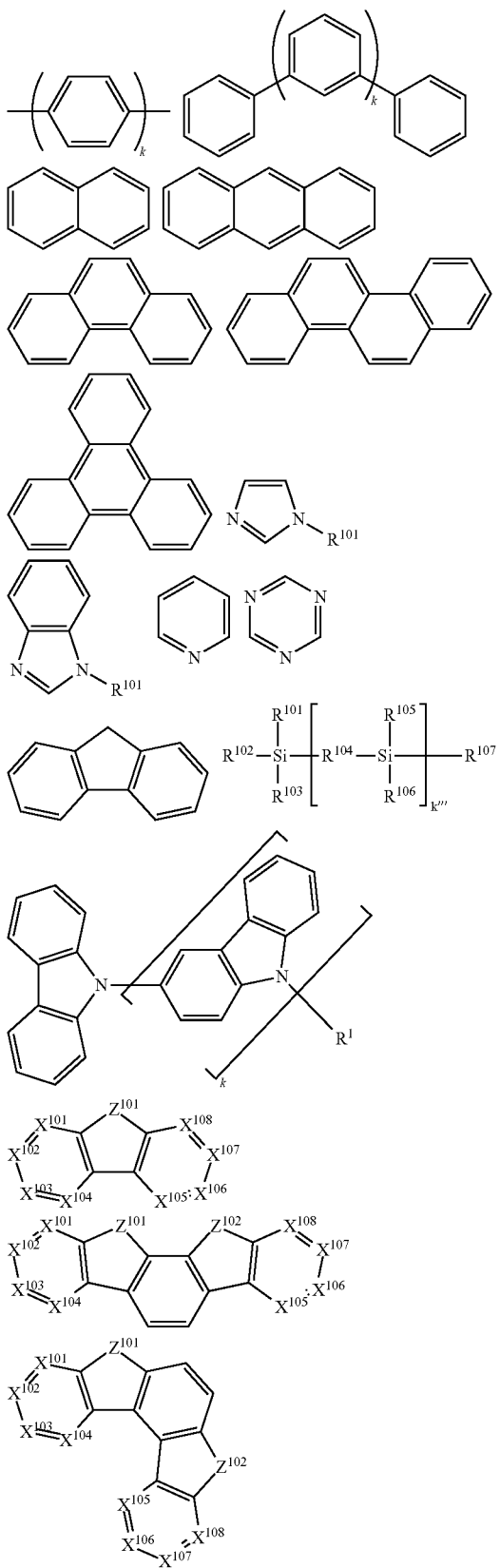

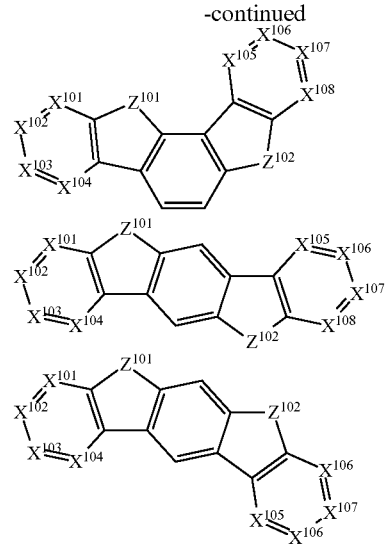

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.

$X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

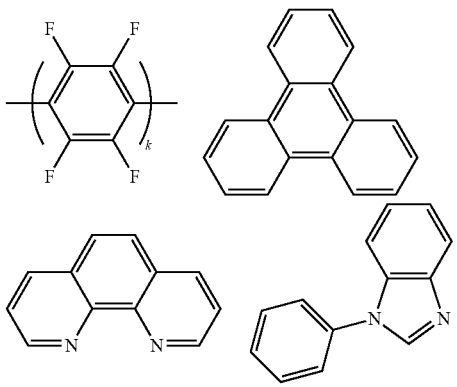

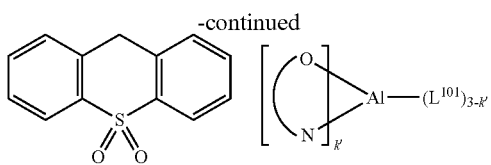

k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

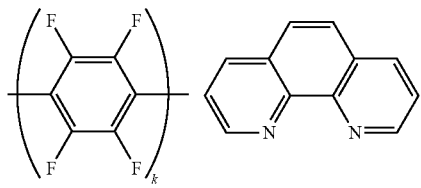

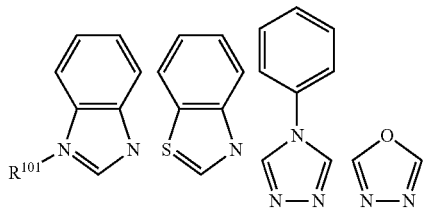

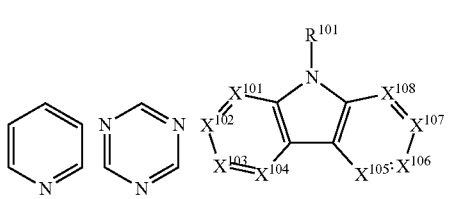

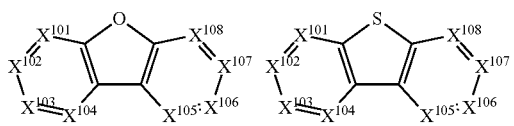

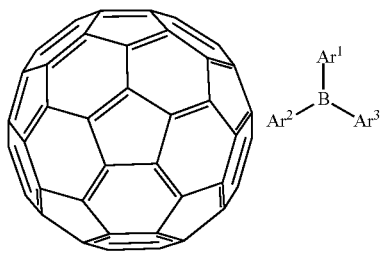

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

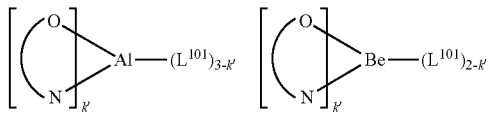

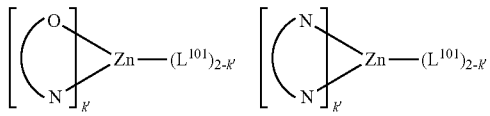

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in TABLE 2 below. TABLE 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| *Hole injection materials* | | |
| Phthalocyanine and porphryin compounds | (copper phthalocyanine structure) | Appl. Phys. Lett. 69, 2160 (1996) |
| Starburst triarylamines | (starburst triarylamine structure) | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | (PEDOT:PSS structure) | Synth. Met. 87, 171 (1997) WO2007002683 |
| Phosphonic acid and silane SAMs | $N-(C_6H_4-SiCl_3)_3$ | US20030162053 |

TABLE 2-continued

| MATERIAL | EXAMPLES OF MATERIAL | PUBLICATIONS |
|---|---|---|
| Triarylamine or polythiophene polymers with conductivity dopants | | EP1725079A1 |
| Organic compounds with conductive inorganic compounds, such as molybdenum and tungsten oxides | + MoO$_x$ | US20050123751 SID Symposium Digest, 37, 923 (2006) WO2009018009 |
| n-type semiconducting organic complexes | | US20020158242 |
| Metal organometallic complexes | | US20060240279 |
| Cross-linkable compounds | | US20080220265 |

TABLE 2-continued
| MATERIAL | EXAMPLES OF MATERIAL | PUBLICATIONS |
| --- | --- | --- |
| Polythiophene based polymers and copolymers | 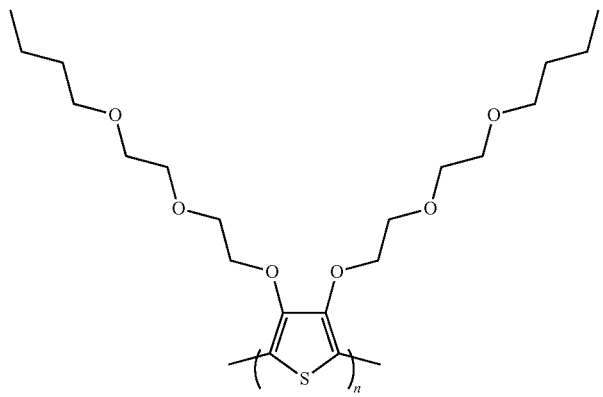 | WO 2011075644<br>EP2350216 |
| Hole transporting materials | | |
| Triarylamines<br>(e.g., TPD, α-NPD) | 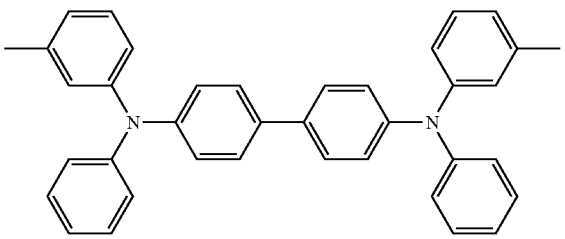 | Appl. Phys. Lett.<br>51, 913 (1987) |
| | 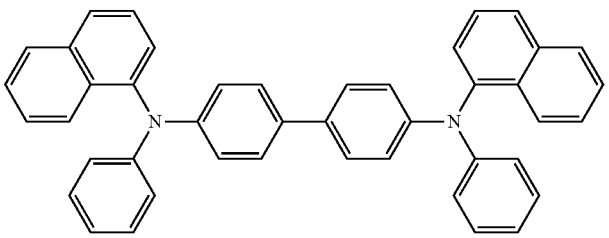 [SMILES: c1ccc(N(c2ccc(-c3ccc(N(c4ccccc4)c4cccc5ccccc45)cc3)cc2)c2cccc3ccccc23)cc1] | U.S. Pat. No.<br>5,061,569 |
| | 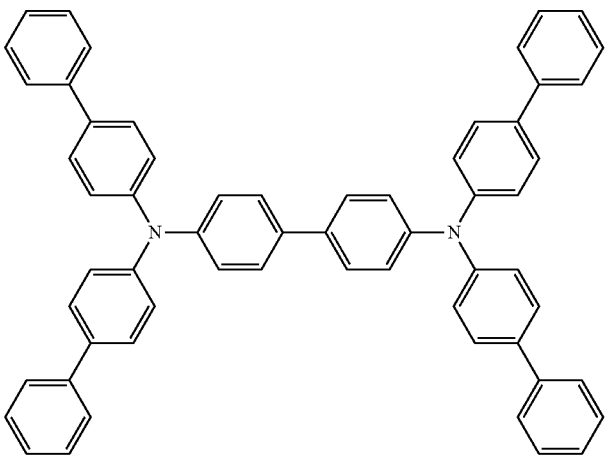 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 2-continued

| MATERIAL | EXAMPLES OF MATERIAL | PUBLICATIONS |
|---|---|---|
| | | J. Mater. Chem. 3, 319 (1993) |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |

TABLE 2-continued

| MATERIAL | EXAMPLES OF MATERIAL | PUBLICATIONS |
| --- | --- | --- |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |

TABLE 2-continued

| MATERIAL | EXAMPLES OF MATERIAL | PUBLICATIONS |
|---|---|---|
| Metal carbene complexes | [structure of Ir complex with phenyl-benzimidazole ligands, subscript 3] | US20080018221 |

Phosphorescent OLED hosts materials
Red hosts

| MATERIAL | EXAMPLES OF MATERIAL | PUBLICATIONS |
|---|---|---|
| Arylcarbazoles | [structure of biphenyl with two carbazole groups] | Appl. Phys. Lett. 78, 1622 (2001) |
| Metal 8-hydroxyquinolates (e.g., Alq$_3$, BAlq) | [structure of Alq$_3$] | Nature 395, 151 (1998) |
| | [structure of Al complex with biphenyl] | US20060202194 |
| | [structure of Al complex with phenylnaphthalene] | WO2005014551 |
| | [structure of Al complex with biphenyl-carbazole] | WO2006072002 |

TABLE 2-continued

| MATERIAL | EXAMPLES OF MATERIAL | PUBLICATIONS |
| --- | --- | --- |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778. WO2009063833, US20090045731, US20090045730. WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |

TABLE 2-continued
| MATERIAL | EXAMPLES OF MATERIAL | PUBLICATIONS |
|---|---|---|
| | 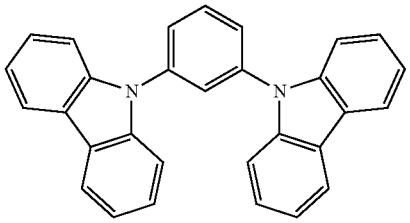 [SMILES: c1cc(-n2c3ccccc3c3ccccc32)cc(-n2c3ccccc3c3ccccc32)c1] | US20030175553 |
| | 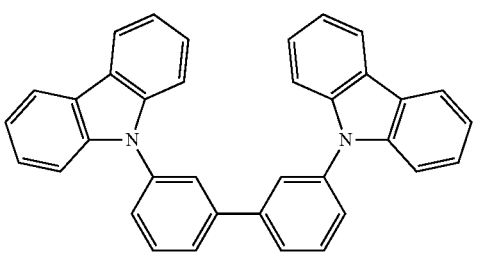 [SMILES: c1cc(-c2cccc(-n3c4ccccc4c4ccccc43)c2)cc(-n2c3ccccc3c3ccccc32)c1] | WO2001039234 |
| Aryltriphenylene compounds | 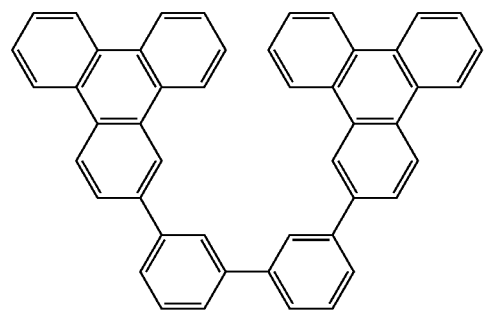 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 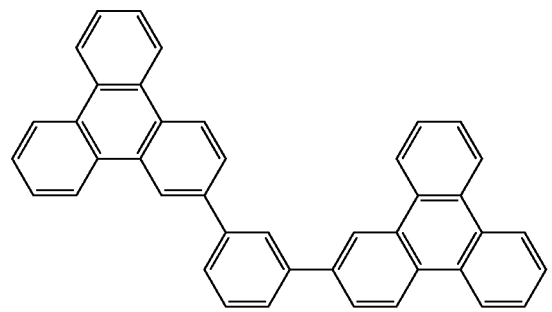 [SMILES: c1cc(-c2ccc3c4ccccc4c4ccccc4c3c2)cc(-c2ccc3c4ccccc4c4ccccc4c3c2)c1] | US20060280965 |
| | 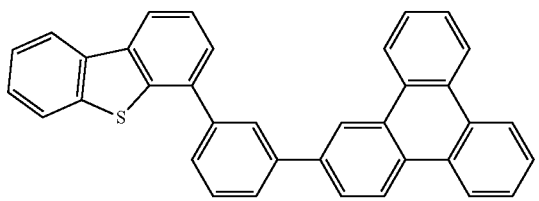 [SMILES: c1cc(-c2ccc3c4ccccc4c4ccccc4c3c2)cc(-c2cccc3c2sc2ccccc23)c1] | WO2009021126 |

TABLE 2-continued
| MATERIAL | EXAMPLES OF MATERIAL | PUBLICATIONS |
| --- | --- | --- |
| Poly-fused heteroaryl compounds | 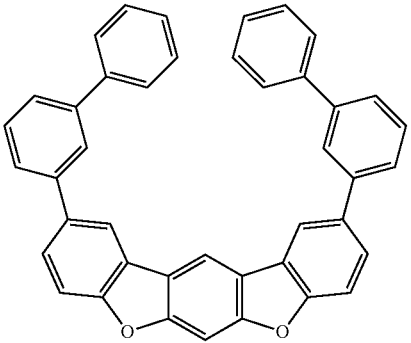 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 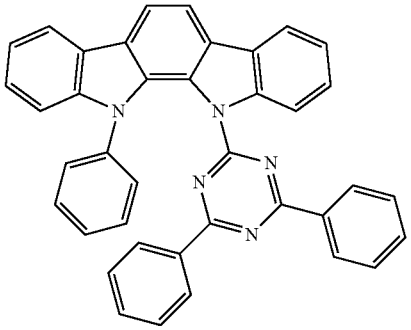 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 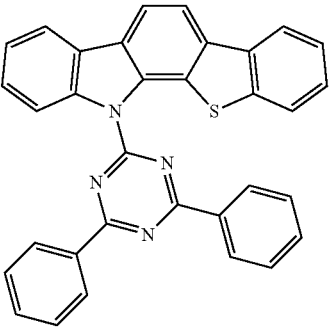 [SMILES: c1ccc(-c2nc(-c3ccccc3)nc(-n3c4ccccc4c4ccc5c6ccccc6sc5c43)n2)cc1] | WO2010107244 |
| Aza-carbazole/<br>DBT/DBF | 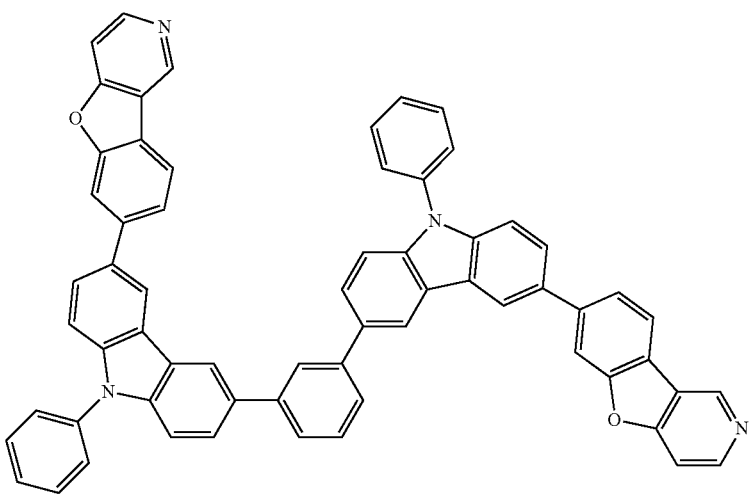 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 2-continued
| MATERIAL | EXAMPLES OF MATERIAL | PUBLICATIONS |
|---|---|---|
| | 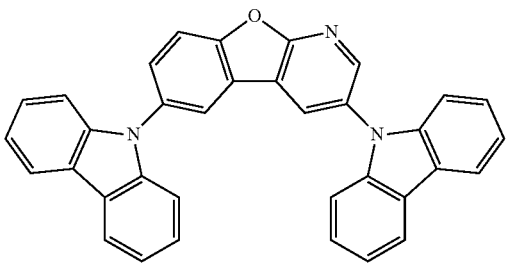 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 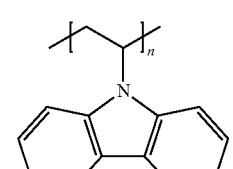 | Appl. Phys. Lett. 77, 2280 (2000) |
| Spirofluorene compounds | 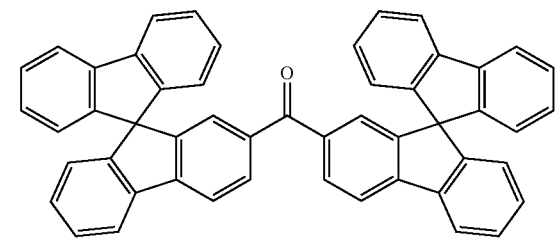 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzooxazole compounds | 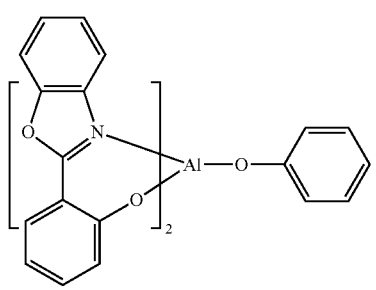 | WO2005089025 |
| | 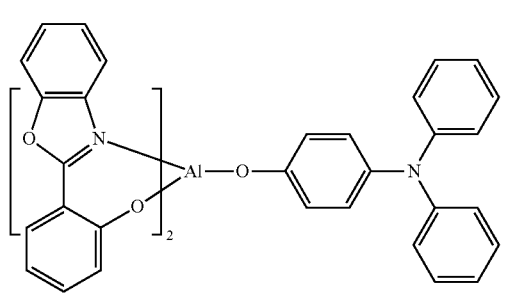 | WO2006132173 |
| | 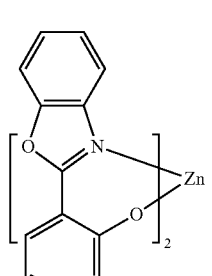 | JP200511610 |

TABLE 2-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |

| MATERIAL | EXAMPLES OF MATERIAL | PUBLICATIONS |
|---|---|---|
| | 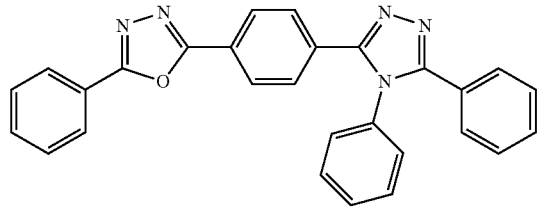 [SMILES: c1ccc(-c2nnc(-c3ccc(-c4nnc(-c5ccccc5)n4-c4ccccc4)cc3)o2)cc1] | WO2004107822 |
| Tetraphenylene complexes | 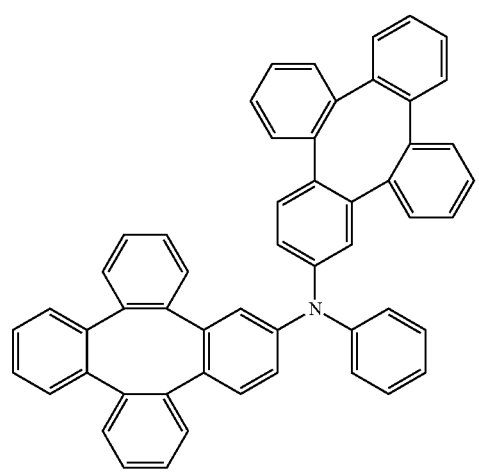 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 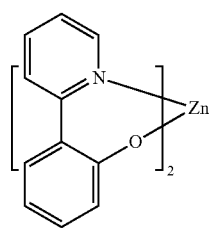 | WO2005030900 |
| Metal coordination complexes (e.g., Zn, Al with N^N ligands) | 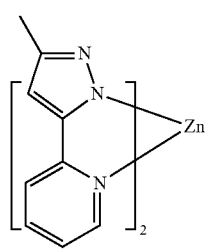 | US20040137268, US20040137267 |
Blue hosts
| | | |
|---|---|---|
| Arylcarbazoles | 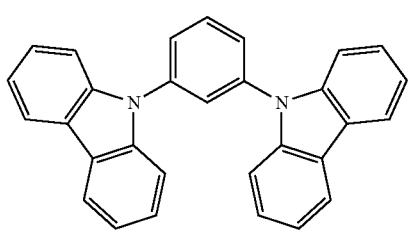 [SMILES: c1cc(-n2c3ccccc3c3ccccc32)cc(-n2c3ccccc3c3ccccc32)c1] | Appl. Phys. Lett, 82, 2422 (2003) |

TABLE 2-continued
| MATERIAL | EXAMPLES OF MATERIAL | PUBLICATIONS |
|---|---|---|
| | 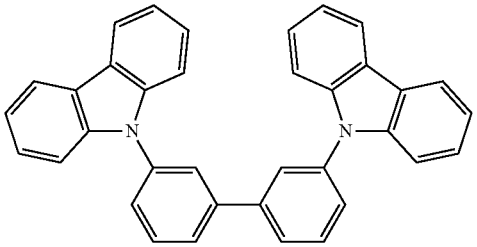 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran- carbazole compounds | 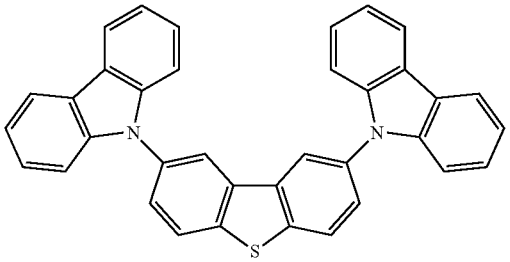 [SMILES: c1ccc2c(c1)c1ccccc1n2-c1ccc2sc3ccc(-n4c5ccccc5c5ccccc54)cc3c2c1] | WO2006114966, US20090167162 |
| | 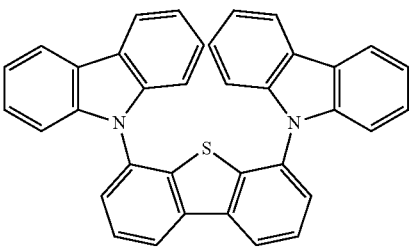 [SMILES: c1cc(-n2c3ccccc3c3ccccc32)c2sc3c(-n4c5ccccc5c5ccccc54)cccc3c2c1] | US20090167162 |
| | 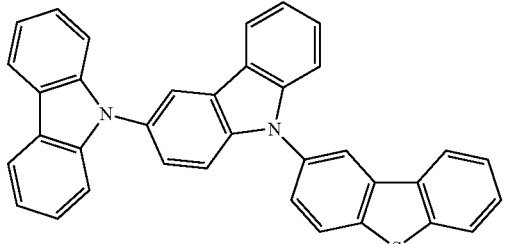 | WO2009086028 |
| | 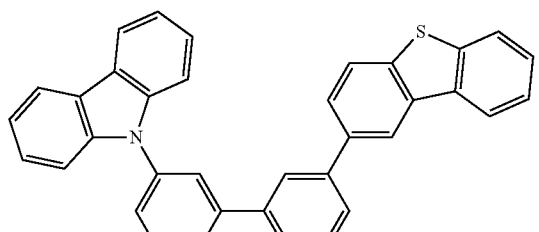 | US20090030202, US20090017330 |
| | 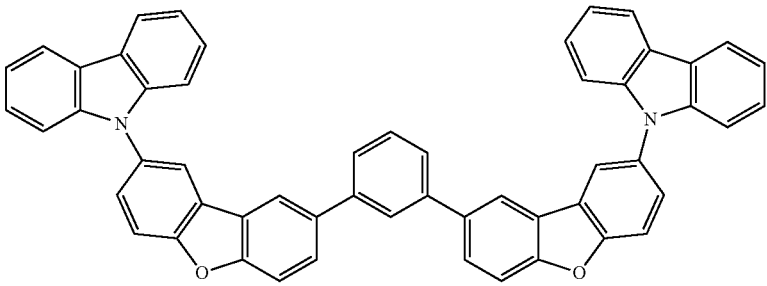 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE 2-continued
| MATERIAL | EXAMPLES OF MATERIAL | PUBLICATIONS |
|---|---|---|
| Silicon aryl compounds | 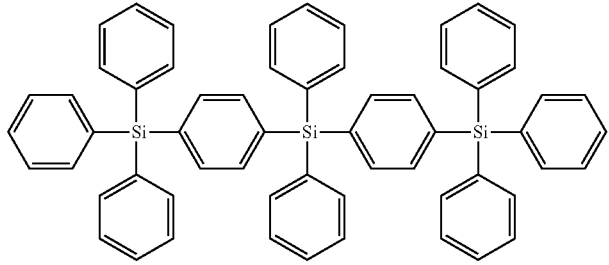 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 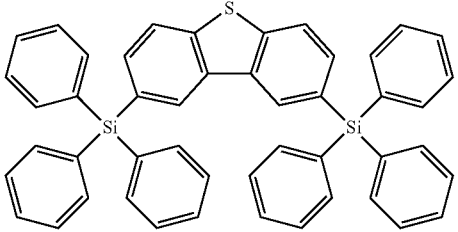 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 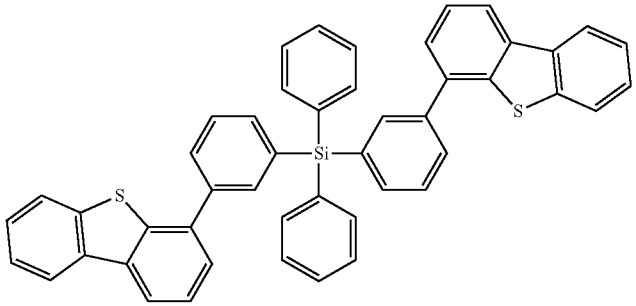 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 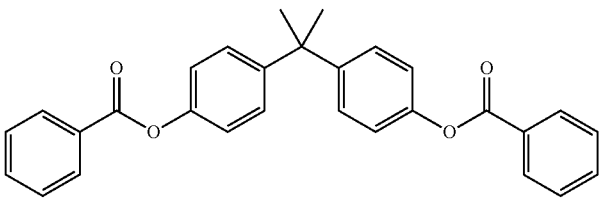 | WO2006100298 |
| Carbazole linked by non-conjugated groups | 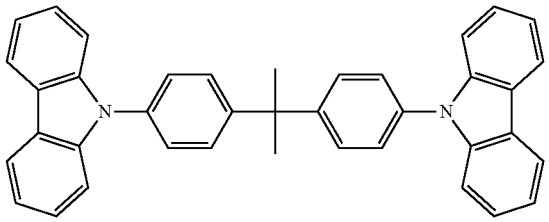 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 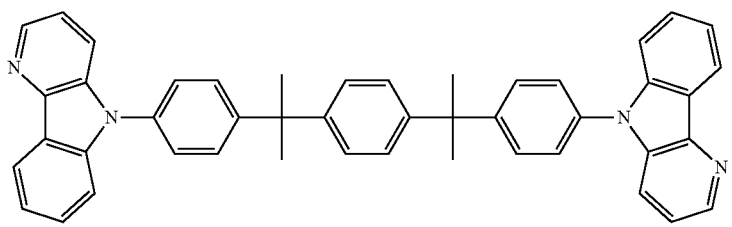 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 2-continued

| MATERIAL | EXAMPLES OF MATERIAL | PUBLICATIONS |
| --- | --- | --- |
| High triplet metal organometallic complex | | U.S. Pat. No. 7,154,114 |

Phosphorescent dopants
Red dopants

| MATERIAL | EXAMPLES OF MATERIAL | PUBLICATIONS |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

| MATERIAL | EXAMPLES OF MATERIAL | PUBLICATIONS |
|---|---|---|
| | 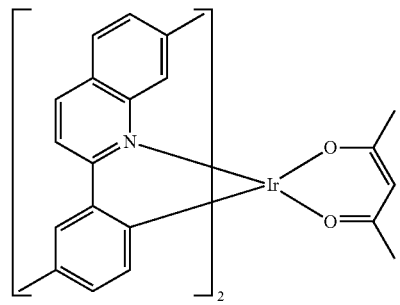 | US20060202194 |
| | 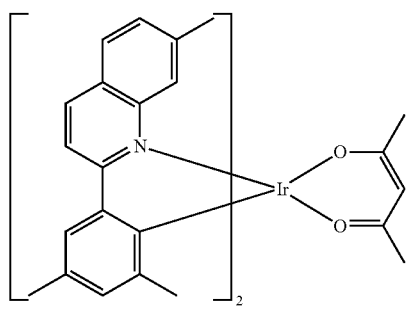 | US20060202194 |
| | 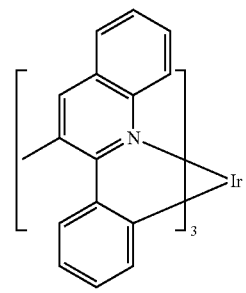 | US20070087321 |
| | 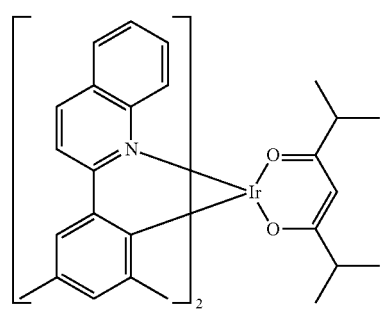 | US20080261076<br>US20100090591 |
| | 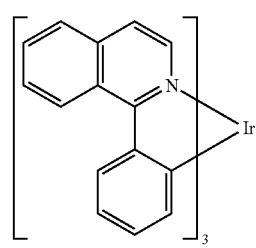 | US20070087321 |

TABLE 2-continued
| MATERIAL | EXAMPLES OF MATERIAL | PUBLICATIONS |
|---|---|---|
| | 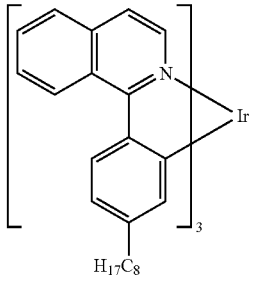 | Adv. Mater. 19, 739 (2007) |
| | 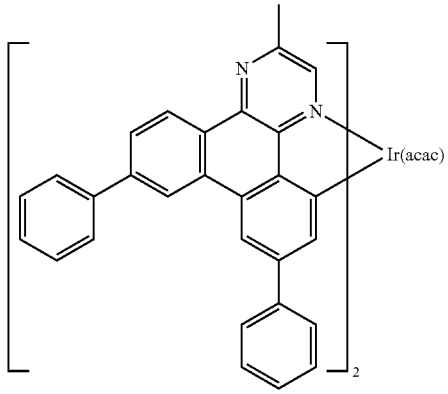 | WO2009100991 |
| | 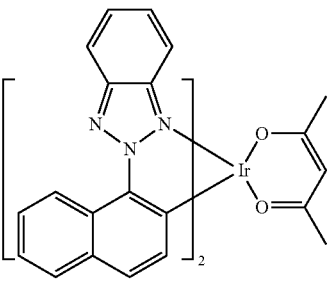 | WO2008101842 |
| | 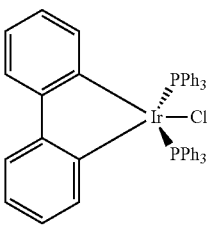 | U.S. Pat. No. 7,232,618 |
| Platinum(II) organometallic complexes | 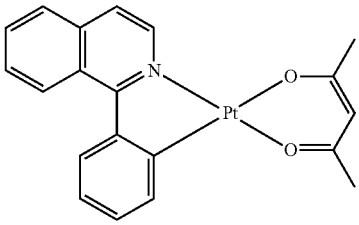 | WO2003040257 |

| MATERIAL | EXAMPLES OF MATERIAL | PUBLICATIONS |
|---|---|---|
| | 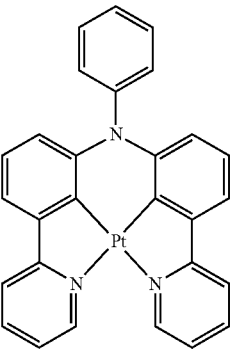 | US20070103060 |
| Osmium(III) complexes | 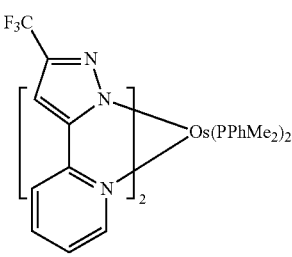 | Chem. Mater. 17, 3532 (2005) |
| Ruthenium(II) complexes | 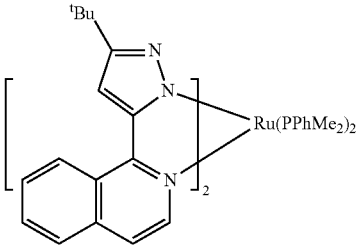 | Adv. Mater. 17, 1059 (2005) |
| Rhenium (I), (II), and (III) complexes | 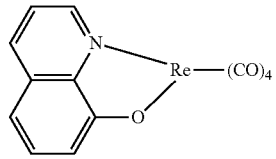 | US20050244673 |
| | Green dopants | |
| Iridium(III) organometallic complexes | 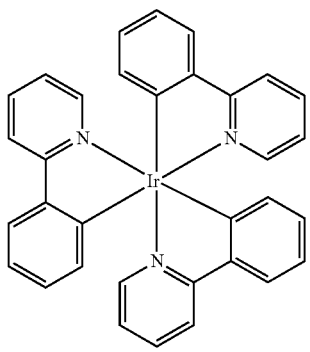\and its derivatives | Inorg. Chem. 40, 1704 (2001) |

TABLE 2-continued
| MATERIAL | EXAMPLES OF MATERIAL | PUBLICATIONS |
|---|---|---|
| | 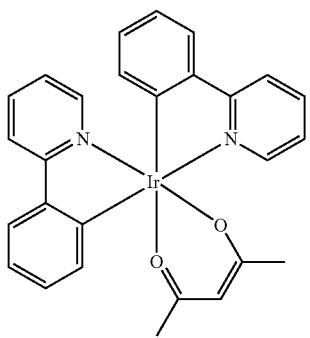 | US20020034656 |
| | 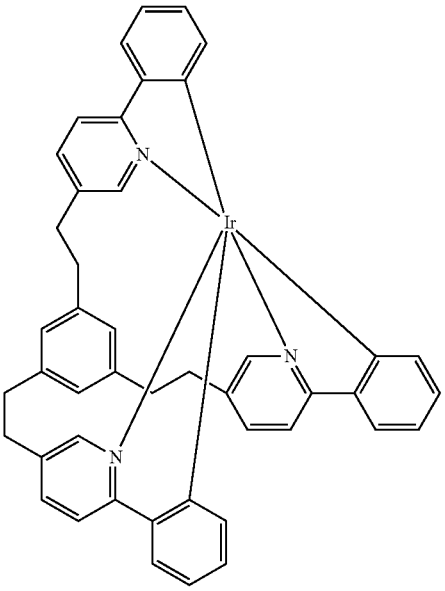 | U.S. Pat. No. 7,332,232 |
| | 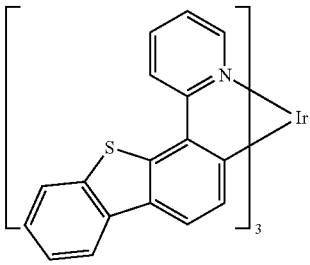 | US20090108737<br>WO2010028151<br>EP1841834B<br>US20060127696<br>US20090039776<br>U.S. Pat. No. 6,921,915 |
| | 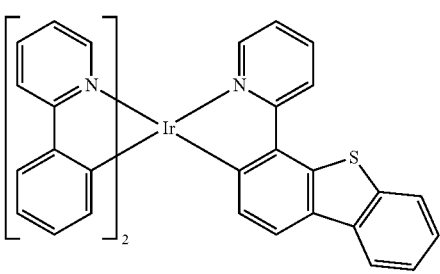 | US20100244004 |

TABLE 2-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20076190359 |
| | | US 20060008670 JP2007123392 |
| | | WO2010086089, WO2011044988 |
| | | Adv. Mater. 16, 2003 (2004) |

TABLE 2-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090065846 |
| | | US20080015355 |
| | | US20010015432 |
| | | US20100295032 |

TABLE 2-continued
| MATERIAL | EXAMPLES OF MATERIAL | PUBLICATIONS |
|---|---|---|
| Monomer for polymeric metal organometallic compounds | 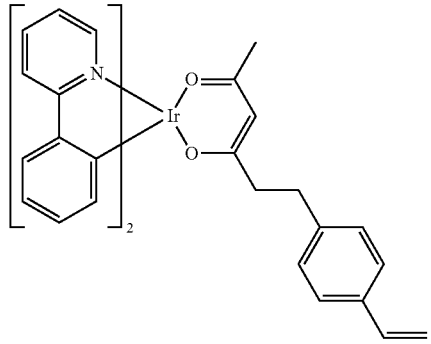 | U.S. Pat. No. 7,250,226, U.S. Pat. No. 7,396,598 |
| Pt(II) organometallic complexes, including polydentated ligands | 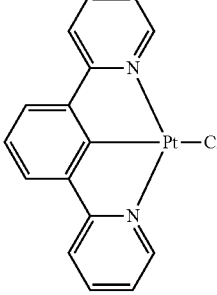 | Appl. Phys. Lett. 86, 153505 (2005) |
| | 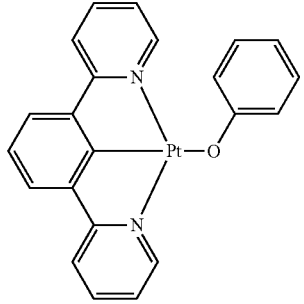 | Appl. Phys. Lett. 86, 153505 (2005) |
| | 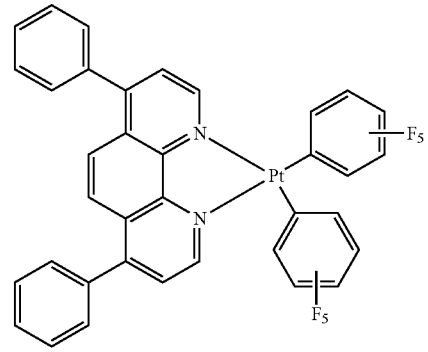 | Chem. Lett. 34, 592 (2005) |
| | 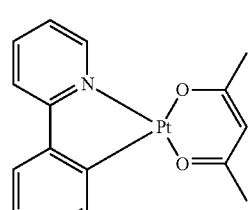 | WO2002015645 |

TABLE 2-continued
| MATERIAL | EXAMPLES OF MATERIAL | PUBLICATIONS |
|---|---|---|
| | 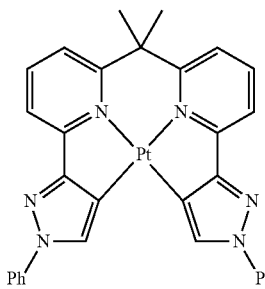 | US20060263635 |
| | 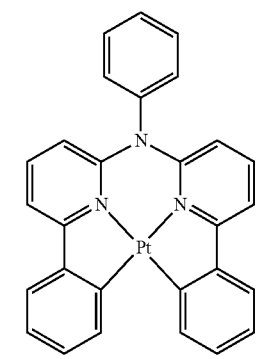 | US20060182992<br>US20070103060 |
| Cu complexes | 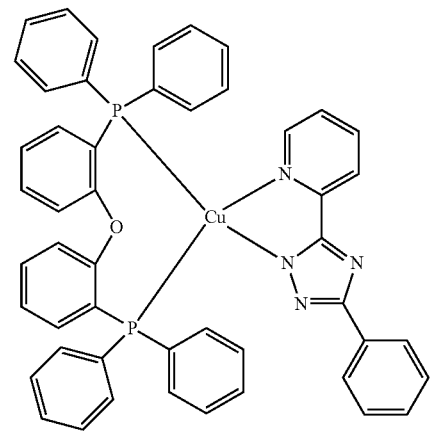 | WO2009000673 |
| | 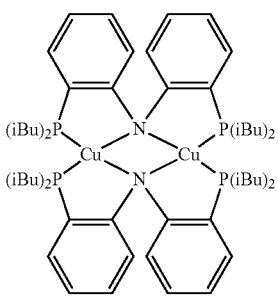 | US20070111026 |

TABLE 2-continued
| MATERIAL | EXAMPLES OF MATERIAL | PUBLICATIONS |
|---|---|---|
| Gold complexes | 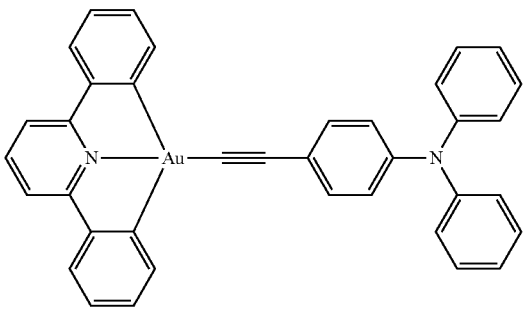 | Chem. Commun. 2906 (2005) |
| Rhenium(III) complexes | 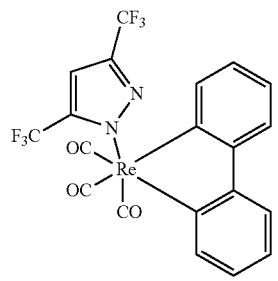 | Inorg. Chem. 42, 1248 (2003) |
| Osmium(II) complexes | 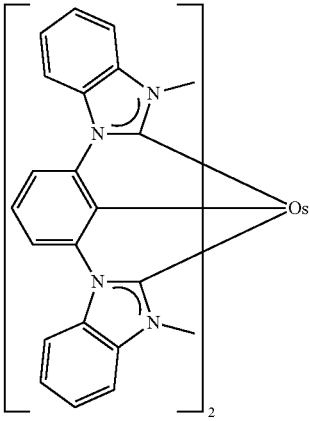 | U.S. Pat. No. 7,279,704 |
| Deuterated organometallic complexes | | US20030138657 |
| Organometallic complexes with two or more metal centers | | US20030152802 |
| | 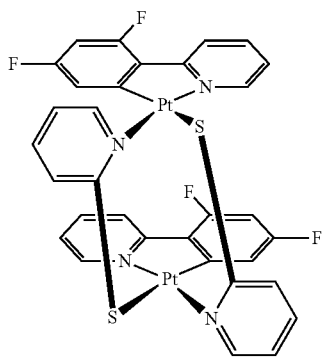 | U.S. Pat. No. 7,090,928 |

TABLE 2-continued
| MATERIAL | EXAMPLES OF MATERIAL | PUBLICATIONS |
|---|---|---|
| | Blue dopants | |
| Iridium(III) organometallic complexes | 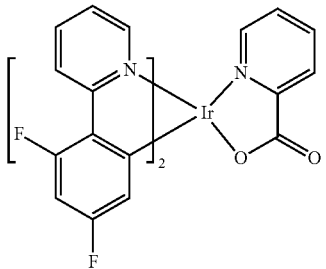 | WO2002002714 |
| | 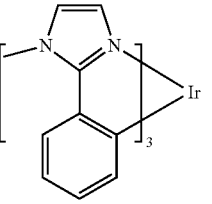 | WO2006009024 |
| | 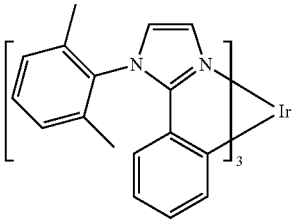 | US20060251923 US20110057559 US20110204333 |
| | 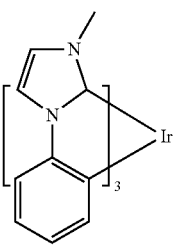 | U.S. Pat. No. 7,393,599, WO2006056418, US20050260441, WO2005019373 |
| | 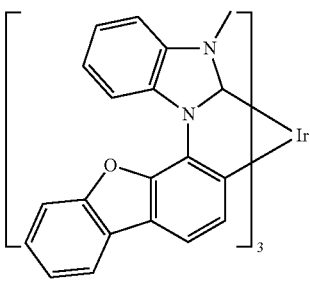 | U.S. Pat. No. 7,534,505 |

TABLE 2-continued
| MATERIAL | EXAMPLES OF MATERIAL | PUBLICATIONS |
|---|---|---|
| | 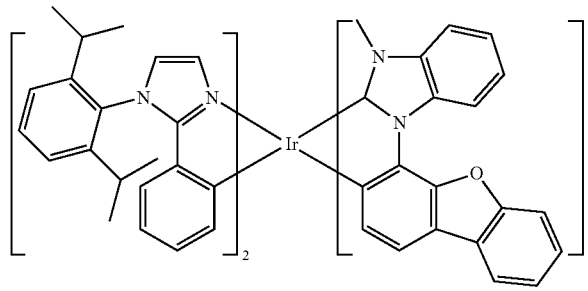 | WO2011051404 |
| | 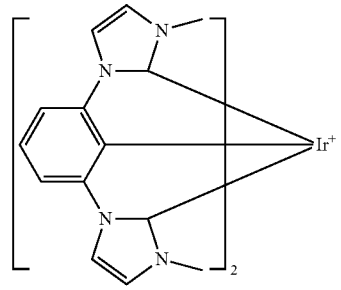 | U.S. Pat. No. 7,445,855 |
| | 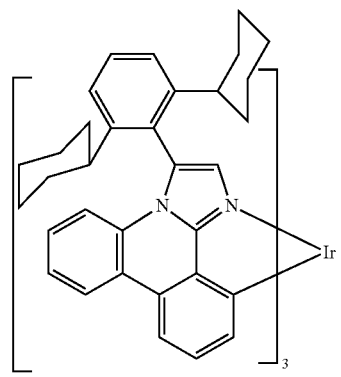 | US20070190359, US20080297033 US20100148663 |
| | 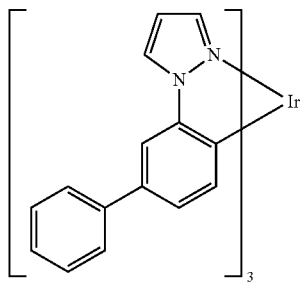 | U.S. Pat. No. 7,338,722 |
| | 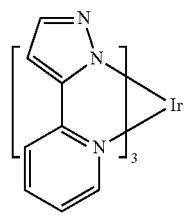 | US20020134984 |

| MATERIAL | EXAMPLES OF MATERIAL | PUBLICATIONS |
|---|---|---|
| | 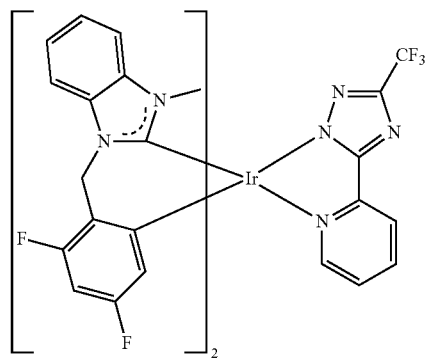 | Angew. Chem. Int. Ed. 47, 4542 (2008) |
| | 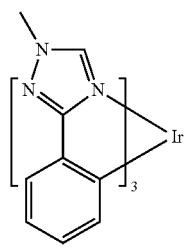 | Chem. Mater. 18, 5119 (2006) |
| | 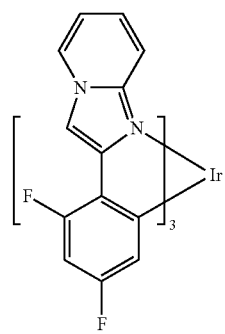 | Inorg. Chem. 46, 4308 (2007) |
| | 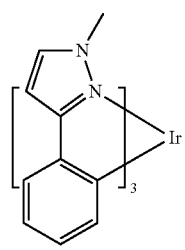 | WO2005123873 |
| | 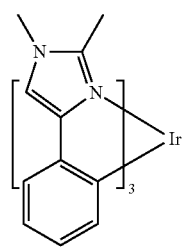 | WO2005123873 |

TABLE 2-continued
| MATERIAL | EXAMPLES OF MATERIAL | PUBLICATIONS |
|---|---|---|
| | 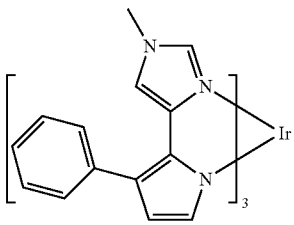 | WO2007004380 |
| | 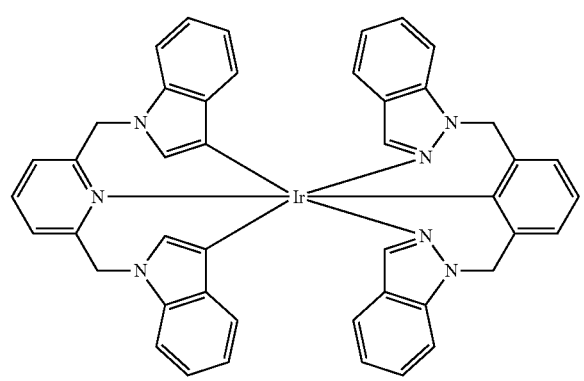 | WO2006082742 |
| Osmium(II) complexes | 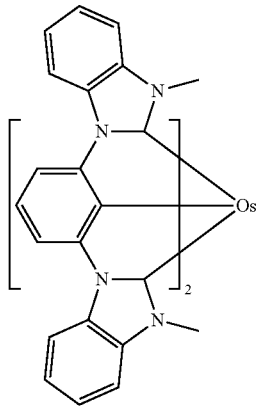 | U.S. Pat. No. 7,279,704 |
| | 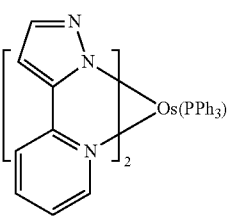 | Organometallics 23, 3745 (2004) |
| Gold complexes | 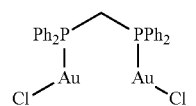 | Appl. Phys. Lett. 74,1361 (1999) |
| Platinum(II) complexes | 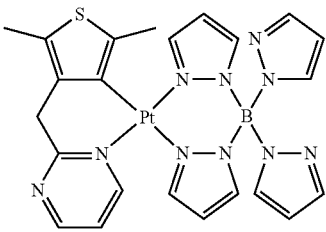 | WO2006098120, WO2006103874 |

| MATERIAL | EXAMPLES OF MATERIAL | PUBLICATIONS |
|---|---|---|
| Pt tetradentate complexes with at least one metal-carbene bond | 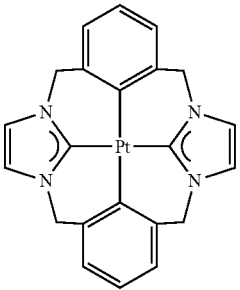 | U.S. Pat. No. 7,655,323 |
| Exciton/hole blocking layer materials | | |
| Bathocuprine compounds (e.g., BCP, BPhen) | 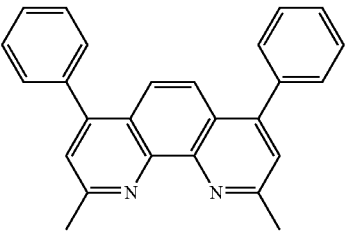 [SMILES: Cc1cc(-c2ccccc2)c2ccc3c(-c4ccccc4)cc(C)nc3c2n1] | Appl. Phys. Lett. 75, 4 (1999) |
| | 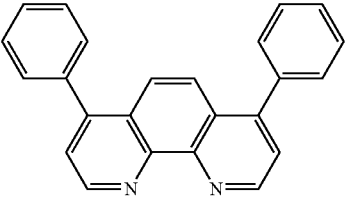 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 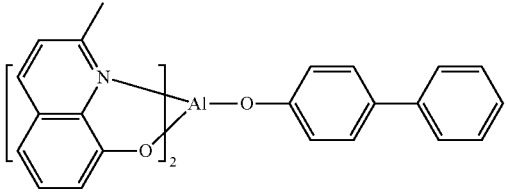 | Appl. Phys. Lett. 81, 162 (2002) |
| 5-member ring electron deficient heterocycles such as triazole, oxadiazole, imidazole, benzoimidazole | 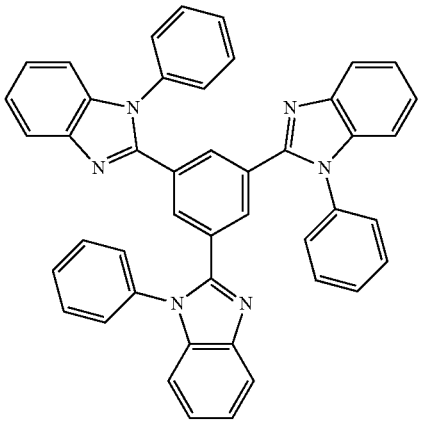 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 2-continued
| MATERIAL | EXAMPLES OF MATERIAL | PUBLICATIONS |
|---|---|---|
| Triphenylene compounds | 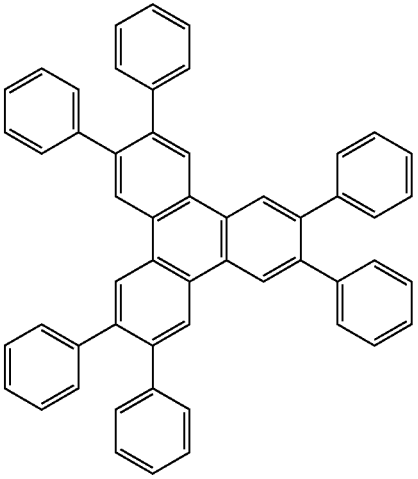 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 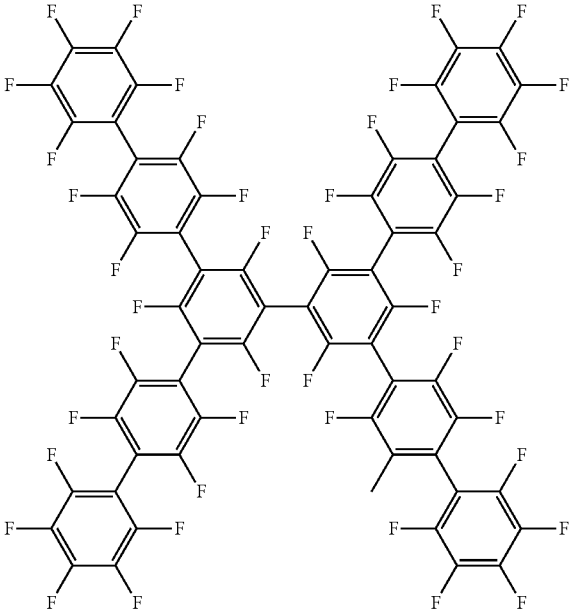 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 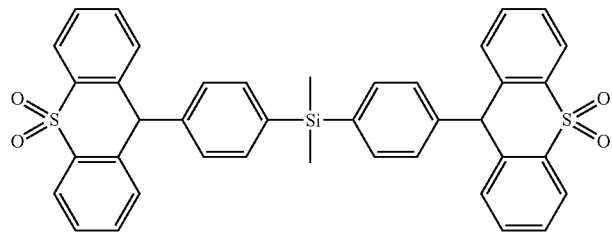 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 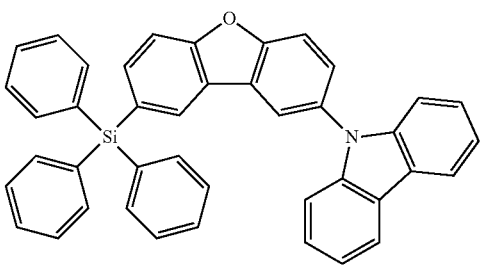 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 2-continued
| MATERIAL | EXAMPLES OF MATERIAL | PUBLICATIONS |
|---|---|---|
| Aza-carbazoles | 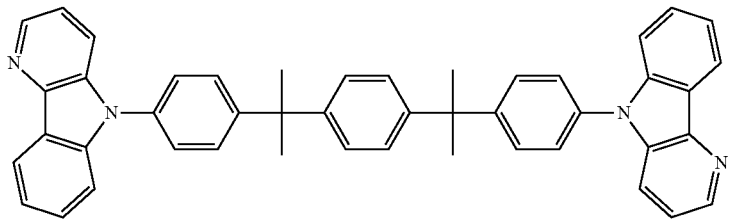 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 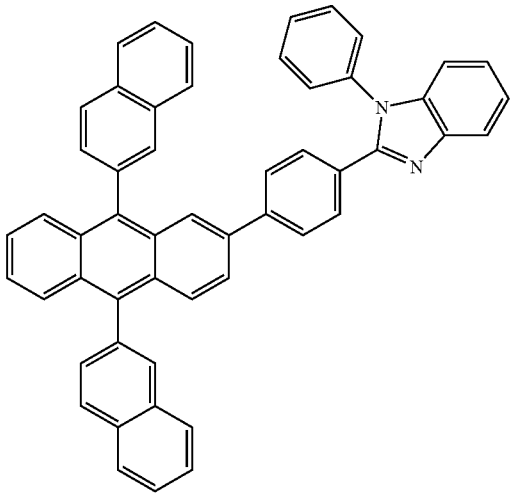 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| Aza triphenylene derivatives | 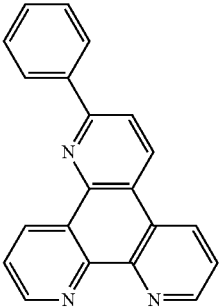 [SMILES: c1ccc(-c2ccc3c4cccnc4c4ncccc4c3n2)cc1] | US20090179554<br>US20090115316 |
| Anthracene-benzothiazole compounds | 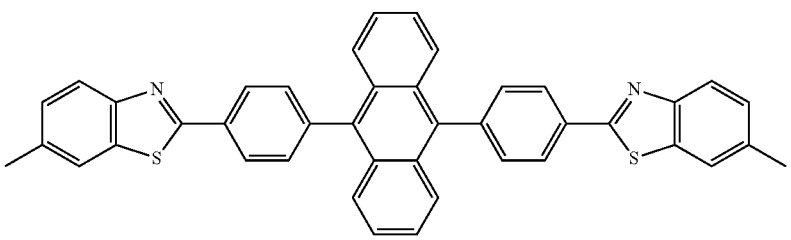 | Appl. Phys. Lett. 89, 063504 (2006) |
| Metal 8-hydroxyquinolates (e.g., $Alq_3$, $Zrq_4$) | 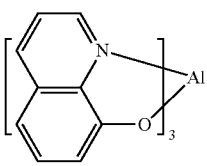 | Appl. Phys. Lett. 51, 913 (1987)<br>U.S. Pat. No. 7,230,107 |

TABLE 2-continued

| MATERIAL | EXAMPLES OF MATERIAL | PUBLICATIONS |
|---|---|---|
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 2-continued

| MATERIAL | EXAMPLES OF MATERIAL | PUBLICATIONS |
|---|---|---|
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g. C60) | | US20090101870 |
| Triazine complexes | | US20040036077 |

TABLE 2-continued

| MATERIAL | EXAMPLES OF MATERIAL | PUBLICATIONS |
|---|---|---|
| Zn (N^N) complexes | 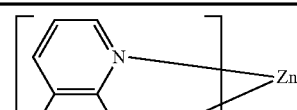 | U.S. Pat. No. 6,528,187 |

EXPERIMENTAL

Chemical abbreviations used throughout this document are as follows: SPhos is dicyclohexyl(2',6'-dimethoxy-[1,1'-biphenyl]-2-yl)phosphine, $Pd_2(dba)_3$ is tri(dibenzylideneacetone dipalladium(0), and DCM is dichloromethane.

Example 1

Synthesis of Compound 15

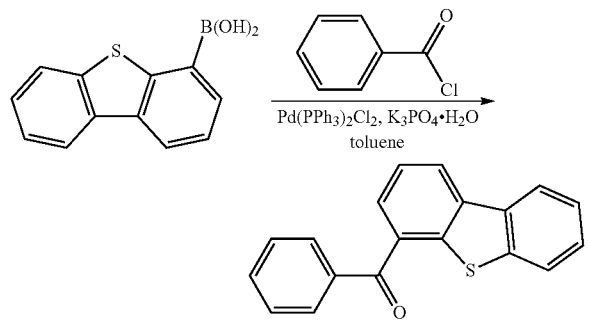

A solution of dibenzo[b,d]thiophen-4-ylboronic acid (8.0 g, 35 mmol), benzoyl chloride (6.1 mL, 53 mmol), Pd(PPh₃)₂Cl₂ (0.62 g, 0.877 mmol), and K₃PO₄·H₂O (12.12 g, 53 mmol) in toluene (100 mL) was refluxed under nitrogen for 2 hours. After cooling to room temperature, it was filtered through a plug of Celite® (Imerys Filtration, San Jose, Calif.) and the solvent was evaporated. The residue was purified by column chromatography on silica gel with hexane/DCM (3/1, v/v) as eluent. The crude product was refluxed with hexane and dibenzo[b,d]thiophen-4-yl(phenyl)methanone (4.6 g, 46%) was collected by filtration as a white solid.

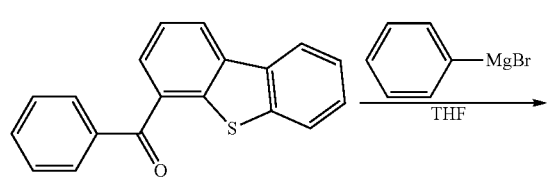

-continued

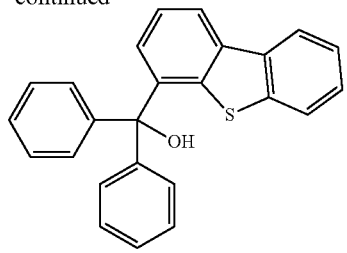

Into a solution of dibenzo[b,d]thiophen-4-yl(phenyl)methanone (4 g, 13.87 mmol) in tetrahydrofuran (200 mL) was added phenylmagnesium bromide (9.25 mL, 27.7 mmol) solution in ether at room temperature. It was heated at 60° C. overnight. After cooling to room temperature, it was quenched with 2 M aqueous HCl solution, extracted with ether, dried over Na₂SO₄, and the solvent was evaporated. The residue was dissolved in dichloromethane and passed through a short plug of silica gel with hexane/DCM (1/1, v/v) as eluent. The crude product was purified by recrystallization from hexane to yield dibenzo[b,d]thiophen-4-yldiphenylmethanol (4.7 g, 92%) as white crystals.

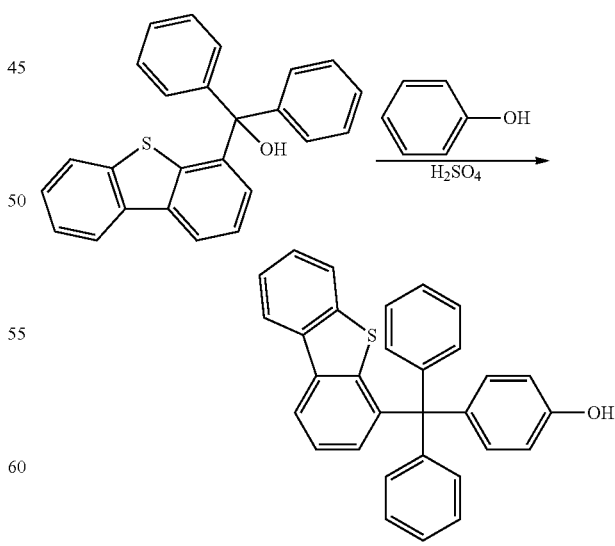

A drop of sulfuric acid was added into a stirred mixture of dibenzo[b,d]thiophen-4-yldiphenylmethanol (3.4 g, 9.28 mmol) and phenol (8.73 g, 93 mmol) at 80° C. The black green solution was stirred for 1 hour at this temperature. After cooling to room temperature, the solution was dissolved in ether, washed with water, and dried over Na₂SO₄. Upon evaporation of the solvent and excess phenol, the residue was purified by column chromatography on silica gel with hexane/ethyl acetate (9/1, v/v) as eluent to yield 4-(dibenzo[b,d]thiophen-4-yldiphenylmethyl)phenol (3 g, 73.1%) as a white solid.

Into a suspension of 4-(dibenzo[b,d]thiophen-4-yldiphenylmethyl)phenol (3 g, 6.78 mmol) and pyridine (1.094 mL, 13.56 mmol) in DCM (100 mL) was added dropwise a solution of trifluoromethanesulfonic anhydride (1.480 mL, 8.81 mmol) in DCM (20 mL) at 0° C. The solution was allowed to warm to room temperature and stirred overnight. The solution was quenched with a saturated NaHCO₃ solution and dried over Na₂SO₄. Upon evaporation of the solvent, the residue was purified by column chromatography on silica gel with hexane/DCM (9/1, v/v) as eluent to yield 4-(dibenzo[b,d]thiophen-4-yldiphenylmethyl)phenyl trifluoromethanesulfonate (3.5 g, 90% yield) as a white powder.

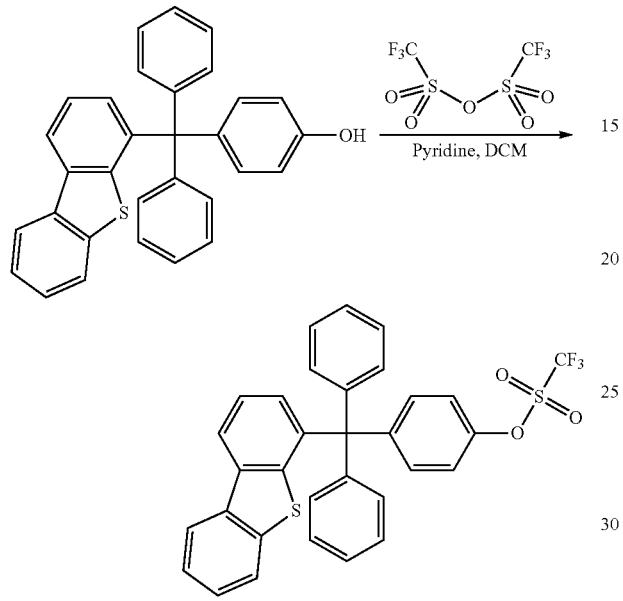

Compound 15

A solution of 4-(dibenzo[b,d]thiophen-4-yldiphenylmethyl)phenyl trifluoromethanesulfonate (3.5 g, 6.09 mmol), 9H-carbazole (1.222 g, 7.31 mmol), Pd₂(dba)₃ (0.112 g, 0.122 mmol), SPhos (0.100 g, 0.244 mmol) and sodium tert-butoxide (1.171 g, 12.18 mmol) in m-xylene (100 ml) was heated at 140° C. overnight. After cooling to room temperature, it was diluted with DCM, washed with aqueous NH₄Cl solution, and dried over Na₂SO₄. Upon evaporation of the solvent, the residue was passed through a column of silica gel with hexane/DCM (9/1, v/v) as eluent. The crude product was stirred with methanol to yield Compound 15 (1.1 g, 31%) as white crystals.

Computational Example

Compounds were subjected to computational investigation using the Gaussian G09, Revision C.01 at the B3LYP/6-31g(d) functional and basis set to evaluate the energy levels of selected compounds. The computational results of HOMO/LUMO and triplet (T1) energy levels of comparative compound CC-1 and some inventive compounds were presented in TABLE 3.

TABLE 3

| Compound | Chemical Structure | HOMO (eV) | LUMO (eV) | T1 (eV) |
|---|---|---|---|---|
| CC-1 | 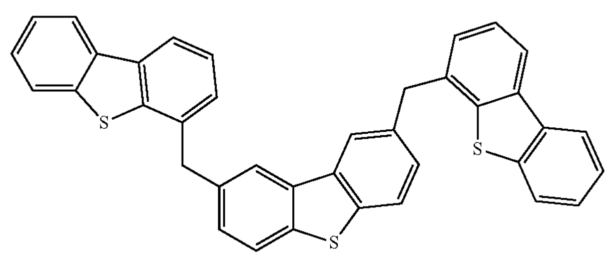 [SMILES: c1ccc2c(c1)sc1c(Cc3ccc4sc5ccc(Cc6cccc7c6sc6ccccc67)cc5c4c3)cccc12] | −5.63 | −1.01 | 3.12 |

TABLE 3-continued

| Compound | Chemical Structure | HOMO (eV) | LUMO (eV) | T1 (eV) |
|---|---|---|---|---|
| Compound 13 | 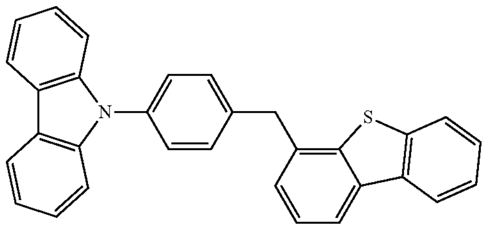 [SMILES: c1ccc2c(c1)sc1c(Cc3ccc(-n4c5ccccc5c5ccccc54)cc3)cccc12] | −5.26 | −1.02 | 3.16 |
| Compound 15 | 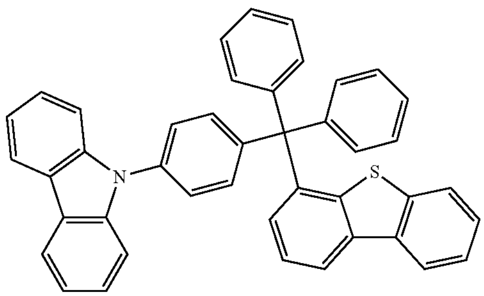 [SMILES: c1ccc(C(c2ccccc2)(c2ccc(-n3c4ccccc4c4ccccc43)cc2)c2cccc3c2sc2ccccc23)cc1] | −5.28 | −0.98 | 3.15 |
| Compound 37 | 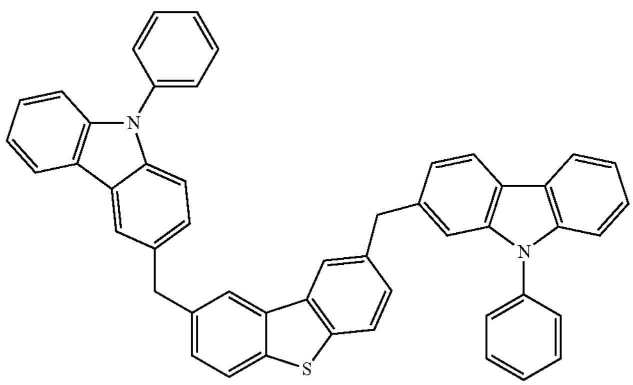 [SMILES: c1ccc(-n2c3ccccc3c3cc(Cc4ccc5sc6ccc(Cc7ccc8c9ccccc9n(-c9ccccc9)c8c7)cc6c5c4)ccc32)cc1] | −5.26 | −0.87 | 3.11 |
| Compound 385 | 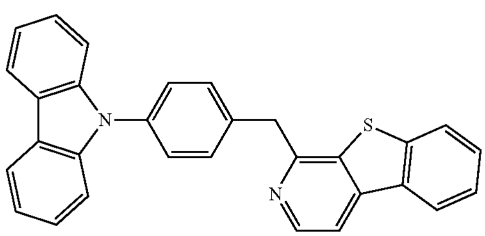 [SMILES: c1ccc2c(c1)sc1c(Cc3ccc(-n4c5ccccc5c5ccccc54)cc3)nccc12] | −5.24 | −1.48 | 3.18 |
| Compound 436 | 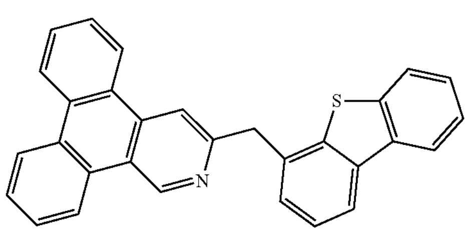 [SMILES: c1ccc2c(c1)sc1c(Cc3cc4c5ccccc5c5ccccc5c4cn3)cccc12] | −5.78 | −1.28 | 2.88 |

TABLE 3-continued

| Compound | Chemical Structure | HOMO (eV) | LUMO (eV) | T1 (eV) |
|---|---|---|---|---|
| Compound 445 | 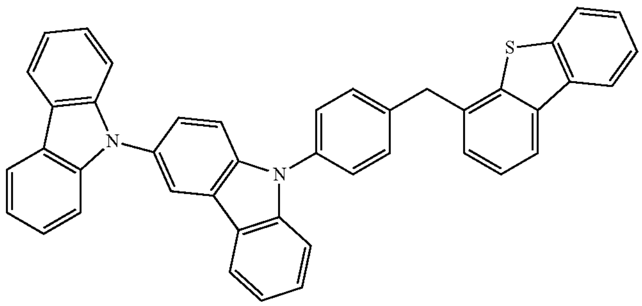 [SMILES: c1ccc2c(c1)sc1c(Cc3ccc(-n4c5ccccc5c5cc(-n6c7ccccc7c7ccccc76)ccc54)cc3)cccc12] | −5.09 | −1.09 | 3.16 |

A comparison between Compound 13 and CC-1 found that introducing a carbazole moiety in Compound 13 raised its HOMO level by 0.37 eV higher than that of CC-1, while LUMO and T1 are left at the same levels. As shown in Table 3, this invention offers a very convenient way to independently adjust the HOMO and LUMO levels of the host materials by introducing various building blocks. This is particularly useful to fine-tune the charge transport properties in OLED devices.

Device Example

The structures of the materials used in the device examples are shown below:

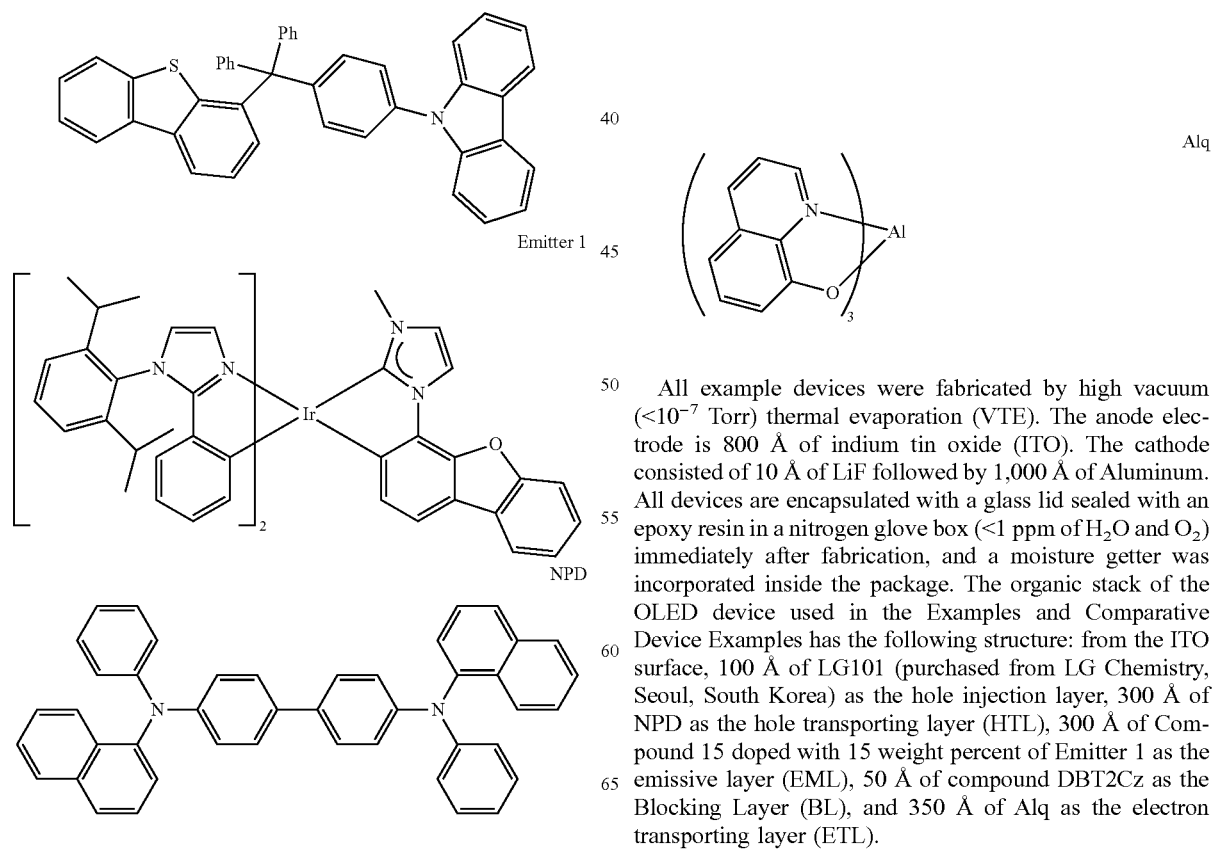

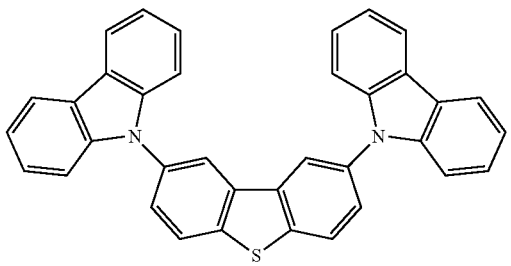

All example devices were fabricated by high vacuum ($<10^{-7}$ Torr) thermal evaporation (VTE). The anode electrode is 800 Å of indium tin oxide (ITO). The cathode consisted of 10 Å of LiF followed by 1,000 Å of Aluminum. All devices are encapsulated with a glass lid sealed with an epoxy resin in a nitrogen glove box (<1 ppm of $H_2O$ and $O_2$) immediately after fabrication, and a moisture getter was incorporated inside the package. The organic stack of the OLED device used in the Examples and Comparative Device Examples has the following structure: from the ITO surface, 100 Å of LG101 (purchased from LG Chemistry, Seoul, South Korea) as the hole injection layer, 300 Å of NPD as the hole transporting layer (HTL), 300 Å of Compound 15 doped with 15 weight percent of Emitter 1 as the emissive layer (EML), 50 Å of compound DBT2Cz as the Blocking Layer (BL), and 350 Å of Alq as the electron transporting layer (ETL).

TABLE 4

| | | | | | | | At 1000 nits | |
|---|---|---|---|---|---|---|---|---|
| Device Examples | HTL | Host | Emitter | $\lambda_{max}$ (nm) | CIE x | CIE y | V (V) | LE (cd/A) | EQE (%) |
| Device 1 | NPD | Compound 15 | Emitter 1 | 464 | 0.156 | 0.270 | 6.1 | 18.8 | 10.4 |

Table 4 provides a summary of the device data. The luminous efficiency (LE), external quantum efficiency (EQE), and power efficiency (PE) were measured at 1000 nits. Device 1 showed blue emission from Emitter 1 with an emission peak wavelength at 464 nm. The EQE was measured at 10.4% at 1000 nits. This result shows that the inventive compound has high enough triplet to host blue emission and achieve high device efficiency.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having formula I:

A-L-B  (I);

wherein A and B are each different selections selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;

wherein A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

wherein L is selected from the group consisting of alkyl, cycloalkyl, substituted alkyl, and substituted cycloalkyl; and wherein L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

2. The compound of claim 1, wherein A including optional substituents and B including optional substituents are different.

3. The compound of claim 1, wherein the compound further comprises C;

wherein C is selected from the group consisting of N-phenyl carbazole, dibenzofuran, dibenzothiophene, triphenylene, aza-(N-phenyl carbazole), aza-dibenzofuran, aza-dibenzothiophene, and aza-triphenylene;

wherein C can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein C is connected to A or B by L'; wherein L' is selected from the group consisting of alkyl, cycloalkyl, substituted alkyl, and substituted cycloalkyl; and wherein L' can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

4. The compound of claim 3, wherein C is a different selection from the group consisting of N-phenyl carbazole, dibenzofuran, dibenzothiophene, triphenylene, aza-(N-phenyl carbazole), aza-dibenzofuran, aza-dibenzothiophene, and aza-triphenylene than A and B.

5. The compound of claim 3, wherein A, B, and C have no further substitution.

6. The compound of claim 3, wherein no more than one of A, B, and C is aza-(N-phenyl carbazole), aza-dibenzofuran, aza-dibenzothiophene, or aza-triphenylene.

7. The compound of claim 3 wherein L' has from 1 to 24 carbon atoms.

8. The compound of claim 3, wherein L' is selected from the group consisting of

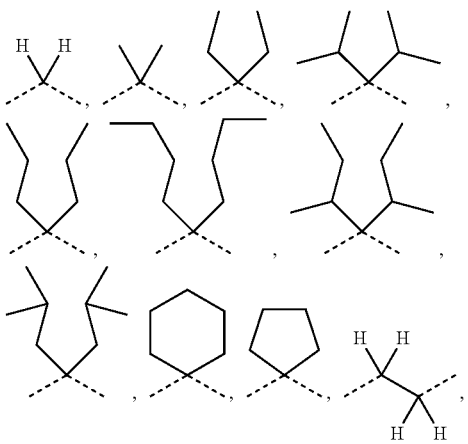

181
-continued
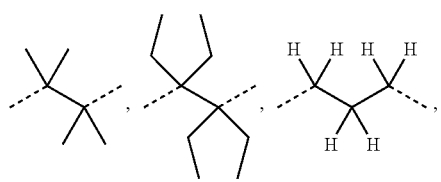
182
-continued
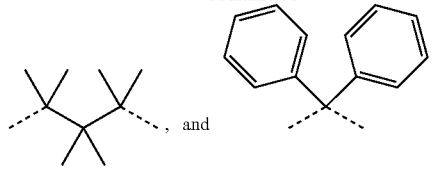, and
and wherein the dash lines represent a direct bond between L' and C, and L' and A or B.
9. The compound of claim 3, wherein the compound is selected from the group consisting of:
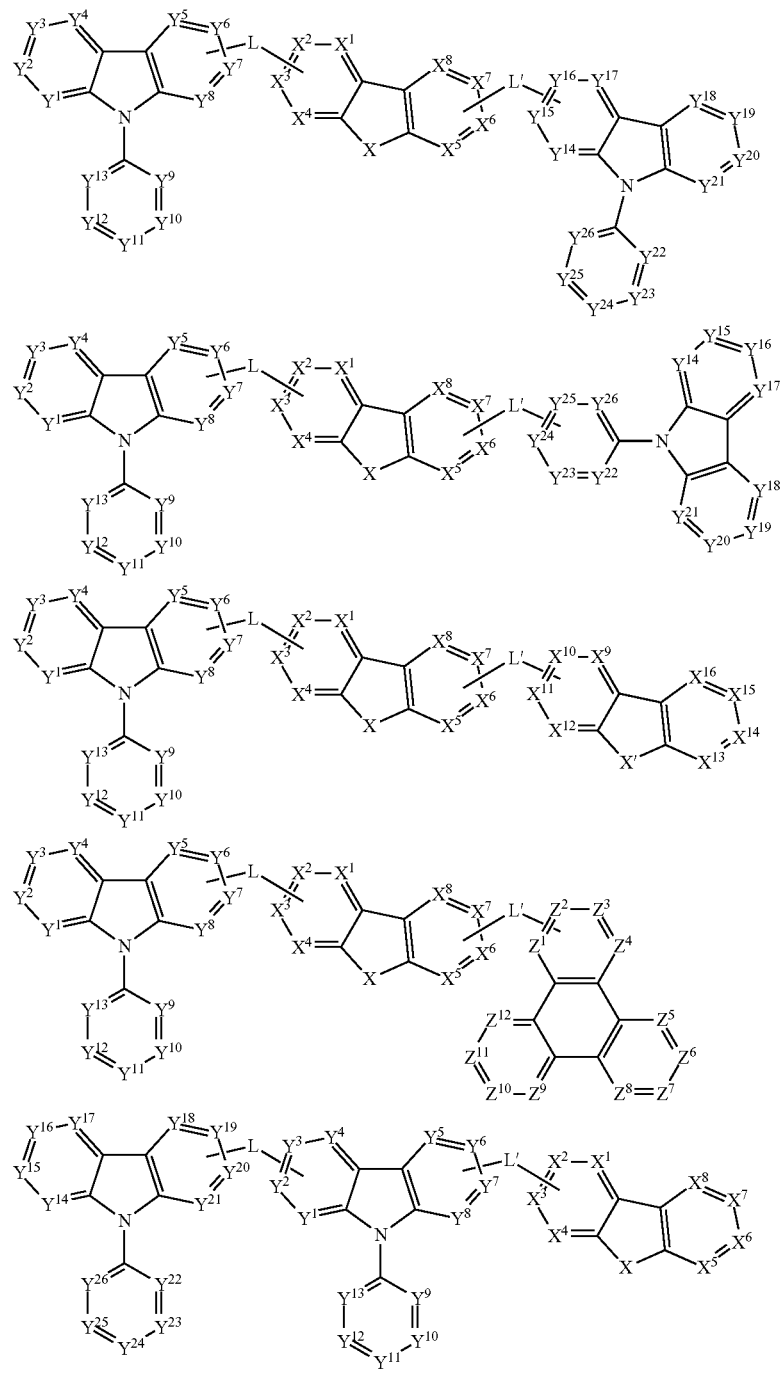

-continued
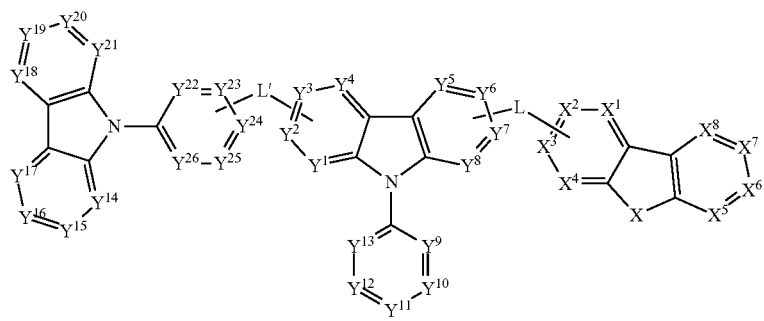
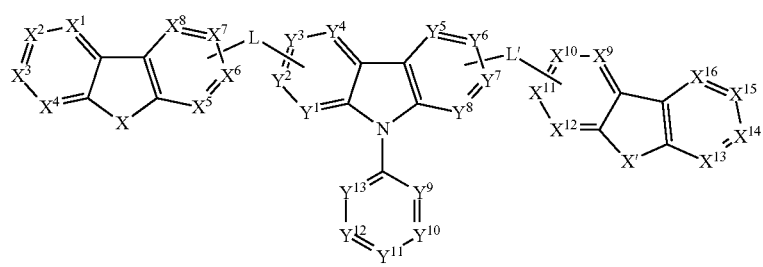
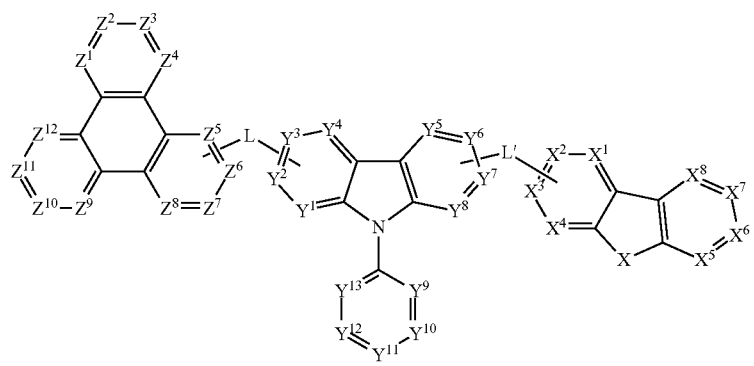
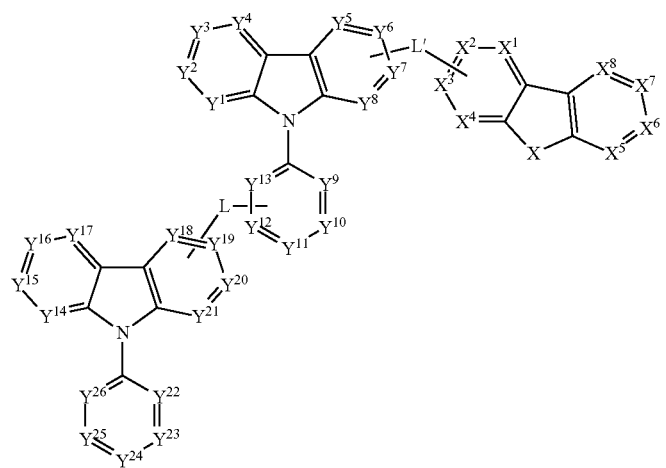

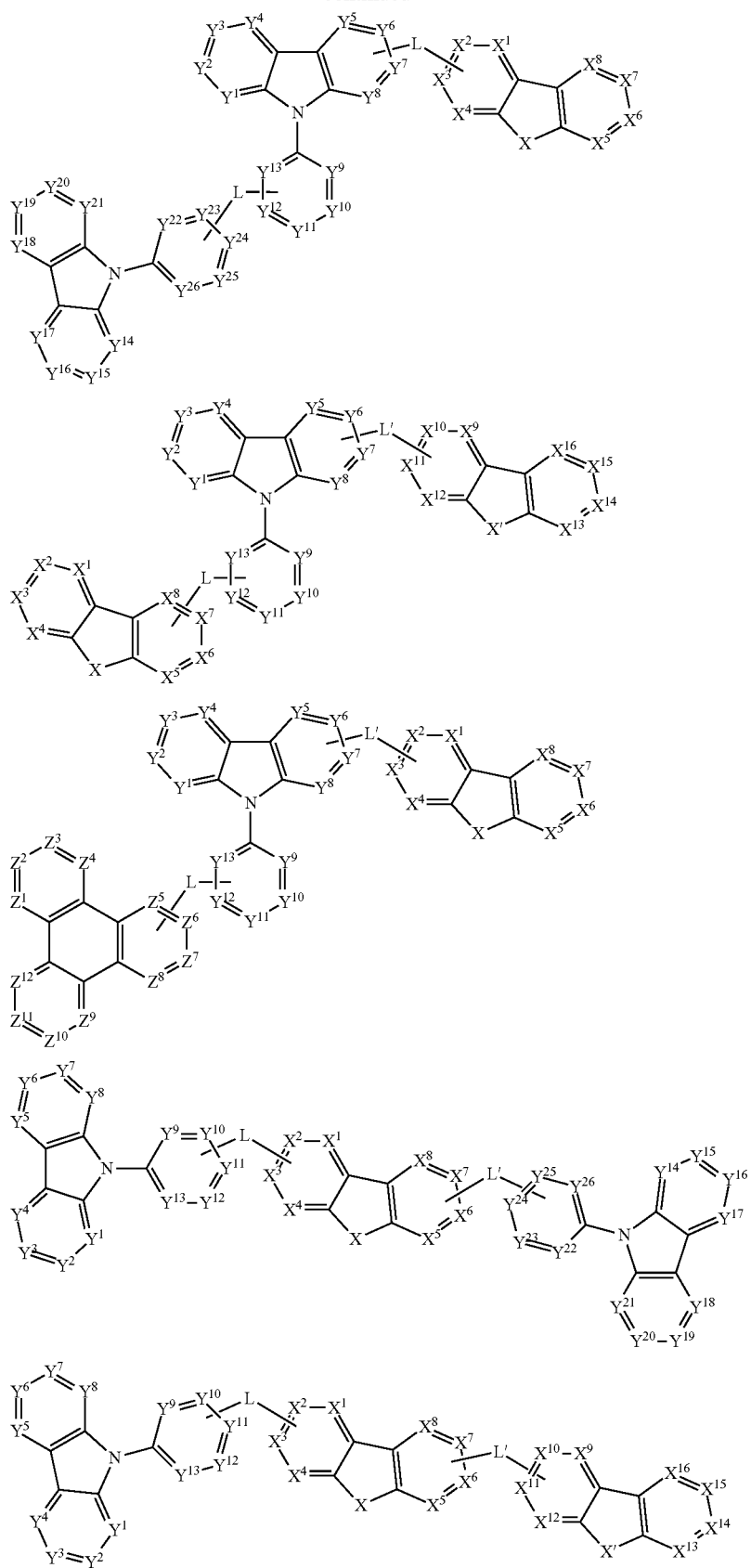

-continued
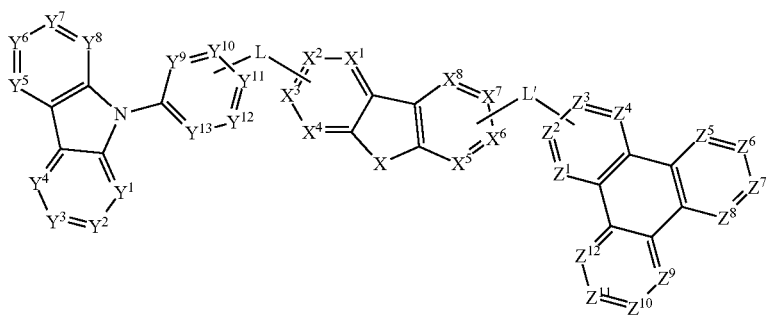
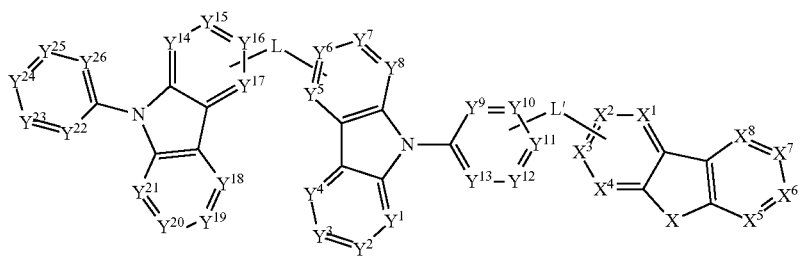
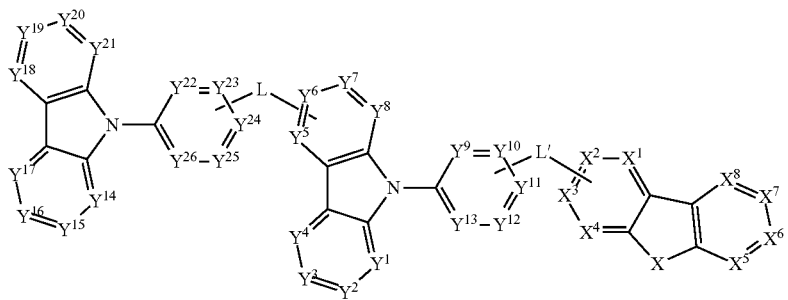
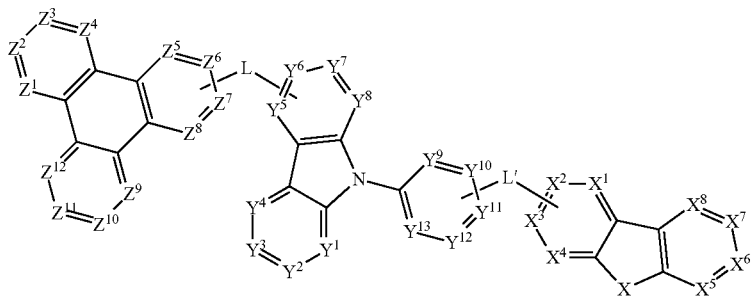
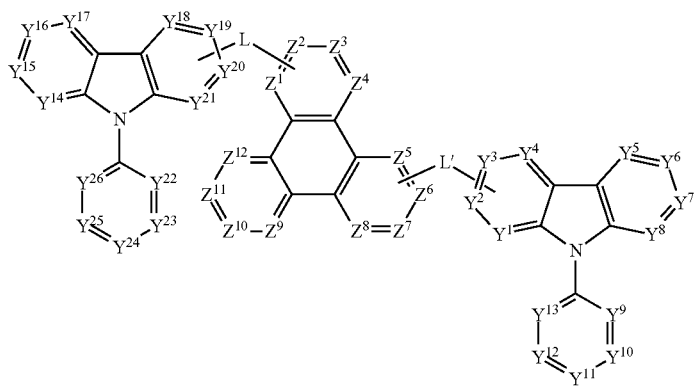

-continued
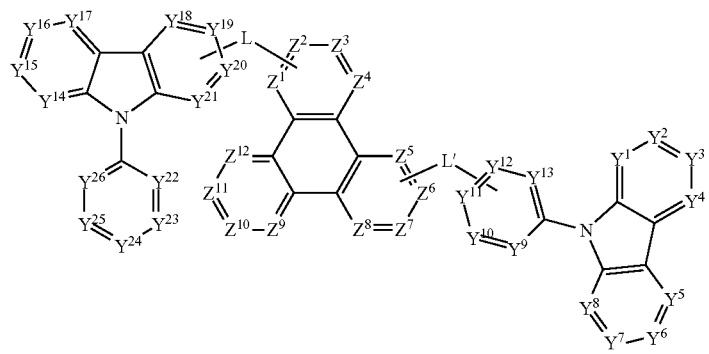
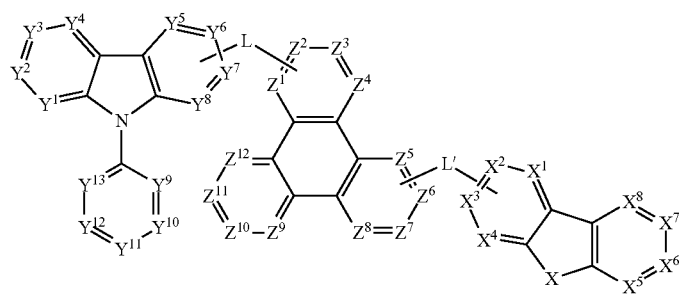
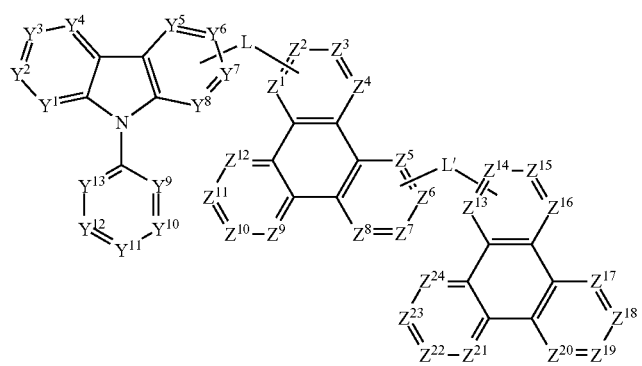
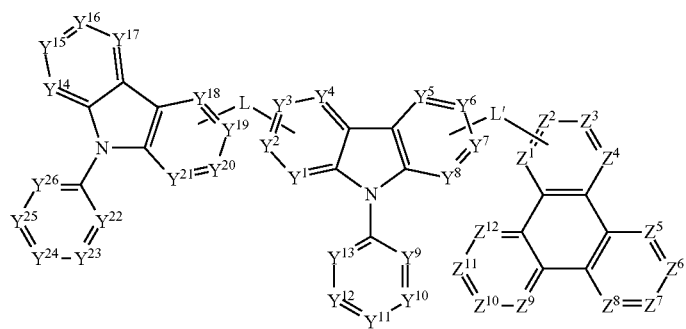
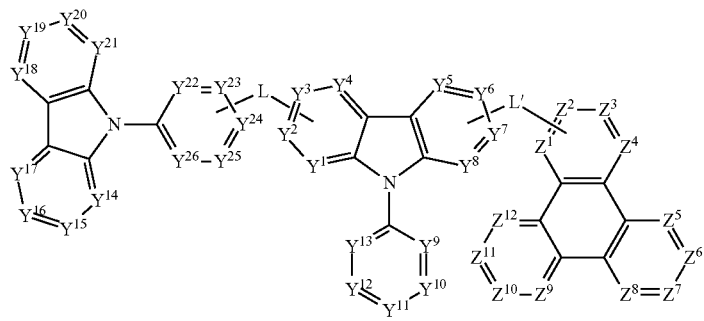

-continued
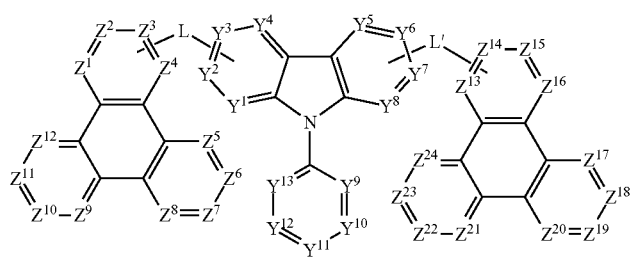
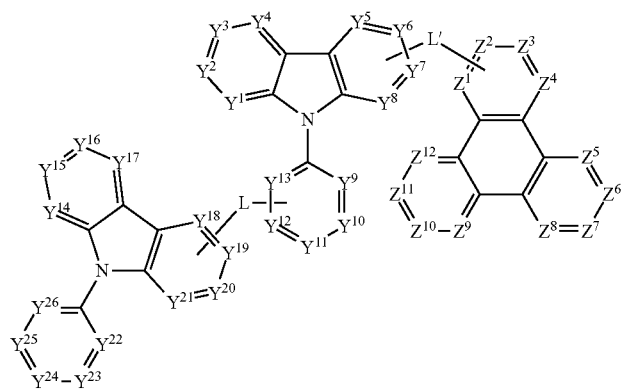
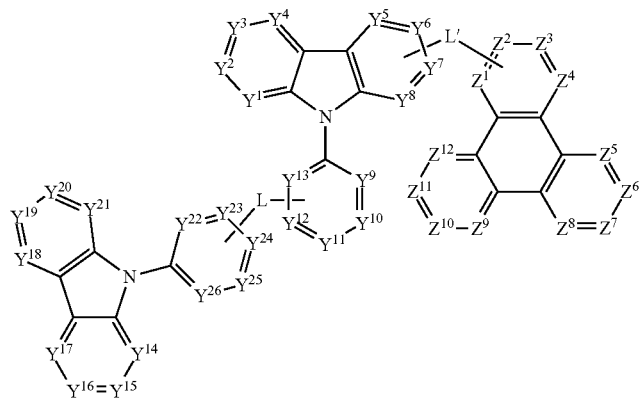
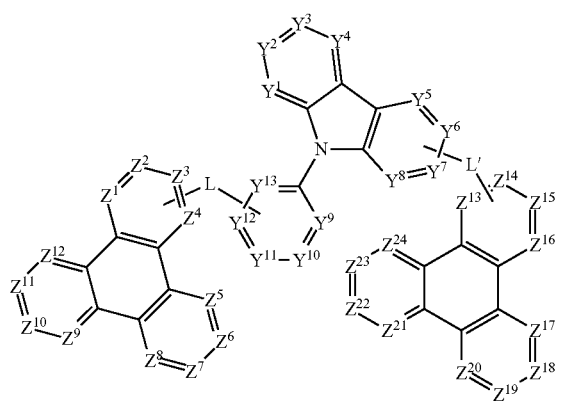

-continued
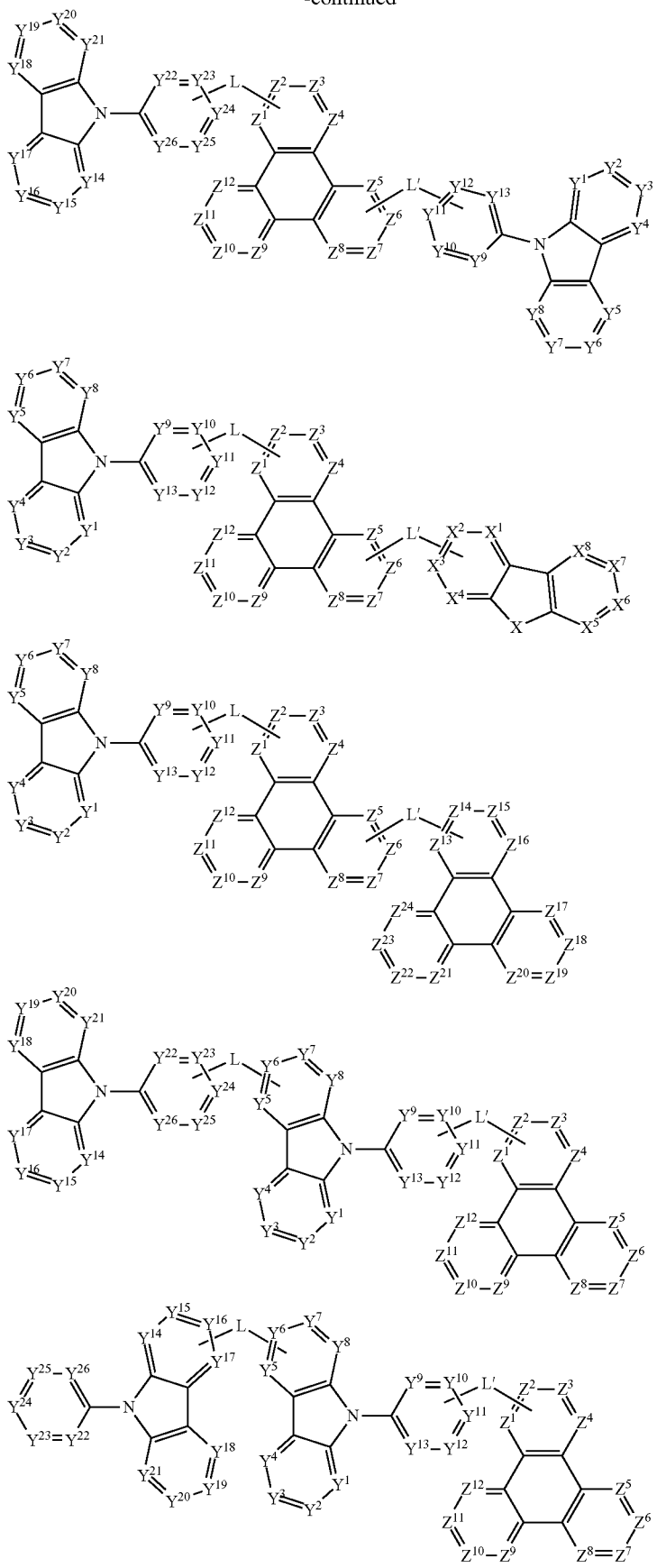

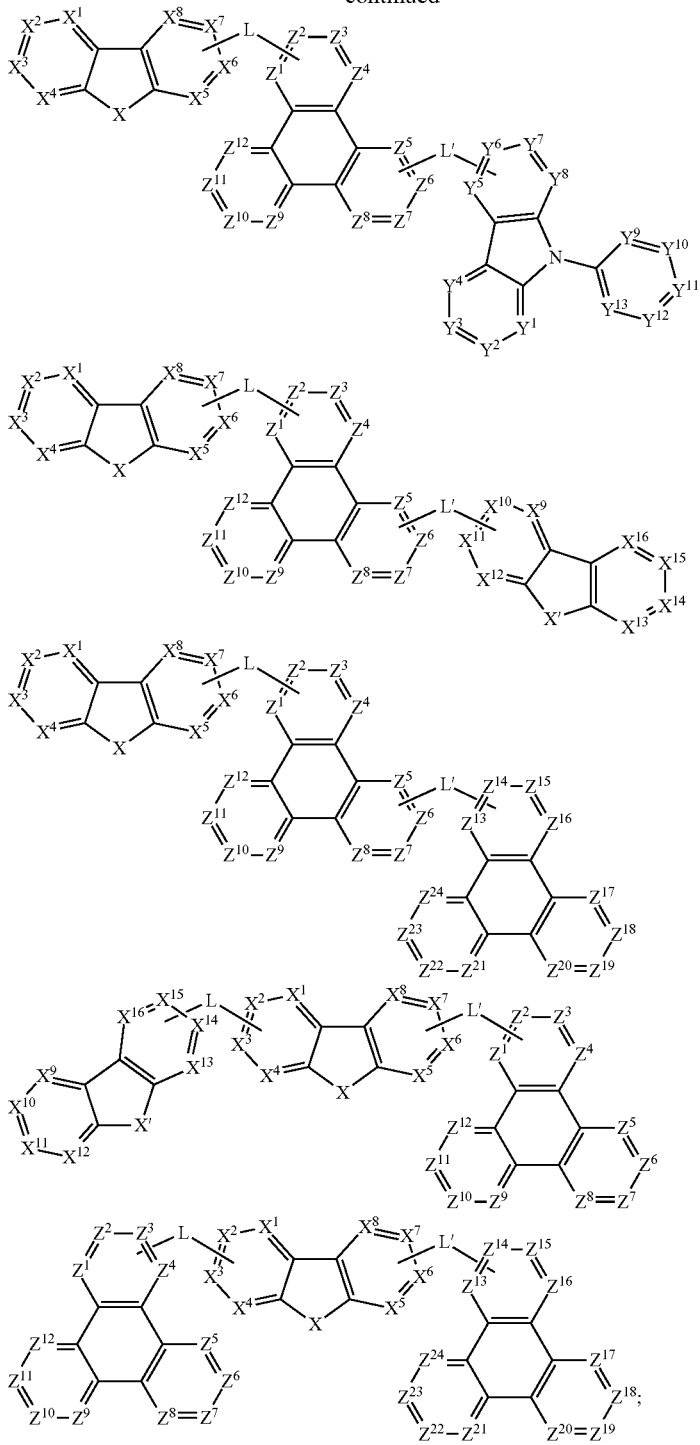

wherein X is O or S;
wherein $X^1$ to $X^{16}$, $Y^1$ to $Y^{26}$, and $Z^1$ to $Z^{24}$ are each independently selected from the group consisting of CR and N; and
wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

10. The compound of claim 1, wherein A and B have no further substitution.

11. The compound of claim 1, wherein A and B are each independently selected from the group consisting of N-phenyl carbazole, aza-(N-phenyl carbazole), dibenzofuran, dibenzothiophene, and triphenylene.

12. The compound of claim 1, wherein A is selected from the group consisting of N-phenyl carbazole, dibenzofuran, dibenzothiophene, and triphenylene; and B is selected from the group consisting of aza-(N-phenyl carbazole), aza-dibenzofuran, aza-dibenzothiophene, and aza-triphenylene.

13. The compound of claim 1, wherein L has from 1 to 24 carbon atoms.

14. The compound of claim 1, wherein L is selected from the group consisting of

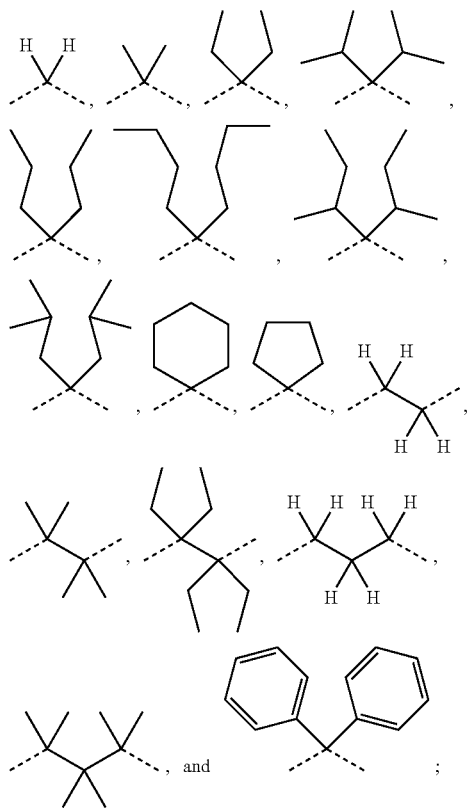

and wherein the dash lines represent a direct bond between L and A, and L and B.

15. The compound of claim 1, wherein A or B is (9-carbazolyl)-(N-phenyl-carbazole).

16. The compound of claim 1, wherein the aza-(N-phenyl carbazole) is selected from the group consisting of N-pyridyl carbazole, N-pyrazinyl carbazole, and N-triazinyl carbazole.

17. The compound of claim 1, wherein the compound is selected from the group consisting of:

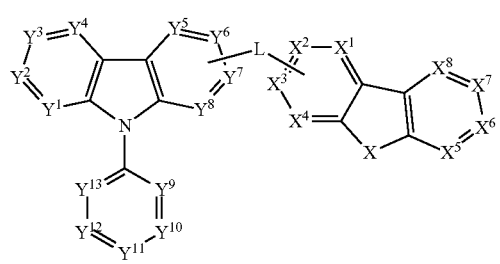

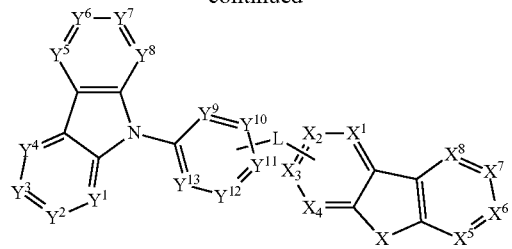

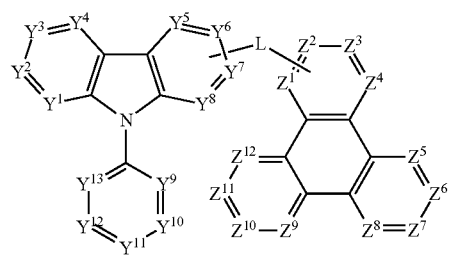

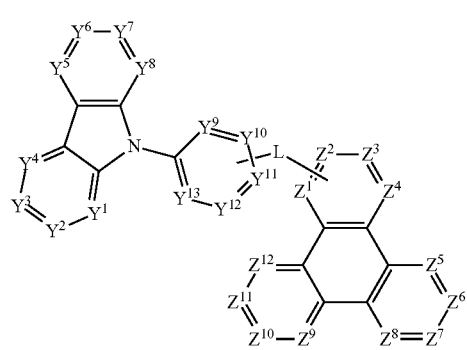

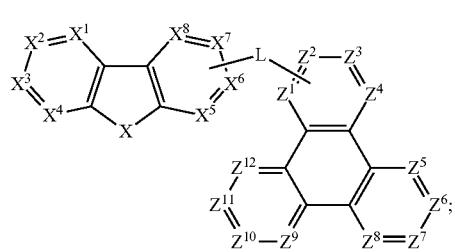

wherein X is O or S;

wherein $X^1$ to $X^8$, $Y^1$ to $Y^{13}$, and $Z^1$ to $Z^{12}$ are each independently selected from the group consisting of CR and N; and wherein R is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent R can optionally join to form a fused ring.

18. The compound of claim 1, wherein the compound is selected from the group consisting of compound 1 to compound 459 listed below:

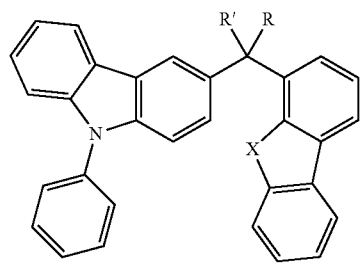
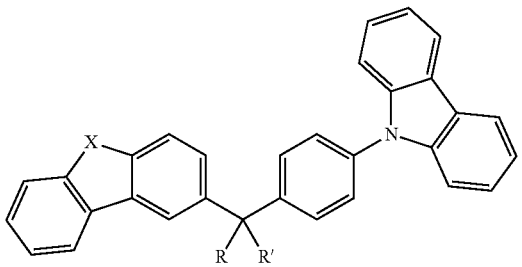

Compound 1 R = R' = H, X = S
Compound 2 R = R' = CH₃, X = S
Compound 3 R = R' = Ph, X = S
Compound 4 R = R' = H, X = O
Compound 5 R = R' = CH₃, X = O
Compound 6 R = R' = Ph, X = O Compound 7 R = R' = H, X = S
Compound 8 R = R' = CH₃, X = S
Compound 9 R = R' = Ph, X = S
Compound 10 R = R' = H, X = O
Compound 11 R = R' = CH₃, X = O
Compound 12 R = R' = Ph, X = O

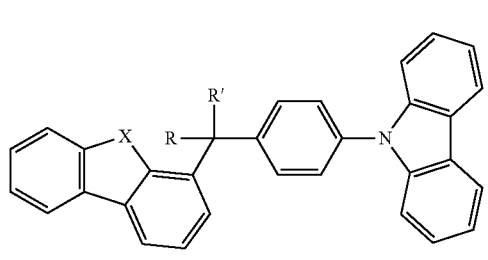
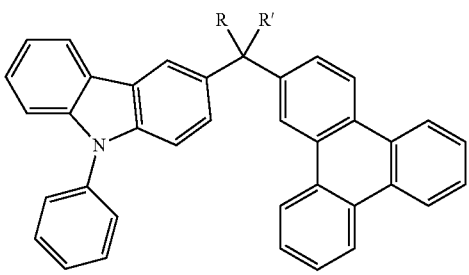

Compound 13 R = R' = H, X = S
Compound 14 R = R' = CH₃, X = S
Compound 15 R = R' = Ph, X = S
Compound 16 R = R' = H, X = O
Compound 17 R = R' = CH₃, X = O
Compound 18 R = R' = Ph, X = O Compound 19 R = R' = H
Compound 20 R = R' = CH₃
Compound 21 R = R' = Ph

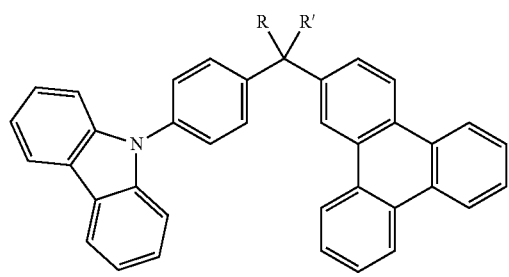
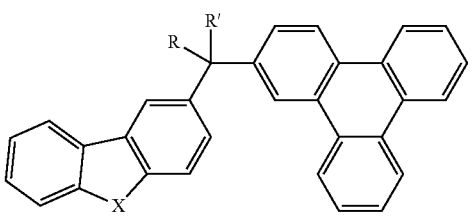

Compound 22 R = R' = H
Compound 23 R = R' = CH₃
Compound 24 R = R' = Ph

Compound 25 R = R' = H, X = S
Compound 26 R = R' = CH₃, X = S
Compound 27 R = R' = Ph, X = S
Compound 28 R = R' = H, X = O
Compound 29 R = R' = CH₃, X = O
Compound 30 R = R' = Ph, X = O

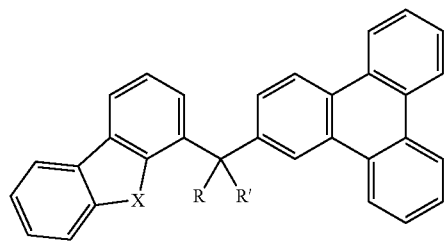

Compound 31 R = R' = H, X = S
Compound 32 R = R' = CH₃, X = S
Compound 33 R = R' = Ph, X = S
Compound 34 R = R' = H, X = O
Compound 35 R = R' = CH₃, X = O
Compound 36 R = R' = Ph, X = O -continued

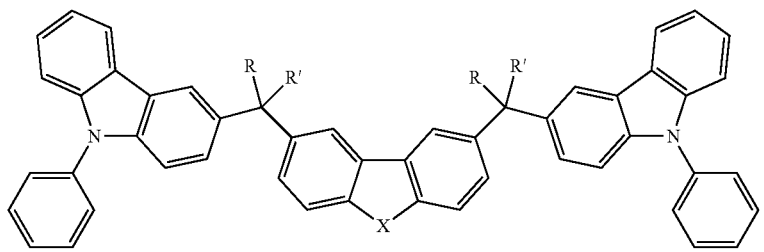

Compound 37 R = R' = H, X = S
Compound 38 R = R' = CH₃, X = S
Compound 39 R = R' = Ph, X = S
Compound 40 R = R' = H, X = O
Compound 41 R = R' = CH₃, X = O
Compound 42 R = R' = Ph, X = O

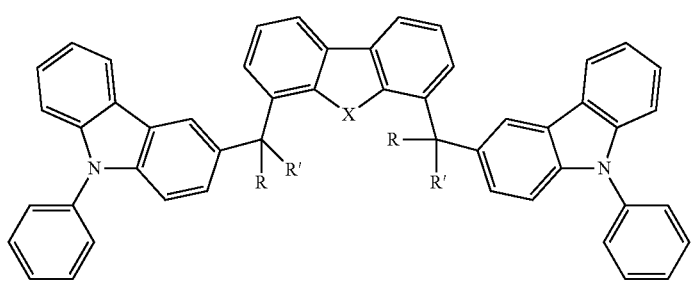

Compound 43 R = R' = H, X = S
Compound 44 R = R' = CH₃, X = S
Compound 45 R = R' = Ph, X = S
Compound 46 R = R' = H, X = O
Compound 47 R = R' = CH₃, X = O
Compound 48 R = R' = Ph, X = O

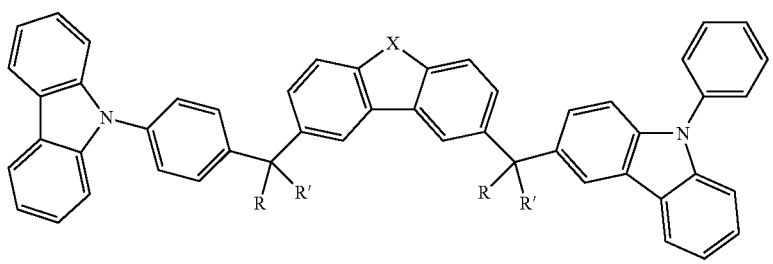

Compound 49 R = R' = H, X = S
Compound 50 R = R' = CH₃, X = S
Compound 51 R = R' = Ph, X = S
Compound 52 R = R' = H, X = O
Compound 53 R = R' = CH₃, X = O
Compound 54 R = R' = Ph, X = O

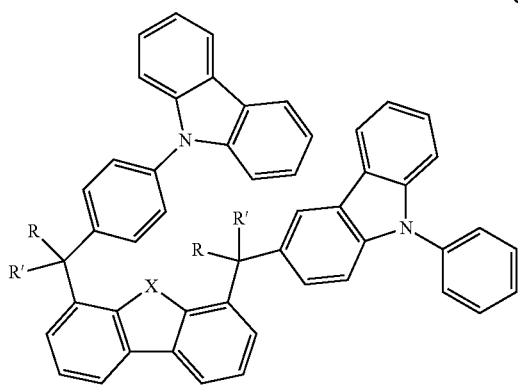

Compound 55 R = R' = H, X = S
Compound 56 R = R' = CH₃, X = S
Compound 57 R = R' = Ph, X = S
Compound 58 R = R' = H, X = O
Compound 59 R = R' = CH₃, X = O
Compound 60 R = R' = Ph, X = O

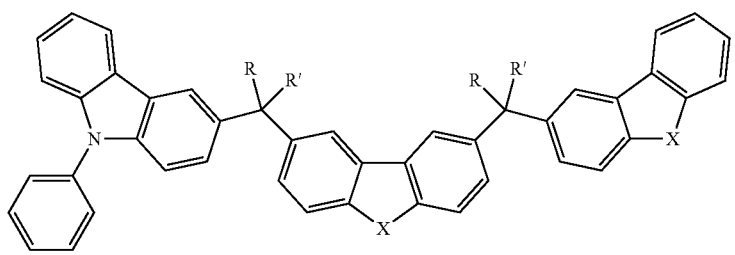

Compound 61 R = R' = H, X = S
Compound 62 R = R' = CH₃, X = S
Compound 63 R = R' = Ph, X = S
Compound 64 R = R' = H, X = O
Compound 65 R = R' = CH₃, X = O
Compound 66 R = R' = Ph, X = O

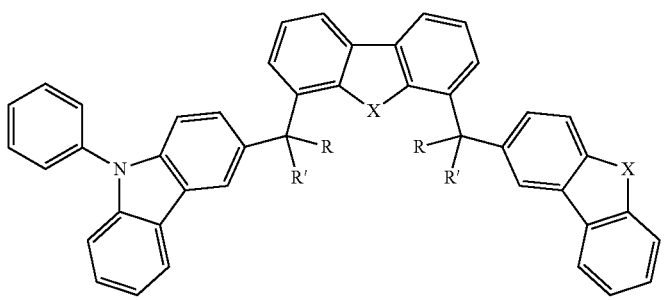

Compound 67 R = R' = H, X = S
Compound 68 R = R' = CH₃, X = S
Compound 69 R = R' = Ph, X = S
Compound 70 R = R' = H, X = O
Compound 71 R = R' = CH₃, X = O
Compound 72 R = R' = Ph, X = O -continued

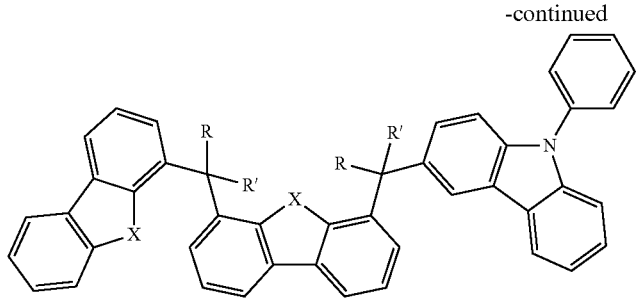

Compound 73 R = R' = H, X = S
Compound 74 R = R' = CH₃, X = S
Compound 75 R = R' = Ph, X = S
Compound 76 R = R' = H, X = O
Compound 77 R = R' = CH₃, X = O
Compound 78 R = R' = Ph, X = O

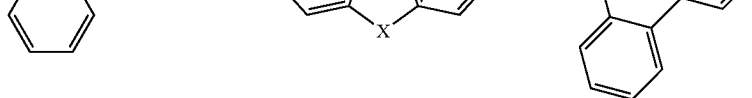

Compound 79 R = R' = H, X = S
Compound 80 R = R' = CH₃, X = S
Compound 81 R = R' = Ph, X = S
Compound 82 R = R' = H, X = O
Compound 83 R = R' = CH₃, X = O
Compound 84 R = R' = Ph, X = O

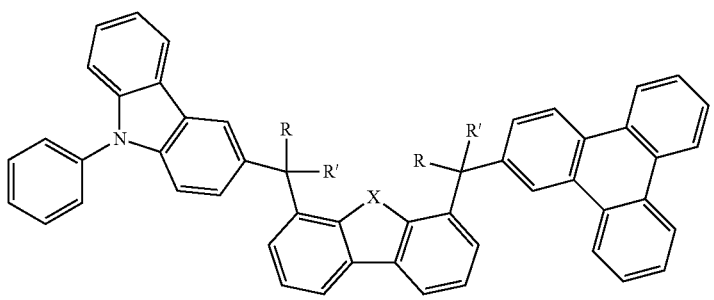

Compound 85 R = R' = H, X = S
Compound 86 R = R' = CH₃, X = S
Compound 87 R = R' = Ph, X = S
Compound 88 R = R' = H, X = O
Compound 89 R = R' = CH₃, X = O
Compound 90 R = R' = Ph, X = O -continued

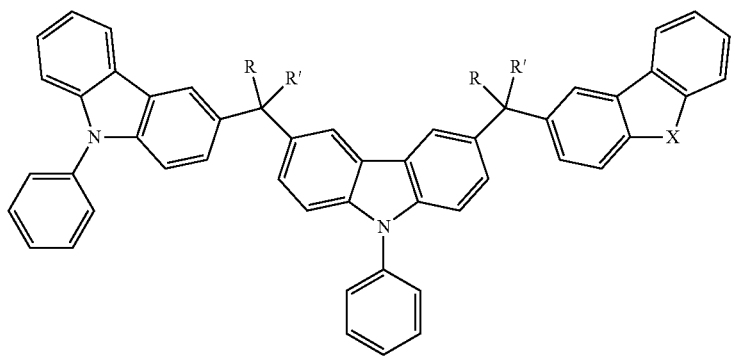

Compound 91 R = R' = H, X = S
Compound 92 R = R' = CH₃, X = S
Compound 93 R = R' = Ph, X = S
Compound 94 R = R' = H, X = O
Compound 95 R = R' = CH₃, X = O
Compound 96 R = R' = Ph, X = O

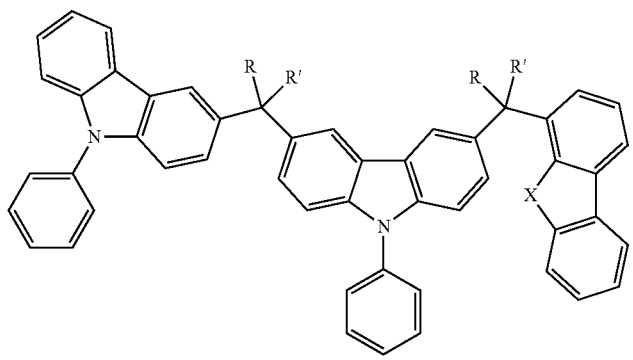

Compound 97 R = R' = H, X = S
Compound 98 R = R' = CH₃, X = S
Compound 99 R = R' = Ph, X = S
Compound 100 R = R' = H, X = O
Compound 101 R = R' = CH₃, X = O
Compound 102 R = R' = Ph, X = O

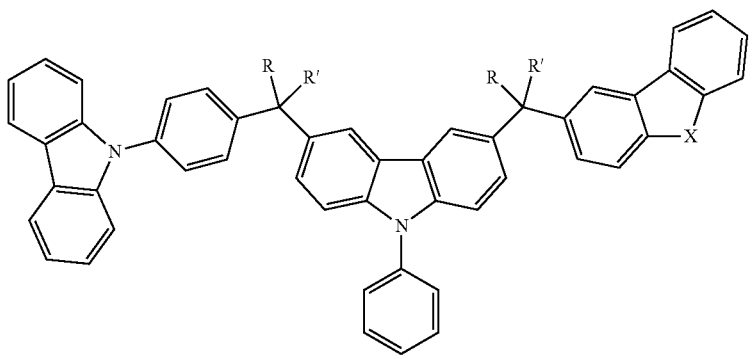

Compound 103 R = R' = H, X = S
Compound 104 R = R' = CH₃, X = S
Compound 105 R = R' = Ph, X = S
Compound 106 R = R' = H, X = O
Compound 107 R = R' = CH₃, X = O
Compound 108 R = R' = Ph, X = O -continued

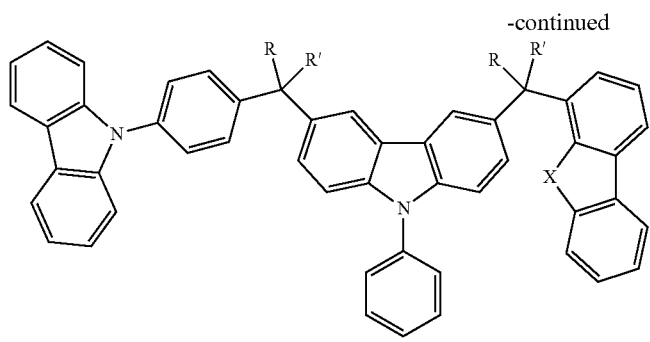

Compound 109 R = R' = H, X = S
Compound 110 R = R' = CH₃, X = S
Compound 111 R = R' = Ph, X = S
Compound 112 R = R' = H, X = O
Compound 113 R = R' = CH₃, X = O
Compound 114 R = R' = Ph, X = O

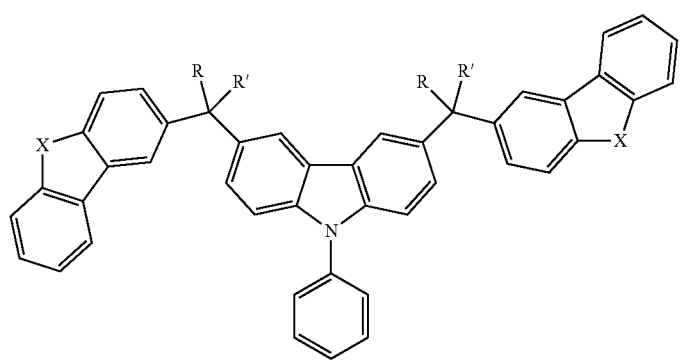

Compound 115 R = R' = H, X = S
Compound 116 R = R' = CH₃, X = S
Compound 117 R = R' = Ph, X = S
Compound 118 R = R' = H, X = O
Compound 119 R = R' = CH₃, X = O
Compound 120 R = R' = Ph, X = O

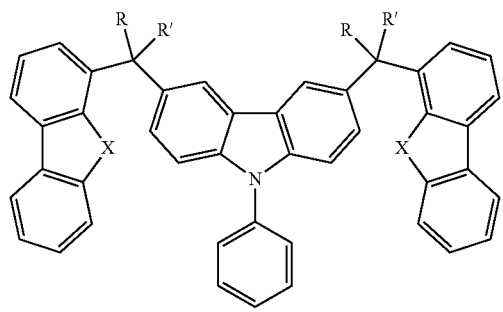

Compound 121 R = R' = H, X = S
Compound 122 R = R' = CH₃, X = S
Compound 123 R = R' = Ph, X = S
Compound 124 R = R' = H, X = O
Compound 125 R = R' = CH₃, X = O
Compound 126 R = R' = Ph, X = O -continued

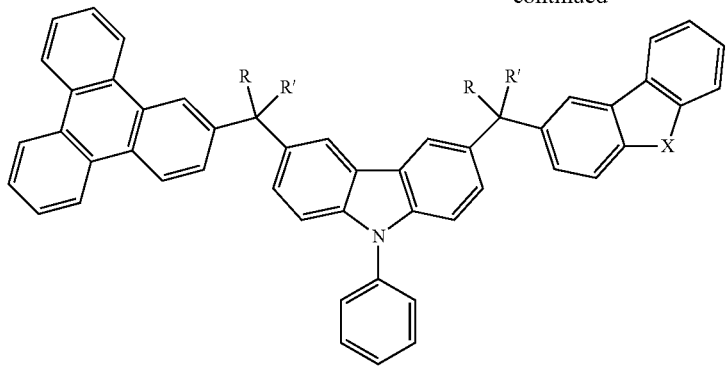

Compound 127 R = R' = H, X = S
Compound 128 R = R' = CH₃, X = S
Compound 129 R = R' = Ph, X = S
Compound 130 R = R' = H, X = O
Compound 131 R = R' = CH₃, X = O
Compound 132 R = R' = Ph, X = O

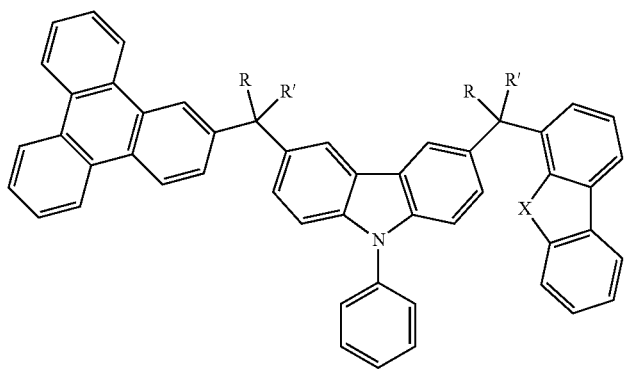

Compound 133 R = R' = H, X = S
Compound 134 R = R' = CH₃, X = S
Compound 135 R = R' = Ph, X = S
Compound 136 R = R' = H, X = O
Compound 137 R = R' = CH₃, X = O
Compound 138 R = R' = Ph, X = O

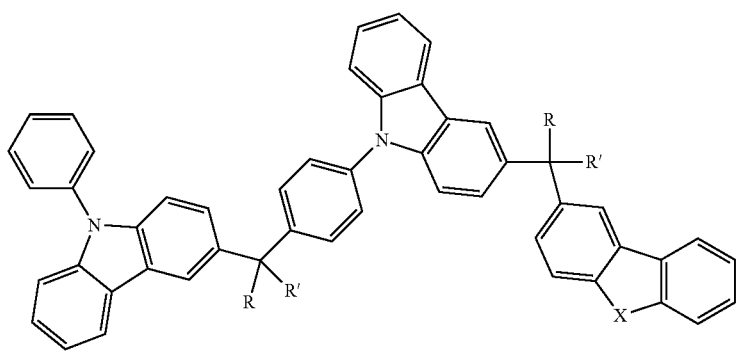

Compound 139 R = R' = H, X = S
Compound 140 R = R' = CH₃, X = S
Compound 141 R = R' = Ph, X = S
Compound 142 R = R' = H, X = O
Compound 143 R = R' = CH₃, X = O
Compound 144 R = R' = Ph, X = O -continued

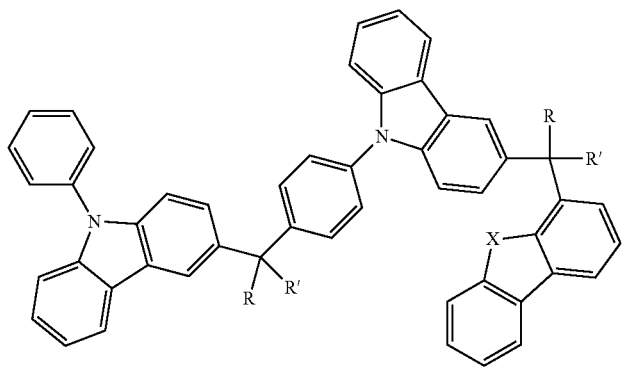

Compound 145 R = R' = H, X = S
Compound 146 R = R' = CH₃, X = S
Compound 147 R = R' = Ph, X = S
Compound 148 R = R' = H, X = O
Compound 149 R = R' = CH₃, X = O
Compound 150 R = R' = Ph, X = O

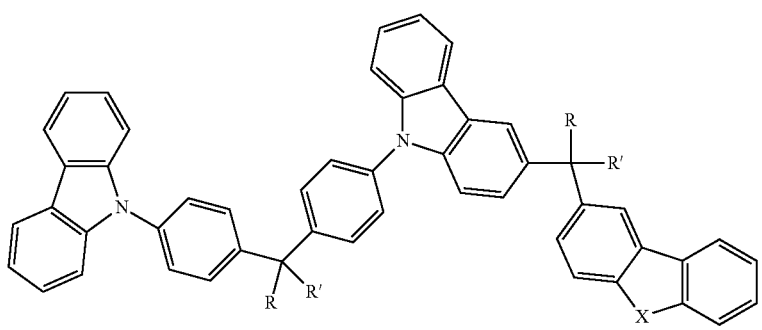

Compound 151 R = R' = H, X = S
Compound 152 R = R' = CH₃, X = S
Compound 153 R = R' = Ph, X = S
Compound 154 R = R' = H, X = O
Compound 155 R = R' = CH₃, X = O
Compound 156 R = R' = Ph, X = O

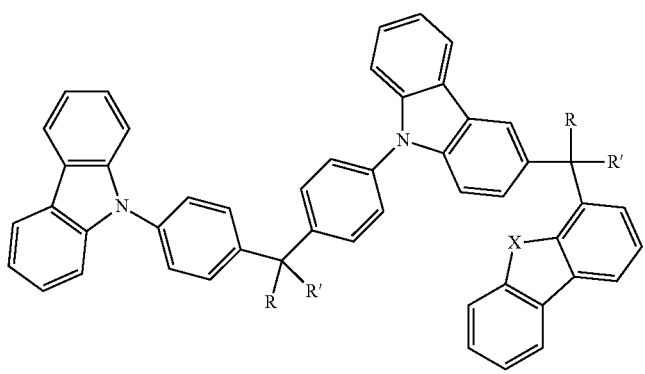

Compound 157 R = R' = H, X = S
Compound 158 R = R' = CH₃, X = S
Compound 159 R = R' = Ph, X = S
Compound 160 R = R' = H, X = O
Compound 161 R = R' = CH₃, X = O
Compound 162 R = R' = Ph, X = O -continued

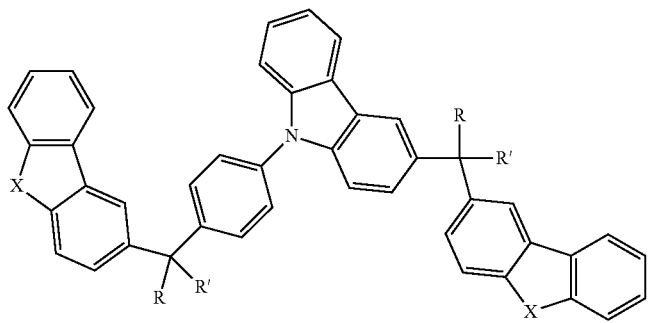

Compound 163 R = R' = H, X = S
Compound 164 R = R' = CH₃, X = S
Compound 165 R = R' = Ph, X = S
Compound 166 R = R' = H, X = O
Compound 167 R = R' = CH₃, X = O
Compound 168 R = R' = Ph, X = O

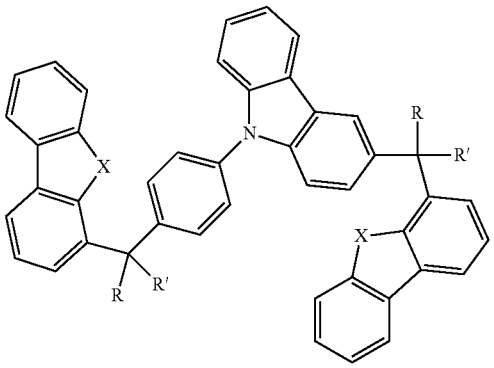

Compound 169 R = R' = H, X = S
Compound 170 R = R' = CH₃, X = S
Compound 171 R = R' = Ph, X = S
Compound 172 R = R' = H, X = O
Compound 173 R = R' = CH₃, X = O
Compound 174 R = R' = Ph, X = O

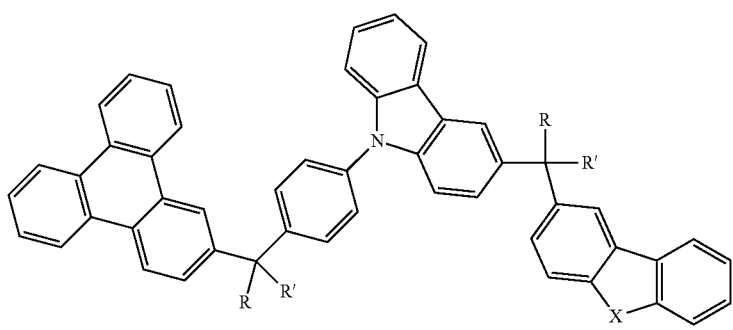

Compound 175 R = R' = H, X = S
Compound 176 R = R' = CH₃, X = S
Compound 177 R = R' = Ph, X = S
Compound 178 R = R' = H, X = O
Compound 179 R = R' = CH₃, X = O
Compound 180 R = R' = Ph, X = O

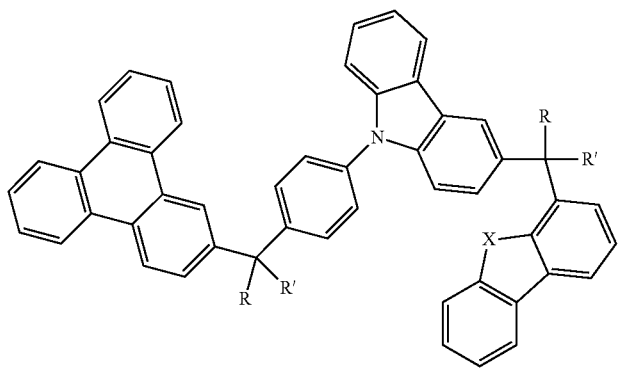

Compound 181 R = R' = H, X = S
Compound 182 R = R' = CH₃, X = S
Compound 183 R = R' = Ph, X = S
Compound 184 R = R' = H, X = O
Compound 185 R = R' = CH₃, X = O
Compound 186 R = R' = Ph, X = O

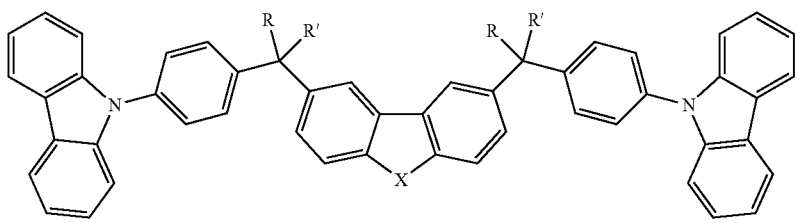

Compound 187 R = R' = H, X = S
Compound 188 R = R' = CH₃, X = S
Compound 189 R = R' = Ph, X = S
Compound 190 R = R' = H, X = O
Compound 191 R = R' = CH₃, X = O
Compound 192 R = R' = Ph, X = O

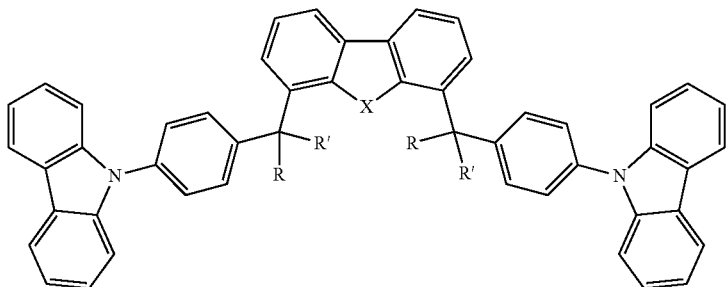

Compound 193 R = R' = H, X = S
Compound 194 R = R' = CH₃, X = S
Compound 195 R = R' = Ph, X = S
Compound 196 R = R' = H, X = O
Compound 197 R = R' = CH₃, X = O
Compound 198 R = R' = Ph, X = O

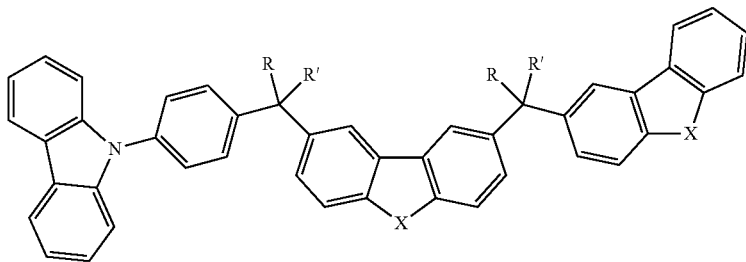

Compound 199 R = R' = H, X = S
Compound 200 R = R' = CH₃, X = S
Compound 201 R = R' = Ph, X = S
Compound 202 R = R' = H, X = O
Compound 203 R = R' = CH₃, X = O
Compound 204 R = R' = Ph, X = O

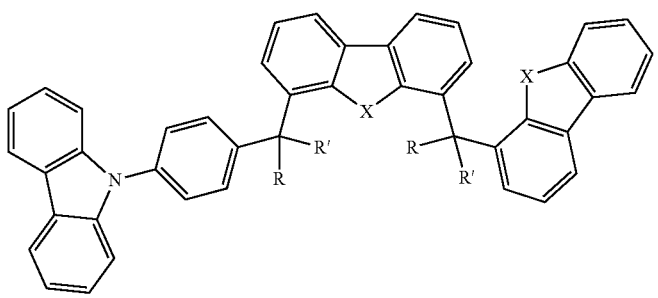

Compound 205 R = R' = H, X = S
Compound 206 R = R' = CH₃, X = S
Compound 207 R = R' = Ph, X = S
Compound 208 R = R' = H, X = O
Compound 209 R = R' = CH₃, X = O
Compound 210 R = R' = Ph, X = O -continued

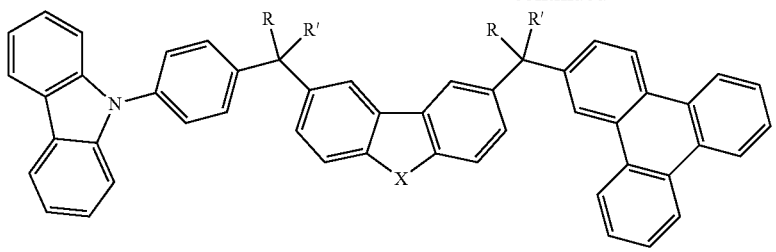

Compound 211 R = R' = H, X = S
Compound 212 R = R' = CH₃, X = S
Compound 213 R = R' = Ph, X = S
Compound 214 R = R' = H, X = O
Compound 215 R = R' = CH₃, X = O
Compound 216 R = R' = Ph, X = O

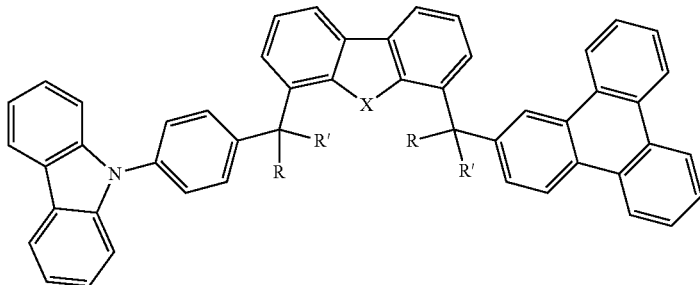

Compound 217 R = R' = H, X = S
Compound 218 R = R' = CH₃, X = S
Compound 219 R = R' = Ph, X = S
Compound 220 R = R' = H, X = O
Compound 221 R = R' = CH₃, X = O
Compound 222 R = R' = Ph, X = O

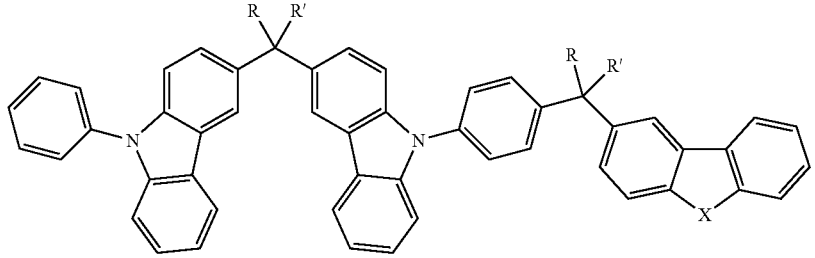

Compound 223 R = R' = H, X = S
Compound 224 R = R' = CH₃, X = S
Compound 225 R = R' = Ph, X = S
Compound 226 R = R' = H, X = O
Compound 227 R = R' = CH₃, X = O
Compound 228 R = R' = Ph, X = O

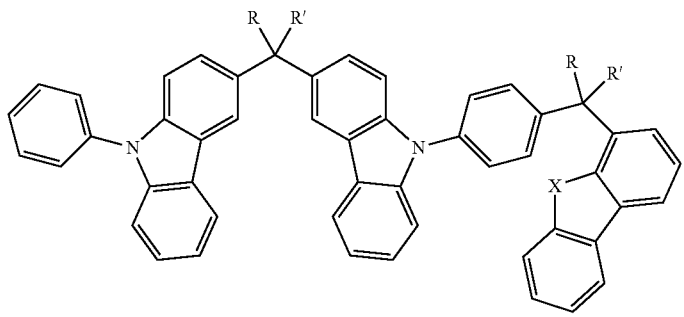

Compound 229 R = R' = H, X = S
Compound 230 R = R' = CH₃, X = S
Compound 231 R = R' = Ph, X = S
Compound 232 R = R' = H, X = O
Compound 233 R = R' = CH₃, X = O
Compound 234 R = R' = Ph, X = O

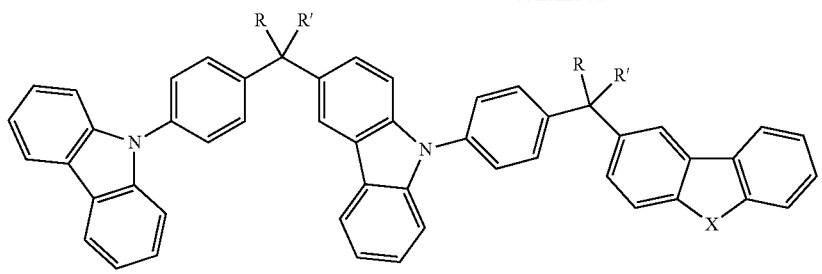

Compound 235 R = R' = H, X = S
Compound 236 R = R' = CH₃, X = S
Compound 237 R = R' = Ph, X = S
Compound 238 R = R' = H, X = O
Compound 239 R = R' = CH₃, X = O
Compound 240 R = R' = Ph, X = O

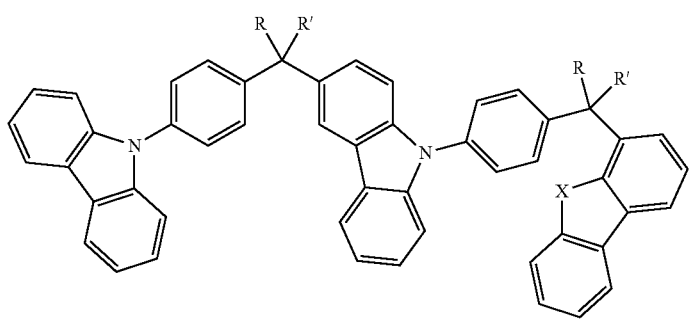

Compound 241 R = R' = H, X = S
Compound 242 R = R' = CH₃, X = S
Compound 243 R = R' = Ph, X = S
Compound 244 R = R' = H, X = O
Compound 245 R = R' = CH₃, X = O
Compound 246 R = R' = Ph, X = O

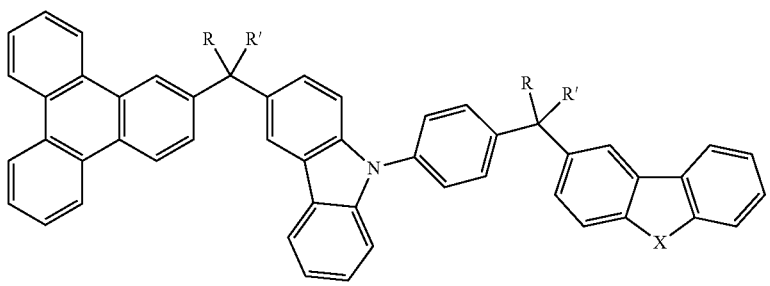

Compound 247 R = R' = H, X = S
Compound 248 R = R' = CH₃, X = S
Compound 249 R = R' = Ph, X = S
Compound 250 R = R' = H, X = O
Compound 251 R = R' = CH₃, X = O
Compound 252 R = R' = Ph, X = O

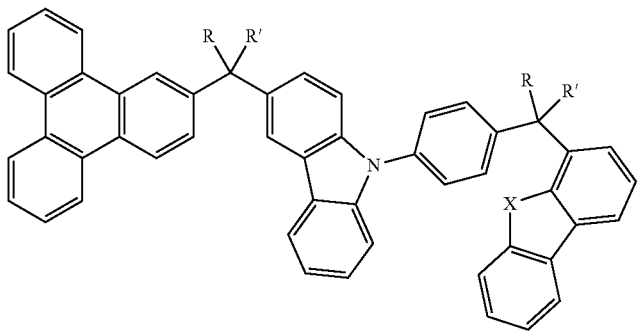

Compound 253 R = R' = H, X = S
Compound 254 R = R' = CH₃, X = S
Compound 255 R = R' = Ph, X = S
Compound 256 R = R' = H, X = O
Compound 257 R = R' = CH₃, X = O
Compound 258 R = R' = Ph, X = O

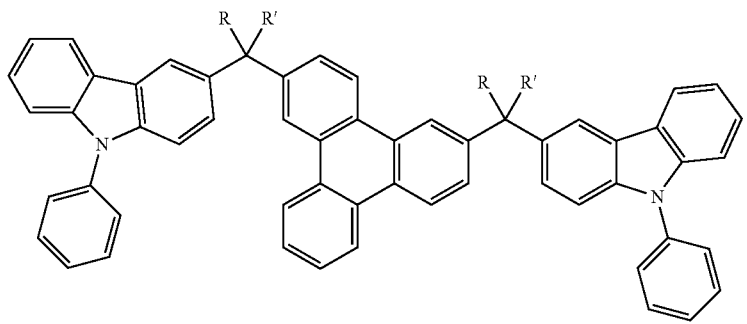

Compound 259 R = R' = H
Compound 260 R = R' = CH₃
Compound 261 R = R' = Ph

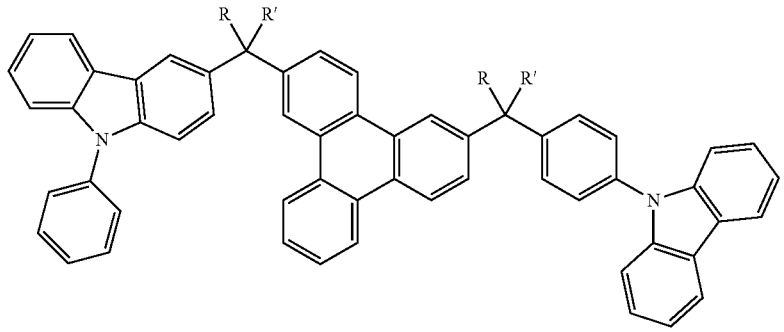

Compound 262 R = R' = H
Compound 263 R = R' = CH₃
Compound 264 R = R' = Ph

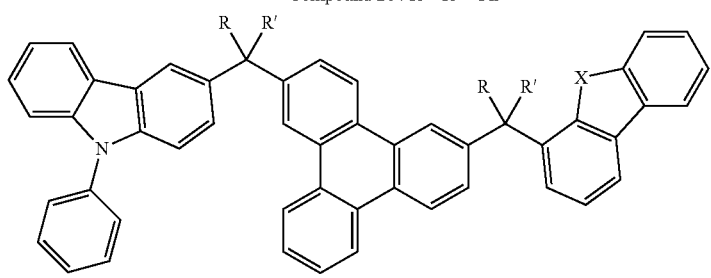

Compound 265 R = R' = H, X = S
Compound 266 R = R' = CH₃, X = S
Compound 267 R = R' = Ph, X = S
Compound 268 R = R' = H, X = O
Compound 269 R = R' = CH₃, X = O
Compound 270 R = R' = Ph, X = O -continued
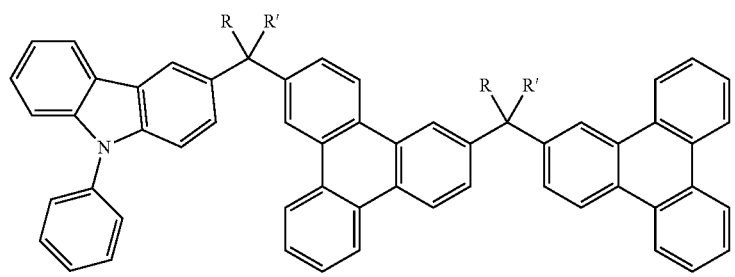
Compound 271 R = R' = H
Compound 272 R = R' = CH₃
Compound 273 R = R' = Ph
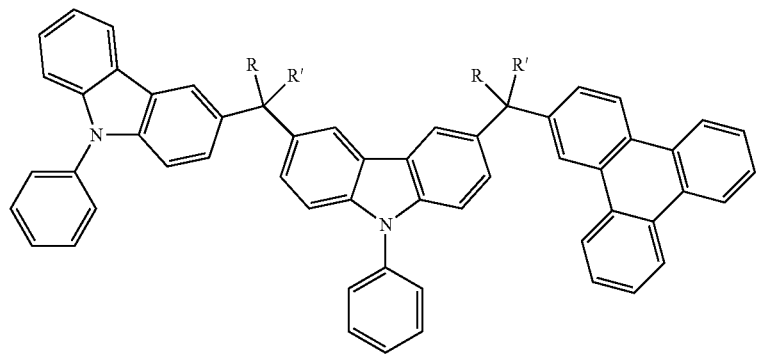
Compound 274 R = R' = H
Compound 275 R = R' = CH₃
Compound 276 R = R' = Ph
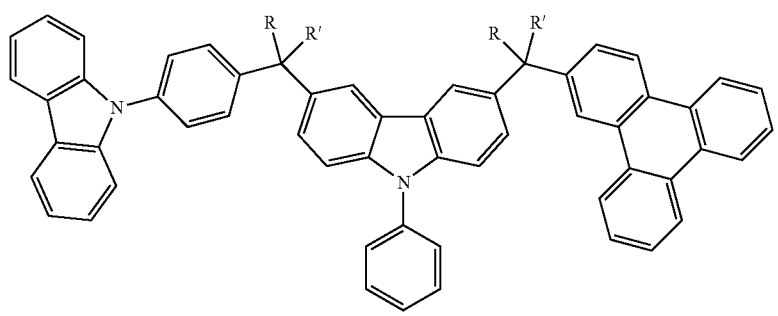
Compound 277 R = R' = H
Compound 278 R = R' = CH₃
Compound 279 R = R' = Ph
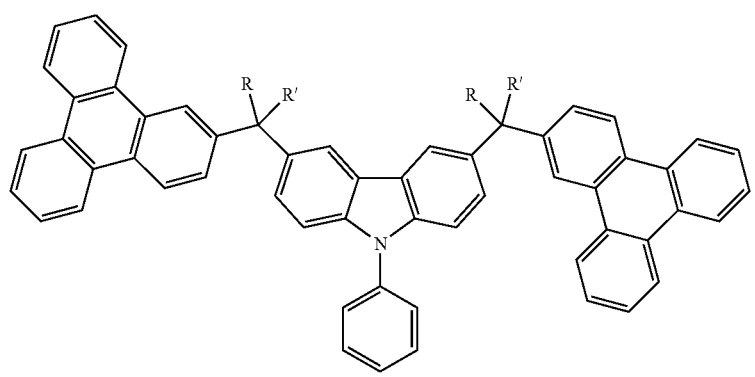
Compound 280 R = R' = H
Compound 281 R = R' = CH₃
Compound 282 R = R' = Ph -continued
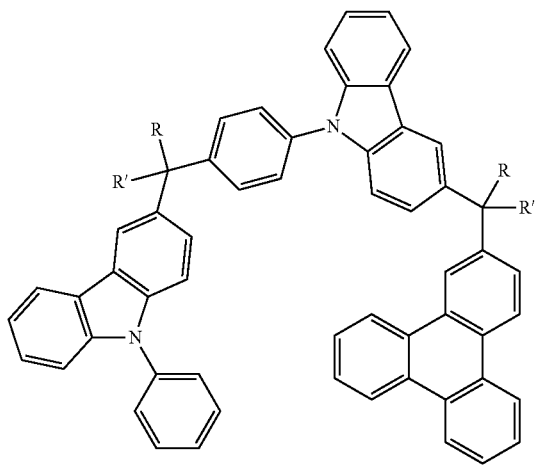
Compound 283 R = R' = H
Compound 284 R = R' = CH₃
Compound 285 R = R' = Ph
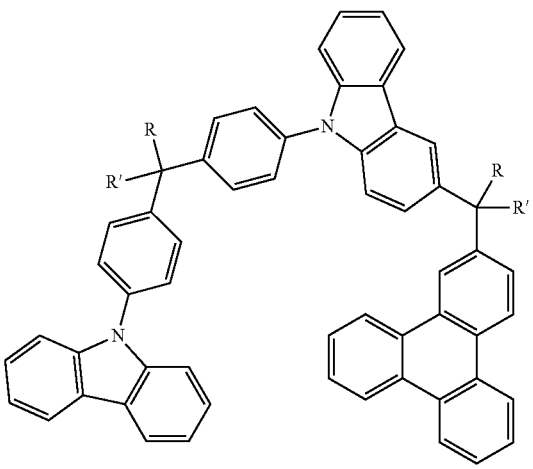
Compound 286 R = R' = H
Compound 287 R = R' = CH₃
Compound 288 R = R' = Ph
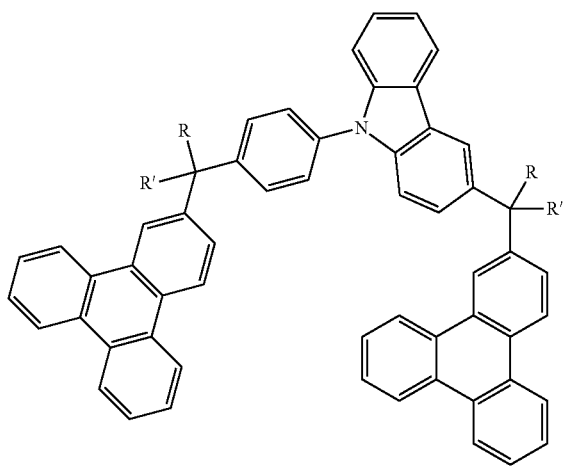
Compound 289 R = R' = H
Compound 290 R = R' = CH₃
Compound 291 R = R' = Ph
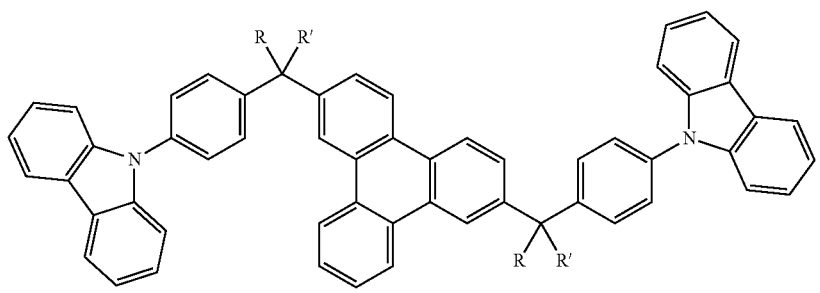
Compound 292 R = R' = H
Compound 293 R = R' = CH₃
Compound 294 R = R' = Ph -continued

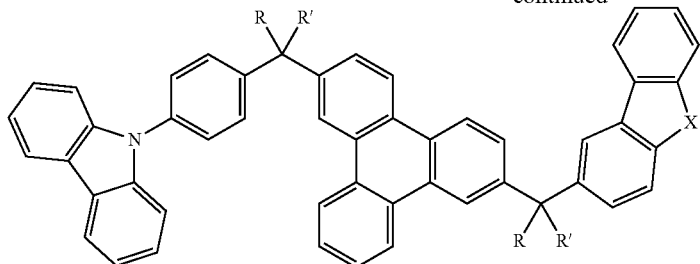

Compound 295 R = R' = H, X = S
Compound 296 R = R' = CH₃, X = S
Compound 297 R = R' = Ph, X = S
Compound 298 R = R' = H, X = O
Compound 299 R = R' = CH₃, X = O
Compound 300 R = R' = Ph, X = O

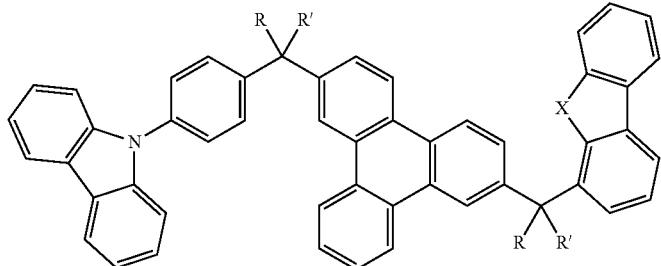

Compound 301 R = R' = H, X = S
Compound 302 R = R' = CH₃, X = S
Compound 303 R = R' = Ph, X = S
Compound 304 R = R' = H, X = O
Compound 305 R = R' = CH₃, X = O
Compound 306 R = R' = Ph, X = O

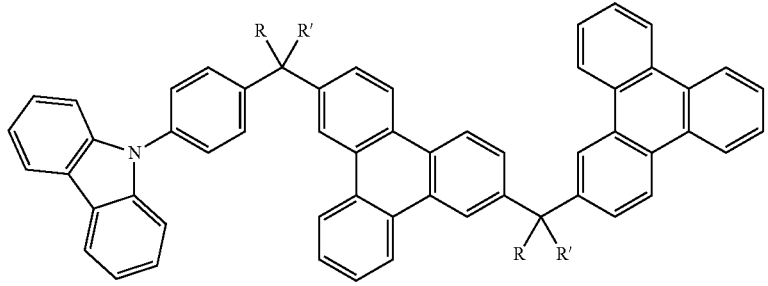

Compound 307 R = R' = H, X = S
Compound 308 R = R' = CH₃, X = S
Compound 309 R = R' = Ph, X = S
Compound 310 R = R' = H, X = O
Compound 311 R = R' = CH₃, X = O
Compound 312 R = R' = Ph, X = O

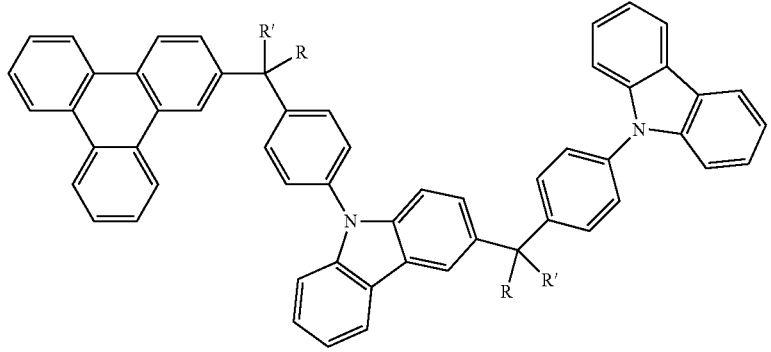

Compound 313 R = R' = H
Compound 314 R = R' = CH₃
Compound 315 R = R' = Ph

-continued
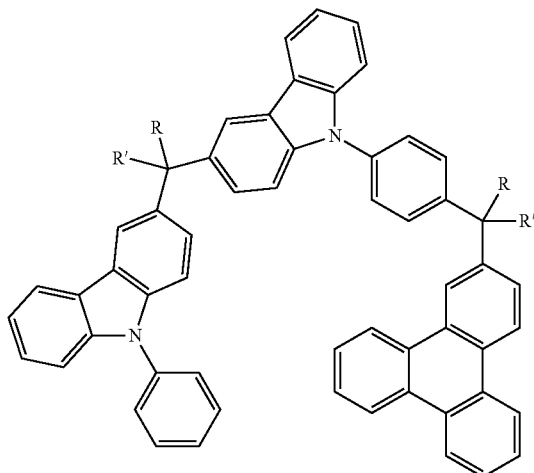
Compound 316 R = R' = H
Compound 317 R = R' = CH₃
Compound 318 R = R' = Ph
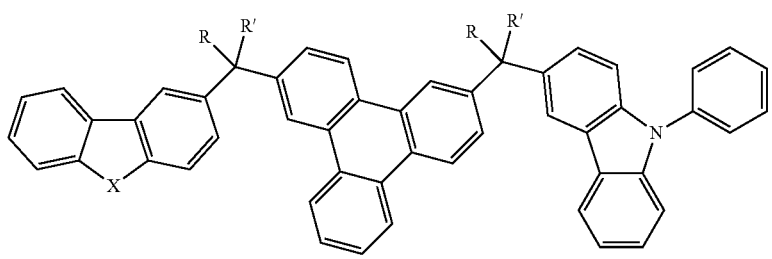
Compound 319 R = R' = H, X = S
Compound 320 R = R' = CH₃, X = S
Compound 321 R = R' = Ph, X = S
Compound 322 R = R' = H, X = O
Compound 323 R = R' = CH₃, X = O
Compound 324 R = R' = Ph, X = O
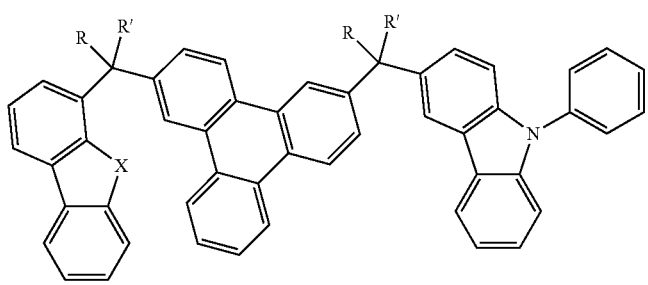
Compound 325 R = R' = H, X = S
Compound 326 R = R' = CH₃, X = S
Compound 327 R = R' = Ph, X = S
Compound 328 R = R' = H, X = O
Compound 329 R = R' = CH₃, X = O
Compound 330 R = R' = Ph, X = O -continued

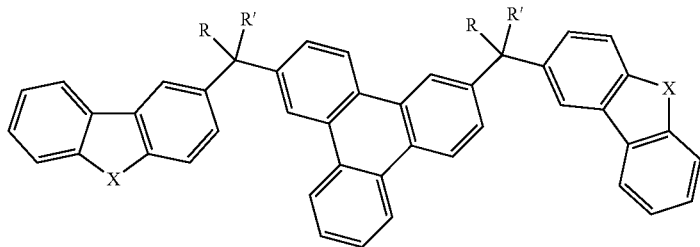

Compound 331 R = R' = H, X = S
Compound 332 R = R' = CH₃, X = S
Compound 333 R = R' = Ph, X = S
Compound 334 R = R' = H, X = O
Compound 335 R = R' = CH₃, X = O
Compound 336 R = R' = Ph, X = O

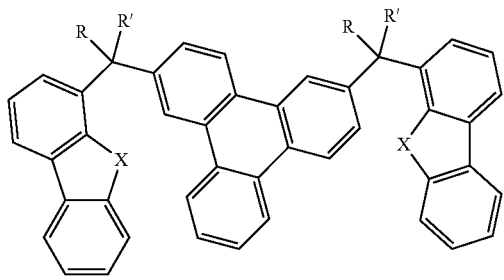

Compound 337 R = R' = H, X = S
Compound 338 R = R' = CH₃, X = S
Compound 339 R = R' = Ph, X = S
Compound 340 R = R' = H, X = O
Compound 341 R = R' = CH₃, X = O
Compound 342 R = R' = Ph, X = O

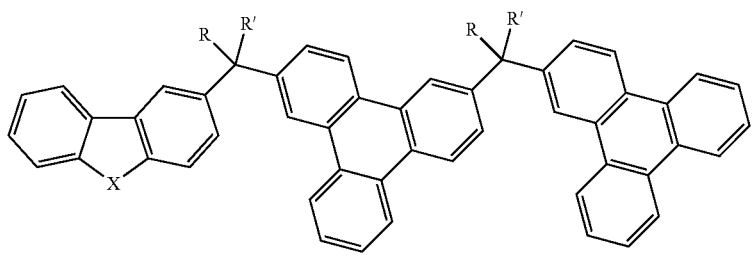

Compound 343 R = R' = H, X = S
Compound 344 R = R' = CH₃, X = S
Compound 345 R = R' = Ph, X = S
Compound 346 R = R' = H, X = O
Compound 347 R = R' = CH₃, X = O
Compound 348 R = R' = Ph, X = O

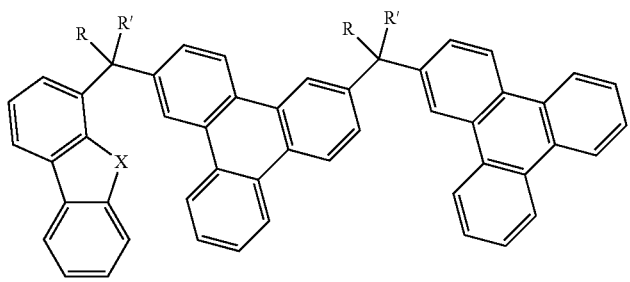

Compound 349 R = R' = H, X = S
Compound 350 R = R' = CH₃, X = S
Compound 351 R = R' = Ph, X = S
Compound 352 R = R' = H, X = O
Compound 353 R = R' = CH₃, X = O
Compound 354 R = R' = Ph, X = O -continued

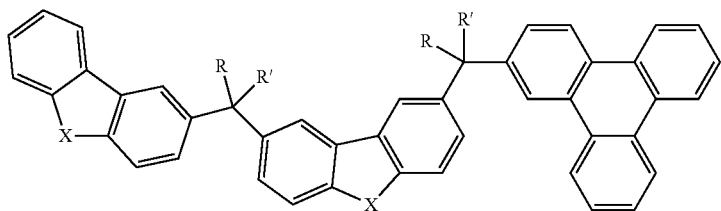

Compound 355 R = R' = H, X = S
Compound 356 R = R' = CH$_3$, X = S
Compound 357 R = R' = Ph, X = S
Compound 358 R = R' = H, X = O
Compound 359 R = R' = CH$_3$, X = O
Compound 360 R = R' = Ph, X = O

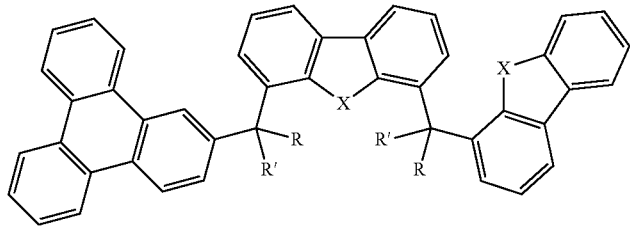

Compound 361 R = R' = H, X = S
Compound 362 R = R' = CH$_3$, X = S
Compound 363 R = R' = Ph, X = S
Compound 364 R = R' = H, X = O
Compound 365 R = R' = CH$_3$, X = O
Compound 366 R = R' = Ph, X = O

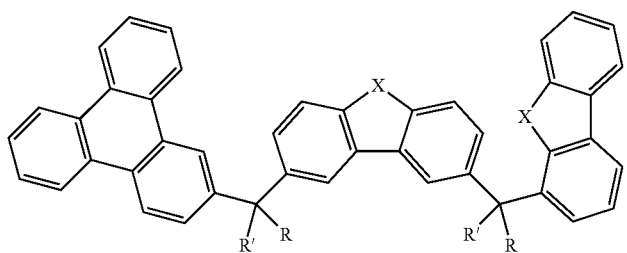

Compound 367 R = R' = H, X = S
Compound 368 R = R' = CH$_3$, X = S
Compound 369 R = R' = Ph, X = S
Compound 370 R = R' = H, X = O
Compound 371 R = R' = CH$_3$, X = O
Compound 372 R = R' = Ph, X = O

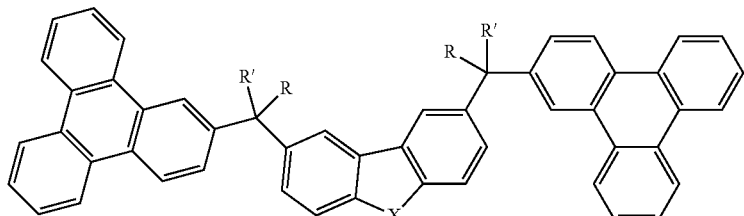

Compound 373 R = R' = H, X = S
Compound 374 R = R' = CH$_3$, X = S
Compound 375 R = R' = Ph, X = S
Compound 376 R = R' = H, X = O
Compound 377 R = R' = CH$_3$, X = O
Compound 378 R = R' = Ph, X = O -continued

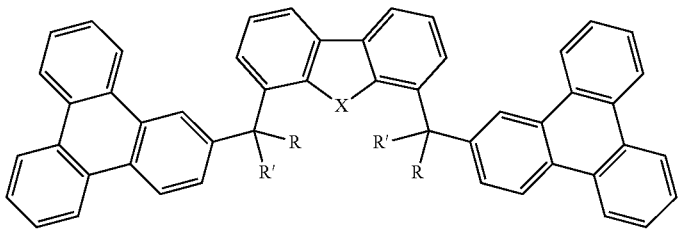

Compound 379 R = R' = H, X = S
Compound 380 R = R' = CH₃, X = S
Compound 381 R = R' = Ph, X = S
Compound 382 R = R' = H, X = O
Compound 383 R = R' = CH₃, X = O
Compound 384 R = R' = Ph, X = O

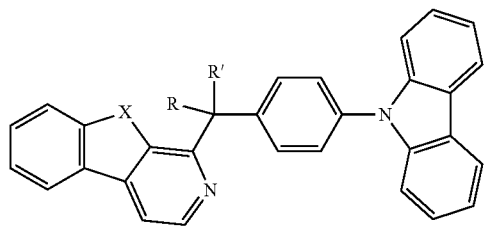

Compound 385 R = R' = H, X = S
Compound 386 R = R' = CH₃, X = S
Compound 387 R = R' = Ph, X = S
Compound 388 R = R' = H, X = O
Compound 389 R = R' = CH₃, X = O
Compound 390 R = R' = Ph, X = O

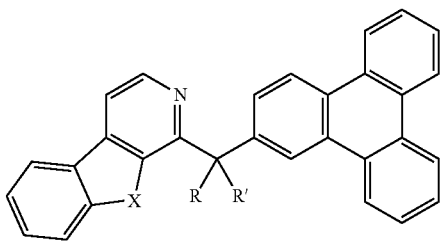

Compound 391 R = R' = H, X = S
Compound 392 R = R' = CH₃, X = S
Compound 393 R = R' = Ph, X = S
Compound 394 R = R' = H, X = O
Compound 395 R = R' = CH₃, X = O
Compound 396 R = R' = Ph, X = O

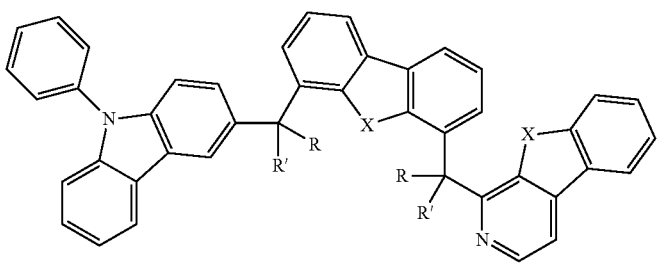

Compound 397 R = R' = H, X = S
Compound 398 R = R' = CH₃, X = S
Compound 399 R = R' = Ph, X = S
Compound 400 R = R' = H, X = O
Compound 401 R = R' = CH₃, X = O
Compound 402 R = R' = Ph, X = O

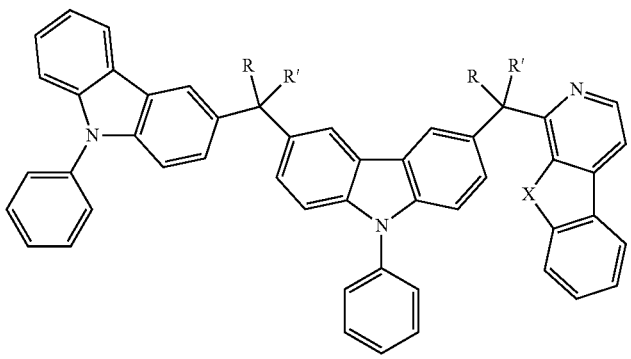

Compound 403 R = R' = H, X = S
Compound 404 R = R' = CH₃, X = S
Compound 405 R = R' = Ph, X = S
Compound 406 R = R' = H, X = O
Compound 407 R = R' = CH₃, X = O
Compound 408 R = R' = Ph, X = O

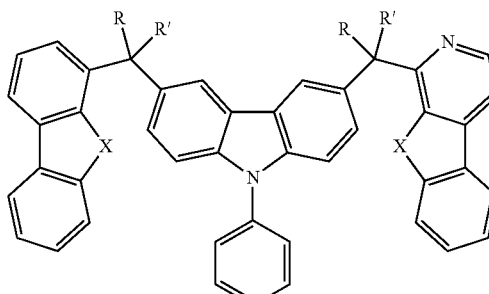

Compound 409 R = R' = H, X = S
Compound 410 R = R' = CH₃, X = S
Compound 411 R = R' = Ph, X = S
Compound 412 R = R' = H, X = O
Compound 413 R = R' = CH₃, X = O
Compound 414 R = R' = Ph, X = O -continued

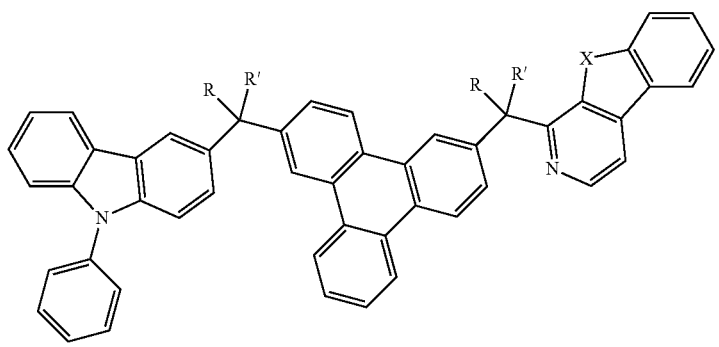

Compound 415 R = R' = H, X = S
Compound 416 R = R' = CH₃, X = S
Compound 417 R = R' = Ph, X = S
Compound 418 R = R' = H, X = O
Compound 419 R = R' = CH₃, X = O
Compound 420 R = R' = Ph, X = O

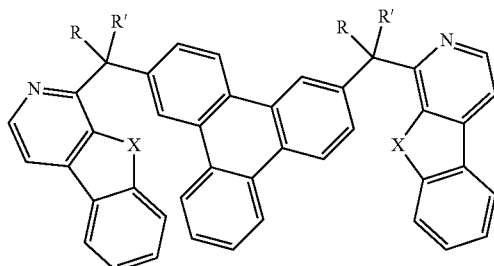

Compound 421 R = R' = H, X = S
Compound 422 R = R' = CH₃, X = S
Compound 423 R = R' = Ph, X = S
Compound 424 R = R' = H, X = O
Compound 425 R = R' = CH₃, X = O
Compound 426 R = R' = Ph, X = O

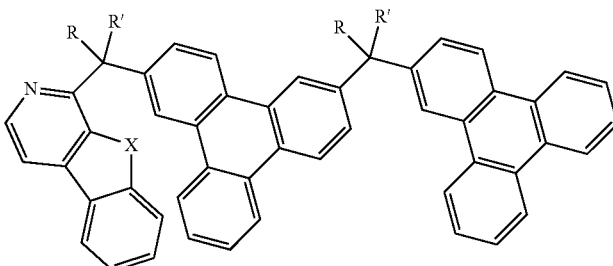

Compound 427 R = R' = H, X = S
Compound 428 R = R' = CH₃, X = S
Compound 429 R = R' = Ph, X = S
Compound 430 R = R' = H, X = O
Compound 431 R = R' = CH₃, X = O
Compound 432 R = R' = Ph, X = O

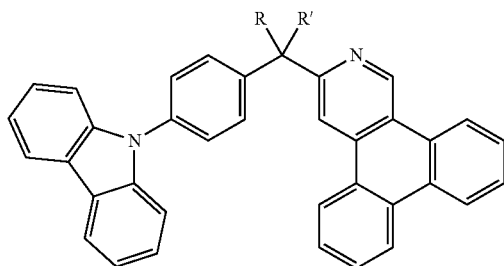

Compound 433 R = R' = H
Compound 434 R = R' = CH₃
Compound 435 R = R' = Ph

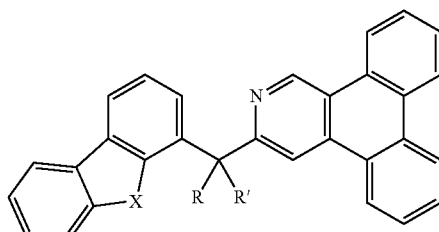

Compound 436 R = R' = H, X = S
Compound 437 R = R' = CH₃, X = S
Compound 438 R = R' = Ph, X = S
Compound 439 R = R' = H, X = O
Compound 440 R = R' = CH₃, X = O
Compound 441 R = R' = Ph, X = O

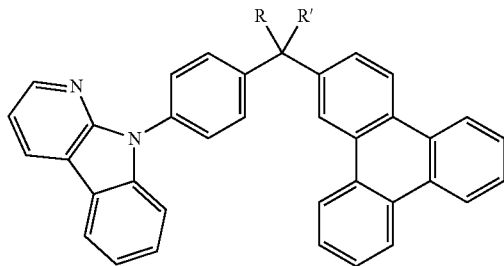

Compound 442 R = R' = H
Compound 443 R = R' = CH₃
Compound 444 R = R' = Ph

-continued

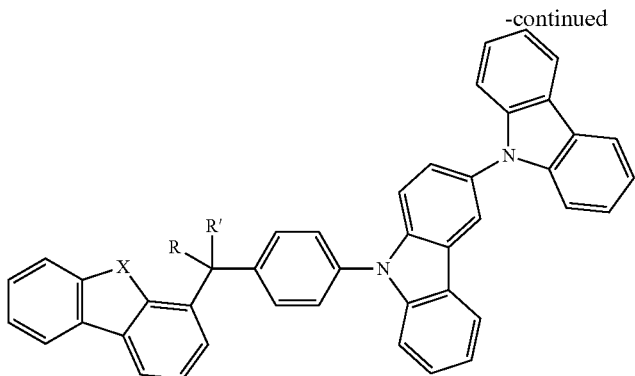

Compound 445 R = R' = H, X = S
Compound 446 R = R' = CH₃, X = S
Compound 447 R = R' = Ph, X = S
Compound 448 R = R' = H, X = O
Compound 449 R = R' = CH₃, X = O
Compound 450 R = R' = Ph, X = O

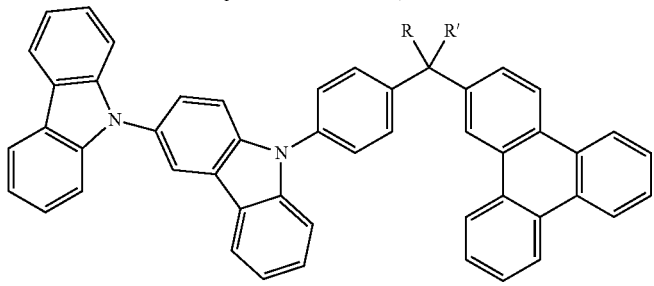

Compound 451 R = R' = H
Compound 452 R = R' = CH₃
Compound 453 R = R' = Ph

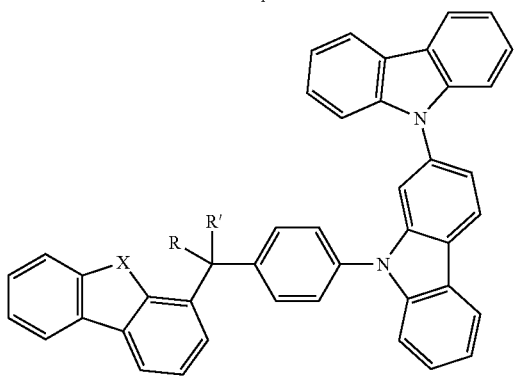

Compound 454 R = R' = H, X = S
Compound 455 R = R' = CH₃, X = S
Compound 456 R = R' = Ph, X = S
Compound 457 R = R' = H, X = O
Compound 458 R = R' = CH₃, X = O
Compound 459 R = R' = Ph, X = O 19. The compound of claim 1, wherein A is dibenzothiophene, L is —CH₂—, and B is N-phenyl carbazole.

20. A first device comprising a first organic light emitting device, the first organic light emitting device comprising:
an anode;
a cathode; and
an organic layer, disposed between the anode and the cathode, comprising a compound having formula I:

A-L-B   (I);

wherein A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;
wherein A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein L is selected from the group consisting of alkyl, cycloalkyl, substituted alkyl, and substituted cycloalkyl; and wherein L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

21. A formulation comprising a compound having formula I:

A-L-B       (I);

wherein A and B are each different selections selected from the group consisting of N-phenyl carbazole, dibenzofuran, dibenzothiophene, triphenylene, aza-(N-phenyl carbazole), aza-carbazole, aza-dibenzofuran, aza-dibenzothiophene, and aza-triphenylene;

wherein A and B can be further substituted by one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and wherein two adjacent substituents can optionally join to form a fused ring;

wherein L is selected from the group consisting of alkyl, cycloalkyl, substituted alkyl, and substituted cycloalkyl; and wherein L can be substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

* * * * *